US011986269B2

(12) United States Patent
Wang et al.

(10) Patent No.: US 11,986,269 B2
(45) Date of Patent: May 21, 2024

(54) SPATIOTEMPORAL ANTIALIASING IN PHOTOACOUSTIC COMPUTED TOMOGRAPHY

(71) Applicant: California Institute of Technology, Pasadena, CA (US)

(72) Inventors: Lihong Wang, Arcadia, CA (US); Peng Hu, Pasadena, CA (US); Lei Li, Arcadia, CA (US)

(73) Assignee: California Institute of Technology, Pasadena, CA (US)

( * ) Notice: Subject to any disclaimer, the term of this patent is extended or adjusted under 35 U.S.C. 154(b) by 268 days.

(21) Appl. No.: 17/090,752

(22) Filed: Nov. 5, 2020

(65) Prior Publication Data

US 2021/0132005 A1    May 6, 2021

Related U.S. Application Data

(60) Provisional application No. 62/931,024, filed on Nov. 5, 2019.

(51) Int. Cl.
| | |
|---|---|
| *G01N 29/42* | (2006.01) |
| *A61B 5/00* | (2006.01) |
| *A61B 8/13* | (2006.01) |
| *G01N 29/06* | (2006.01) |
| *G01N 29/24* | (2006.01) |

(52) U.S. Cl.
CPC .............. *A61B 5/0095* (2013.01); *A61B 8/13* (2013.01); *G01N 29/0672* (2013.01); *G01N 29/2418* (2013.01); *G01N 29/42* (2013.01); *G01N 2291/02475* (2013.01)

(58) Field of Classification Search
CPC .... A61B 5/0095; A61B 8/13; G01N 29/0672; G01N 29/2418; G01N 29/42; G01N 2291/02475
USPC ........................................................ 600/407
See application file for complete search history.

(56) References Cited

U.S. PATENT DOCUMENTS

| | | | |
|---|---|---|---|
| 4,029,756 | A | 6/1977 | Gaafar |
| 4,127,318 | A | 11/1978 | Determann et al. |
| 4,255,971 | A | 3/1981 | Rosencwaig |
| 4,267,732 | A | 5/1981 | Quate |
| 4,284,324 | A | 8/1981 | Huignard et al. |
| 4,375,818 | A | 3/1983 | Suwaki et al. |
| 4,385,634 | A | 5/1983 | Bowen |
| 4,430,897 | A | 2/1984 | Quate |
| 4,430,987 | A | 2/1984 | Heller |

(Continued)

FOREIGN PATENT DOCUMENTS

| | | |
|---|---|---|
| CN | 1883379 A | 12/2006 |
| CN | 106338473 A | 1/2017 |

(Continued)

OTHER PUBLICATIONS

Office Action from related U.S. Appl. No. 11/625,099, dated Nov. 1, 2010.

(Continued)

*Primary Examiner* — Lisa M Caputo
*Assistant Examiner* — Rose M Miller
(74) *Attorney, Agent, or Firm* — Sheila Martinez-Lemke; Weaver Austin Villeneuve & Sampson LLP

(57) ABSTRACT

Among the various aspects of the present disclosure is the provision of systems and methods of imaging using photoacoustic computed tomography.

16 Claims, 30 Drawing Sheets

(56) References Cited

U.S. PATENT DOCUMENTS

| | | |
|---|---|---|
| 4,462,255 A | 7/1984 | Guess et al. |
| 4,468,136 A | 8/1984 | Murphy et al. |
| 4,489,727 A | 12/1984 | Matsuo et al. |
| 4,546,771 A | 10/1985 | Eggleton et al. |
| 4,596,254 A | 6/1986 | Adrian et al. |
| 4,687,304 A | 8/1987 | Piller et al. |
| 4,740,081 A | 4/1988 | Martens et al. |
| 4,802,461 A | 2/1989 | Cho |
| 4,802,487 A | 2/1989 | Martin et al. |
| 4,809,703 A | 3/1989 | Ishikawa et al. |
| 4,850,363 A | 7/1989 | Yanagawa |
| 4,860,758 A | 8/1989 | Yanagawa et al. |
| 4,869,256 A | 9/1989 | Kanno et al. |
| 4,872,758 A | 10/1989 | Miyazaki et al. |
| 4,921,333 A | 5/1990 | Brody et al. |
| 4,929,951 A | 5/1990 | Small |
| 4,995,396 A | 2/1991 | Inaba et al. |
| 5,070,455 A | 12/1991 | Singer et al. |
| 5,083,549 A | 1/1992 | Cho et al. |
| 5,107,844 A | 4/1992 | Kami et al. |
| 5,115,814 A | 5/1992 | Griffith et al. |
| 5,125,410 A | 6/1992 | Misono et al. |
| 5,140,463 A | 8/1992 | Yoo et al. |
| 5,170,793 A | 12/1992 | Takano et al. |
| 5,194,723 A | 3/1993 | Cates et al. |
| 5,207,672 A | 5/1993 | Roth et al. |
| 5,227,912 A | 7/1993 | Ho et al. |
| 5,305,759 A | 4/1994 | Kaneko et al. |
| 5,321,501 A | 6/1994 | Swanson et al. |
| 5,329,817 A | 7/1994 | Garlick et al. |
| 5,331,466 A | 7/1994 | Van Saarloos |
| 5,345,938 A | 9/1994 | Nishiki et al. |
| 5,373,845 A | 12/1994 | Gardineer et al. |
| 5,414,623 A | 5/1995 | Lu et al. |
| 5,445,155 A | 8/1995 | Sieben |
| 5,465,722 A | 11/1995 | Fort et al. |
| 5,546,187 A | 8/1996 | Pepper et al. |
| 5,546,947 A | 8/1996 | Yagami et al. |
| 5,546,948 A | 8/1996 | Hamm et al. |
| 5,606,975 A | 3/1997 | Liang et al. |
| 5,615,675 A | 4/1997 | O'Donnell et al. |
| 5,635,784 A | 6/1997 | Seale |
| 5,651,366 A | 7/1997 | Liang et al. |
| 5,713,356 A | 2/1998 | Kruger |
| 5,718,231 A | 2/1998 | Dewhurst et al. |
| 5,781,294 A | 7/1998 | Nakato et al. |
| 5,836,872 A | 11/1998 | Kenet et al. |
| 5,840,023 A | 11/1998 | Oraevsky et al. |
| 5,860,934 A | 1/1999 | Sarvazyan |
| 5,913,234 A | 6/1999 | Julliard et al. |
| 5,971,998 A | 10/1999 | Russell et al. |
| 5,977,538 A | 11/1999 | Unger et al. |
| 5,991,697 A | 11/1999 | Nelson et al. |
| 6,055,097 A | 4/2000 | Lanni et al. |
| 6,102,857 A | 8/2000 | Kruger |
| 6,104,942 A | 8/2000 | Kruger |
| 6,108,576 A | 8/2000 | Alfano et al. |
| 6,111,645 A | 8/2000 | Tearney et al. |
| 6,134,003 A | 10/2000 | Tearney et al. |
| 6,216,025 B1 | 4/2001 | Kruger |
| 6,233,055 B1 | 5/2001 | Mandella et al. |
| 6,282,011 B1 | 8/2001 | Tearney et al. |
| 6,292,682 B1 | 9/2001 | Kruger |
| 6,309,352 B1 | 10/2001 | Oraevsky et al. |
| 6,341,036 B1 | 1/2002 | Tearney et al. |
| 6,379,325 B1 | 4/2002 | William et al. |
| 6,405,069 B1 | 6/2002 | Oraevsky et al. |
| 6,413,228 B1 | 7/2002 | Hung et al. |
| 6,421,164 B2 | 7/2002 | Tearney et al. |
| 6,432,067 B1 | 8/2002 | Martin et al. |
| 6,466,806 B1 | 10/2002 | Geva et al. |
| 6,485,413 B1 | 11/2002 | Boppart et al. |
| 6,490,470 B1 | 12/2002 | Kruger |
| 6,498,942 B1 | 12/2002 | Esenaliev et al. |
| 6,498,945 B1 | 12/2002 | Alfheim et al. |
| 6,501,551 B1 | 12/2002 | Tearney et al. |
| 6,545,264 B1 | 4/2003 | Stern |
| 6,564,087 B1 | 5/2003 | Pitris et al. |
| 6,567,688 B1 | 5/2003 | Wang |
| 6,590,830 B1 | 7/2003 | Garlick et al. |
| 6,626,834 B2 | 9/2003 | Dunnie et al. |
| 6,628,404 B1 | 9/2003 | Kelley et al. |
| 6,633,774 B2 | 10/2003 | Kruger |
| 6,654,630 B2 | 11/2003 | Zuluaga et al. |
| 6,658,279 B2 | 12/2003 | Swanson et al. |
| 6,694,173 B1 | 2/2004 | Bende et al. |
| 6,701,181 B2 | 3/2004 | Tang et al. |
| 6,751,490 B2 | 6/2004 | Esenaliev et al. |
| 6,764,450 B2 | 7/2004 | Yock |
| 6,831,781 B2 | 12/2004 | Tearney et al. |
| 6,833,540 B2 | 12/2004 | MacKenzie et al. |
| 6,839,496 B1 | 1/2005 | Mills et al. |
| 6,846,288 B2 | 1/2005 | Nagar et al. |
| 6,853,446 B1 | 2/2005 | Almogy et al. |
| 6,877,894 B2 | 4/2005 | Vona et al. |
| 6,937,886 B2 | 8/2005 | Zavislan |
| 6,956,650 B2 | 10/2005 | Boas et al. |
| 7,072,045 B2 | 7/2006 | Chen et al. |
| 7,198,778 B2 | 4/2007 | Achilefu et al. |
| 7,231,243 B2 | 6/2007 | Tearney et al. |
| 7,245,789 B2 | 7/2007 | Bates et al. |
| 7,266,407 B2 | 9/2007 | Li et al. |
| 7,322,972 B2 | 1/2008 | Viator et al. |
| 7,357,029 B2 | 4/2008 | Falk |
| 7,382,949 B2 | 6/2008 | Bouma et al. |
| 7,541,602 B2 | 6/2009 | Metzger et al. |
| 7,610,080 B1 | 10/2009 | Winchester, Jr. et al. |
| 7,917,312 B2 | 3/2011 | Wang et al. |
| 8,016,419 B2 | 9/2011 | Zhang et al. |
| 8,025,406 B2 | 9/2011 | Zhang et al. |
| 8,143,605 B2 | 3/2012 | Metzger et al. |
| 8,397,573 B2 | 3/2013 | Kobayashi |
| 8,416,421 B2 | 4/2013 | Wang et al. |
| 8,454,512 B2 | 6/2013 | Wang et al. |
| 8,891,088 B2 | 11/2014 | Goldschmidt et al. |
| 8,997,572 B2 | 4/2015 | Wang et al. |
| 9,086,365 B2 | 7/2015 | Wang et al. |
| 9,096,365 B2 | 8/2015 | Kim |
| 9,220,415 B2 | 12/2015 | Mandelis et al. |
| 9,226,666 B2 | 1/2016 | Wang et al. |
| 9,234,841 B2 | 1/2016 | Wang et al. |
| 9,335,605 B2 | 5/2016 | Wang et al. |
| 9,528,966 B2 | 12/2016 | Wang et al. |
| 9,554,738 B1 * | 1/2017 | Gulati .................. A61B 5/0075 |
| 9,618,445 B2 | 4/2017 | Sun et al. |
| 10,285,595 B2 | 5/2019 | Zalev et al. |
| 10,359,400 B2 | 7/2019 | Wang et al. |
| 10,433,733 B2 | 10/2019 | Wang et al. |
| 10,448,850 B2 | 10/2019 | Wang et al. |
| 11,020,006 B2 | 6/2021 | Wang et al. |
| 11,029,287 B2 | 6/2021 | Wang et al. |
| 11,135,375 B2 | 10/2021 | Brady et al. |
| 11,137,375 B2 | 10/2021 | Wang et al. |
| 11,369,280 B2 | 6/2022 | Wang et al. |
| 11,530,979 B2 | 12/2022 | Wang et al. |
| 11,592,652 B2 | 2/2023 | Wang et al. |
| 11,672,426 B2 | 6/2023 | Wang et al. |
| 2001/0052979 A1 | 12/2001 | Treado et al. |
| 2002/0093637 A1 | 7/2002 | Yuan et al. |
| 2002/0173780 A1 | 11/2002 | Altshuler et al. |
| 2002/0176092 A1 | 11/2002 | Deck |
| 2003/0097066 A1 | 5/2003 | Shelby et al. |
| 2003/0160957 A1 | 8/2003 | Oldham et al. |
| 2003/0160967 A1 | 8/2003 | Houston et al. |
| 2004/0030255 A1 | 2/2004 | Alfano et al. |
| 2004/0039379 A1 | 2/2004 | Viator et al. |
| 2004/0082070 A1 | 4/2004 | Jones et al. |
| 2004/0254474 A1 | 12/2004 | Seibel et al. |
| 2005/0015002 A1 | 1/2005 | Dixon et al. |
| 2005/0028482 A1 | 2/2005 | Cable et al. |
| 2005/0085725 A1 | 4/2005 | Nagar et al. |
| 2005/0143664 A1 | 6/2005 | Chen et al. |
| 2005/0154313 A1 | 7/2005 | Desilets et al. |
| 2005/0168749 A1 | 8/2005 | Ye et al. |

(56) References Cited

U.S. PATENT DOCUMENTS

| | | |
|---|---|---|
| 2005/0217381 A1 | 10/2005 | Falk |
| 2005/0234315 A1 | 10/2005 | Mayevsky et al. |
| 2005/0277824 A1 | 12/2005 | Aubry et al. |
| 2006/0055936 A1 | 3/2006 | Yun et al. |
| 2006/0058614 A1 | 3/2006 | Tsujita |
| 2006/0078196 A1* | 4/2006 | Sumanaweera ..... G01S 15/8993 128/916 |
| 2006/0122516 A1 | 6/2006 | Schmidt et al. |
| 2006/0181791 A1 | 8/2006 | Van Beek et al. |
| 2006/0184042 A1 | 8/2006 | Wang et al. |
| 2006/0235299 A1 | 10/2006 | Martinelli |
| 2006/0247510 A1 | 11/2006 | Wiemker et al. |
| 2006/0264717 A1 | 11/2006 | Pesach et al. |
| 2007/0075063 A1 | 4/2007 | Wilbanks et al. |
| 2007/0088206 A1 | 4/2007 | Peyman et al. |
| 2007/0093702 A1 | 4/2007 | Yu et al. |
| 2007/0213590 A1 | 9/2007 | Squicciarini |
| 2007/0213618 A1 | 9/2007 | Li et al. |
| 2007/0213693 A1 | 9/2007 | Plunkett |
| 2007/0282200 A1 | 12/2007 | Johnson et al. |
| 2007/0299341 A1 | 12/2007 | Wang et al. |
| 2008/0029711 A1 | 2/2008 | Viellerobe et al. |
| 2008/0037367 A1 | 2/2008 | Gross et al. |
| 2008/0088838 A1 | 4/2008 | Raicu et al. |
| 2008/0123083 A1 | 5/2008 | Wang et al. |
| 2008/0173093 A1 | 7/2008 | Wang et al. |
| 2008/0230717 A1 | 9/2008 | Ashkenazi et al. |
| 2009/0051900 A1 | 2/2009 | Moon et al. |
| 2009/0054763 A1 | 2/2009 | Wang et al. |
| 2009/0088631 A1 | 4/2009 | Dietz et al. |
| 2009/0116518 A1 | 5/2009 | Patel et al. |
| 2009/0138215 A1 | 5/2009 | Wang et al. |
| 2009/0185191 A1 | 7/2009 | Boppart et al. |
| 2009/0227997 A1 | 9/2009 | Wang et al. |
| 2010/0053618 A1 | 3/2010 | Nakajima et al. |
| 2010/0079768 A1 | 4/2010 | Wang et al. |
| 2010/0134793 A1 | 6/2010 | Krishnamachari et al. |
| 2010/0245766 A1 | 9/2010 | Zhang et al. |
| 2010/0245769 A1 | 9/2010 | Zhang et al. |
| 2010/0245770 A1 | 9/2010 | Zhang et al. |
| 2010/0249562 A1 | 9/2010 | Zhang et al. |
| 2010/0268042 A1 | 10/2010 | Wang et al. |
| 2010/0285518 A1 | 11/2010 | Viator et al. |
| 2010/0309466 A1 | 12/2010 | Lucassen et al. |
| 2010/0322497 A1 | 12/2010 | Dempsey et al. |
| 2011/0071402 A1 | 3/2011 | Masumura |
| 2011/0122416 A1 | 5/2011 | Yang et al. |
| 2011/0201914 A1 | 8/2011 | Wang et al. |
| 2011/0251515 A1 | 10/2011 | Leuthardt et al. |
| 2011/0275890 A1 | 11/2011 | Wang et al. |
| 2011/0282181 A1 | 11/2011 | Wang et al. |
| 2011/0282192 A1 | 11/2011 | Axelrod et al. |
| 2012/0065490 A1 | 3/2012 | Zharov et al. |
| 2012/0070817 A1 | 3/2012 | Wang et al. |
| 2012/0074294 A1 | 3/2012 | Streuber et al. |
| 2012/0118052 A1 | 5/2012 | O'Donnell et al. |
| 2012/0204648 A1 | 8/2012 | Wang et al. |
| 2012/0275262 A1 | 11/2012 | Song et al. |
| 2012/0307250 A1 | 12/2012 | Wang |
| 2013/0151188 A1 | 6/2013 | Rokni et al. |
| 2013/0199299 A1 | 8/2013 | Wang et al. |
| 2013/0218002 A1 | 8/2013 | Kiraly |
| 2013/0245406 A1 | 9/2013 | Wang et al. |
| 2014/0009808 A1 | 1/2014 | Wang et al. |
| 2014/0029829 A1 | 1/2014 | Jiang et al. |
| 2014/0142404 A1 | 5/2014 | Wang et al. |
| 2014/0356897 A1 | 12/2014 | Wang et al. |
| 2015/0005613 A1 | 1/2015 | Kim et al. |
| 2015/0178959 A1 | 6/2015 | Huang et al. |
| 2015/0185187 A1 | 7/2015 | Wang et al. |
| 2015/0245771 A1 | 9/2015 | Wang et al. |
| 2015/0272444 A1 | 10/2015 | Maslov et al. |
| 2015/0272446 A1 | 10/2015 | Wang et al. |
| 2015/0316510 A1 | 11/2015 | Fukushima et al. |
| 2016/0081558 A1 | 3/2016 | Wang et al. |
| 2016/0235305 A1 | 8/2016 | Wang et al. |
| 2016/0242651 A1 | 8/2016 | Wang et al. |
| 2016/0249812 A1 | 9/2016 | Wang et al. |
| 2016/0262628 A1 | 9/2016 | Wang et al. |
| 2016/0305914 A1 | 10/2016 | Wang et al. |
| 2016/0310083 A1 | 10/2016 | Wang et al. |
| 2016/0345886 A1 | 12/2016 | Wang et al. |
| 2017/0065182 A1 | 3/2017 | Wang et al. |
| 2017/0105636 A1 | 4/2017 | Wang et al. |
| 2017/0367586 A9 | 12/2017 | Wang et al. |
| 2018/0020920 A1 | 1/2018 | Ermilov et al. |
| 2018/0088041 A1 | 3/2018 | Zhang et al. |
| 2018/0132728 A1 | 5/2018 | Wang et al. |
| 2018/0177407 A1 | 6/2018 | Hashimoto et al. |
| 2019/0008444 A1 | 1/2019 | Wang et al. |
| 2019/0125583 A1 | 5/2019 | Wang et al. |
| 2019/0227038 A1 | 7/2019 | Wang et al. |
| 2019/0307334 A1 | 10/2019 | Wang et al. |
| 2019/0343758 A1 | 11/2019 | Wang et al. |
| 2020/0056986 A1* | 2/2020 | Wang ................ G01N 21/1702 |
| 2020/0073103 A1 | 3/2020 | Wang et al. |
| 2020/0268253 A1 | 8/2020 | Wang et al. |
| 2020/0275846 A1 | 9/2020 | Wang et al. |
| 2020/0397523 A1* | 12/2020 | Gao ....................... A61B 90/36 |
| 2021/0010976 A1 | 1/2021 | Wang et al. |
| 2021/0321874 A1 | 10/2021 | Wang et al. |
| 2021/0333241 A1 | 10/2021 | Wang et al. |
| 2023/0055979 A1 | 2/2023 | Wang et al. |

FOREIGN PATENT DOCUMENTS

| | | | |
|---|---|---|---|
| EP | 0012262 A1 | 6/1980 | |
| EP | 0919180 A1 | 6/1999 | |
| EP | 1493380 A1 | 1/2005 | |
| EP | 2749208 A1 * | 7/2014 | ........... A61B 5/0035 |
| EP | 3521808 A1 * | 8/2019 | ........... A61B 5/0095 |
| JP | 05-126725 A | 5/1993 | |
| JP | 2000/292416 A | 10/2000 | |
| JP | 4060615 B2 * | 3/2008 | ........... A61B 8/0883 |
| JP | 2009/068977 A | 4/2009 | |
| JP | 2010/017426 A | 1/2010 | |
| JP | 2010/040161 A | 2/2010 | |
| JP | 2012/143384 A | 8/2012 | |
| JP | 2013244122 A | 12/2013 | |
| JP | 2014124242 A | 7/2014 | |
| JP | 2014/224806 A | 12/2014 | |
| JP | 2016-101260 A | 6/2016 | |
| JP | 6086718 B2 | 3/2017 | |
| JP | 6390516 B2 * | 9/2018 | ............. A61B 8/469 |
| KR | 100946550 B1 | 3/2010 | |
| KR | 20160091059 A | 8/2016 | |
| KR | 2017-0006470 A | 1/2017 | |
| WO | WO-9633656 A1 * | 10/1996 | ............. G01S 15/58 |
| WO | WO2006/111929 A1 | 10/2006 | |
| WO | WO2007/088709 A1 | 8/2007 | |
| WO | WO2007/148239 A2 | 12/2007 | |
| WO | WO2008/062354 A1 | 5/2008 | |
| WO | WO2008/100386 A2 | 8/2008 | |
| WO | WO2009/055705 A2 | 4/2009 | |
| WO | WO-2009154298 A1 | 12/2009 | |
| WO | WO2010/048258 A1 | 4/2010 | |
| WO | WO2010/080991 A2 | 7/2010 | |
| WO | WO2011/060101 A2 | 5/2011 | |
| WO | WO2011/091360 A2 | 7/2011 | |
| WO | WO2011/127428 A2 | 10/2011 | |
| WO | WO2012/035472 A1 | 3/2012 | |
| WO | WO-2012133295 A1 | 10/2012 | |
| WO | WO2013/086293 A1 | 6/2013 | |
| WO | WO2015/118881 A1 | 8/2015 | |
| WO | WO-2016081321 A2 * | 5/2016 | ........... A61B 8/0841 |
| WO | WO2018/102446 A2 | 6/2018 | |
| WO | WO-2018102467 A1 | 6/2018 | |

(56) References Cited

FOREIGN PATENT DOCUMENTS

WO    WO-2018116963 A1 * 6/2018 ........... A61B 5/0035
WO    WO2018/209046 A1    11/2018

OTHER PUBLICATIONS

Final Office Action from related U.S. Appl. No. 11/625,099, dated Apr. 20, 2010.
Office Action from related U.S. Appl. No. 12/254,643, dated Aug. 6, 2010.
Notice of Allowance from related U.S. Appl. No. 12/254,643, dated Nov. 22, 2010.
Office Action from related U.S. Appl. No. 12/568,069, dated Dec. 21, 2012.
Office Action from related U.S. Appl. No. 12/568,069, dated Mar. 29, 2012.
Final Office Action from related U.S. Appl. No. 12/568,069, dated Sep. 18, 2012.
Notice of Allowance from related U.S. Appl. No. 12/568,069, dated Feb. 22, 2013.
Office Action from related U.S. Appl. No. 12/739,589, dated Jul. 19, 2012.
Notice of Allowance from related U.S. Appl. No. 12/739,589, dated Feb. 5, 2013.
Office Action from related U.S. Appl. No. 13/125,522, dated Jan. 22, 2013.
Final Office Action from related U.S. Appl. No. 13/125,522, dated May 23, 2013.
Office Action from related U.S. Appl. No. 13/125,522, dated Jul. 17, 2014.
Final Office Action from related U.S. Appl. No. 13/125,522, dated Oct. 29, 2014.
Office Action dated Aug. 26, 2015 issued in U.S. Appl. No. 13/125,522.
Final Office Action dated Mar. 3, 2016 issued in U.S. Appl. No. 13/125,522.
Notice of Allowance dated Sep. 19, 2016 issued in U.S. Appl. No. 13/125,522.
Office Action from related U.S. Appl. No. 13/143,832, dated Apr. 18, 2014.
Office Action from related U.S. Appl. No. 13/450,793, dated Jun. 5, 2013.
Final Office Action from related U.S. Appl. No. 13/450,793, dated Nov. 22, 2013.
Office Action from related U.S. Appl. No. 13/450,793, dated Mar. 24, 2014.
Office Action from related U.S. Appl. No. 13/450,793, dated Aug. 1, 2014.
Office Action from related U.S. Appl. No. 13/574,994, dated Mar. 17, 2014.
Final Office Action from related U.S. Appl. No. 13/574,994, dated Aug. 26, 2014.
Notice of Allowance dated Nov. 17, 2015 from U.S. Appl. No. 13/574,994.
Office Action dated Jan. 20, 2015, from U.S. Appl. No. 14/026,577.
Final Office Action dated Sep. 30, 2015, from U.S. Appl. No. 14/026,577.
Notice of Allowance dated Jan. 5, 2016, from U.S. Appl. No. 14/026,577.
Office Action dated Nov. 13, 2017, from U.S. Appl. No. 15/148,685.
Final Office Action dated Sep. 24, 2018, from U.S. Appl. No. 15/148,685.
Notice of Allowance dated May 16, 2019, from U.S. Appl. No. 15/148,685.
Office Action from related U.S. Appl. No. 13/637,897, dated Aug. 1, 2014.
Office Action from related U.S. Appl. No. 14/164,117, dated Dec. 11, 2015.
Office Action dated Dec. 13, 2019 issued in U.S. Appl. No. 15/037,468.
Notice of Allowance dated Mar. 23, 2020 issued in U.S. Appl. No. 15/037,468.
Notice of Allowance dated Oct. 28, 2020 issued in U.S. Appl. No. 15/037,468.
Office Action dated Oct. 3, 2018 issued in U.S. Appl. No. 14/436,581.
Amendment and Request for Continued Examination dated Nov. 25, 2019 in U.S. Appl. No. 14/436,581.
Final Office Action dated May 24, 2019 issued in U.S. Appl. No. 14/436,581.
Office Action dated Apr. 3, 2020 issued in U.S. Appl. No. 14/436,581.
Office Action dated Jun. 20, 2014 issued in U.S. Appl. No. 13/369,558.
Notice of Allowance dated Jul. 29, 2014 issued in U.S. Appl. No. 13/369,558.
Notice of Allowance dated Dec. 5, 2014 issued in U.S. Appl. No. 13/369,558.
Office Action dated Apr. 21, 2017 issued in U.S. Appl. No. 14/639,676.
Final Office Action dated Nov. 15, 2017 issued in U.S. Appl. No. 14/639,676.
Office Action dated May 31, 2018 issued in U.S. Appl. No. 14/639,676.
Notice of Allowance dated Dec. 12, 2018 issued in U.S. Appl. No. 14/639,676.
Office Action dated Feb. 28, 2020 issued in U.S. Appl. No. 16/372,597.
Office Action dated Aug. 19, 2019 issued in U.S. Appl. No. 16/372,597.
Office Action dated Oct. 8, 2020 issued in U.S. Appl. No. 16/372,597.
The International Search Report and Written Opinion dated Mar. 27, 2014 issued in Application No. PCT/US2013/065594.
The International Search Report and the Written Opinion of the International Searching Authority, or the Declaration, for PCT/US2009/061435, dated Mar. 29, 2010, 6 pages.
The International Search Report and the Written Opinion of the International Searching Authority, dated Sep. 22, 2011, from related application No. PCT/US2011/022253, 6 pgs.
International Search Report of International Application No. PCT/US2014/066437, dated Feb. 26, 2015, 3 pages.
Partial European Search Report issued for European Application No. 17159220.7, dated Aug. 23, 2017 (9 pages).
International Search Report and Written Opinion dated Apr. 22, 2009, from Application No. PCT/US2008/081167 (7 pages).
International Search Report and Written Opinion from Application Serial No. PCT/US2010/020488, dated Aug. 31, 2010 (10 pages).
International Search Report and Written Opinion from Application Serial No. PCT/US2011/031823, dated Dec. 26, 2011 (8 pages).
International Search Report and Written Opinion from Application Serial No. PCT1US2012/068403, dated Mar. 19, 2013 (10 pages).
Extended European Search Report from European Application Serial No. 08842292.8, dated Dec. 17, 2013 (8 pages).
Final Office Action from related Japanese Patent Application No. JP 2010-531281 , dated Mar. 11, 2014, (5 pages).
International Search Report and Written Opinion dated Dec. 2, 2019, issued in Application No. PCT/US2019/046574.
International Search Report and Written Opinion dated Dec. 23, 2019, issued in Application No. PCT/US2019/049594.
International Search Report and Written Opinion dated Aug. 31, 2020, issued in Application No. PCT/US2020/019368.
International Search Report and Written Opinion dated Oct. 14, 2020, issued in Application No. PCT/US2020/07174.
International Search Report dated Aug. 9, 2018 issued in Application No. PCT/US2018/032007.
Written Opinion of the International Searching Authority dated Aug. 9, 2018 issued in Application No. PCT/US2018/032007.
International Preliminary Report on Patentability dated Nov. 12, 2019 issued in PCT/US2018/032007.
Abdelmohsen, et al., "Micro- and nano-motors for biomedical applications," J. Mater. Chem. B 2, (2014) pp. 2395-2408.
Al, et al., "Spectral-domain optical coherence tomography: Removal of autocorrelation using an optical switch," Applied Physics Letters, (Mar. 15, 2006), 88(11): pp. 111115-1-111115-3. <doi:10.1063/1.2186520>.

(56) References Cited

OTHER PUBLICATIONS

Allen, et al. "Pulsed Near-Infrared Laser Diode Excitation System for Biomedical Photoacoustic Imaging," Optics Letters, Optical Society of America, USA., vol. 31 , No. 23, Dec. 1, 2006, pp. 3462-3464.
Alomair, et al., "In vivo high angular resolution diffusion-weighted imaging of mouse brain at 16.4 Tesla," PloS One 10, Jun. 25, 2015, e0130133, pp. 1-17.
Aubry J.-F. , et al. , "Experimental demonstration of noninvasive transskull adaptive focusing based on prior computed tomography scans," J. Acoust. Soc. Am. 113(1), 84-93 (2003). (Year: 2003).
Baheiraei, et al., "Investigation of magnesium incorporation within gelatin/calcium phosphate nanocomposite scaffold for bone tissue engineering," Int. J. Appl. Ceram. Technol. 12, (2015) pp. 245-253.
Baker, M. J. et al., "Using Fourier transform IR spectroscopy to analyze biological materials," Nat. Protoc. 9, 1771-1791 (2014).
Bansil, et al., "The biology of mucus: Composition, synthesis and organization" Adv. Drug Deliv. Rev. 124, (2018) pp. 3-15.
Beaven, G. H. & Holiday, E. R., "Ultraviolet absorption spectra of proteins and amino acids," Adv. Protein Chem 7, 319-386 (1952).
Bell, A.G., "On the Production and Reproduction of Sound by Light," American Journal of Sciences, Oct. 1880, pp. 305-324, Third Series, vol. XX, USA.
Bellinger, et al., "Oral, ultra-long-lasting drug delivery: Application toward malaria elimination goals" Sci Transl. Med. 8(365), Nov. 16, 2016, 365ra157, pp. 1-25. <doi:10.1126/scitranslmed.aag2374>.
Bioucas-Dias, J.M. And Figueiredo, M.A.T. "A new TwIST: two-step iterative shrinkage/thresholding algorithms for image restoration," IEEE Trans. Image Process. 16, 2992-3004 (Dec. 2007).
Brenner, et al., "Computed Tomography—An Increasing Source of Radiation Exposure" N. Engl. J. Med 357;22, Nov. 29, 2007, pp. 2277-2284.
Calasso et al., "Photoacoustic Point Source," Physical Review Letters, vol. 86, No. 16, Apr. 16, 2001, pp. 3550-3553.
Cannata et al., "Development of a 35-MHz Piezo-Composite Ultrasound Array for Medical Imaging," IEE Transactions on Ultrasonics, Ferroelectrics, and Frequency Control, 53(1): pp. 224-236 (2006).
Celli, J. P., et al., "Helicobacter pylori moves through mucus by reducing mucin viscoelasticity," Proc. Natl. Acad. Sci. U. S. A. 106, (2009) pp. 14321-14326.
Chan, et al., "New opportunities in micro- and macro-attenuated total reflection infrared spectroscopic imaging: spatial resolution and sampling versatility," Appl. Spectrosc. 57, 381-389 (2003).
Cheng, J.-X. Et al., "Vibrational spectroscopic imaging ofliving systems: an emerging platform for biology and medicine," Science, vol. 350 aaa8870, No. 6264, Nov. 27, 2015, pp. 1054-1063.
Cheong, et al., "A review of the optical properties of biological tissues," IEEE J. Quantum Electronics, 26(12): pp. 2166-2185 (1980).
Chourasia, et al., "Design and Development of Multiparticulate System for Targeted Drug Delivery to Colon," Drug Delivery, 11:3, (2004) pp. 201-207.
Cox, B., Beard, P., "Photoacoustic tomography with a single detector in a reverberant cavity" J. Acoust. Soc. Am. 125, 1426 (Mar. 2009).
Cui, Y., et al. "Transferring-conjugated magnetic silica PLGA nanoparticles loaded with doxorubicin and paclitaxel for brain glioma treatment," Biomaterials 34, (2013) pp. 8511-8520.
De Boer, et al., "Improved signal-to-noise ratio in spectral-domain compared with time-domain optical coherence tomography" Optics Letters, vol. 28, No. 21, Nov. 1, 2003, pp. 2067-2069.
D'Andrea, et al., "Time-resolved optical imaging through turbid media using a fast data acquisition system based on a gated CCD camera" Journal of Physics D: Applied Physics, vol. 36, No. 14, Jul. 1, 2003, pp. 1675-1681.
Danielli, et al., "Label-free photoacoustic nanoscopy," Journal of Biomedical Optics, vol. 19, No. 8, Aug. 2014, pp. 086006-1-086006-10.
Dazzi, A. et al., "AFM-IR: technology and applications in nanoscale infrared spectroscopy and chemical imaging," Chem. Rev. 117, 5146-5173 (2017).
Dazzi, A., et al., "Local infrared microspectroscopy with subwavelength spatial resolution with an atomic force microscope tip used as a photothermal sensor," Optics Letters, vol. 30, No. 18, Sep. 15, 2005, pp. 2388-2390.
de Avila, et al., "Micromotor-enabled active drug delivery for in vivo treatment of stomach infection" Nat. Commun. 8: 272, (2017) pp. 1-9.
de Zerda, et al., "Family of enhanced photoacoustic imaging agents for high-sensitivity and multiplexing studies in living mice," ACS Nano 6(6), Jun. 26, 2012, pp. 4694-4701.
Diebold, et al., "Photoacoustic Monopole Radiation in One, Two and Three Dimensions," Physical Review Letters, Figs. 1 and 2, vol .67, No. 24, Dec. 9, 1991 , pp. 3384-3387.
Diebold, et al., "Photoacoustic Signature of Particulate Matter: Optical Production of 9 Acoustic Monopole Radiation," Science New Series, Oct. 5, 1990, pp. 101-104, vol. 250, No. 4977, pp. 101-104.
Diem, M. et al., "Molecular pathology via IR and Raman spectral imaging." Journal of Biophotonics, vol. 6, No. 11-12 (2013) pp. 855-886. <doi:10.1002/jbio.201300131>.
Diem, M., et al., "A decade of vibrational micro-spectroscopy of human cells and tissue (1994-2004)†," Analyst, Oct. 2004, vol. 129, No. 10, pp. 880-885. <doi:10.1039/b408952a>.
Draeger, C., Fink, M., "One-channel time reversal of elastic waves in a chaotic 2D-silicon cavity," Phys. Rev. Lett. 79, 407-410 (Jul. 21, 1997).
Dunn, et al., "Transport-based image reconstruction in turbid media with small source—detector separations," Optics Letters, vol. 25, No. 24, Dec. 15, 2000, pp. 1777-1779.
Eghtedari, et al., "High Sensitivity of in Vivo Detection of Gold Nanorods Using a Laser Optoacoustic Imaging System," Nano Letters, vol. 7, No. 7, 2007, pp. 1914-1918.
Ermilov et al., "Laser optoacoustic imaging system for detection of breast cancer," Journal of Biomedical Optics, vol. 14 No. 2, pp. 24007-024007-14 (2009).
Erpelding et al., "Sentinel Lymph Nodes in the Rat: Noninvasive Photoacoustic and US Imaging with a Clinical US System," Radiology, 256(1): 102-110 (2010).
Evans, et al., "Coherent Anti-Stokes Raman Scattering Microscopy: Chemical Imaging for Biology and Medicine," Annual Review of Analytical Chemistry 1, (2008), pp. 883-909.
Fan, et al., "Development of a Laser Photothermoacoustic Frequency-Swept System for Subsurface Imaging: Theory and Experiment," J. Acoust. Soc. Am., vol. 116 (6), Dec. 2004, pp. 3523-3533.
Fan, et al., "Sub-Cellular Resolution Delivery of a Cytokine via Precisely Manipulated Nanowires" Nat. Nanotechnol. 5(7), Jul. 2010, 545-551. <doi:10.1038/nnano.2010.104>.
Fang, et al., "Photoacoustic Doppler effect from flowing small light-absorbing particles," Physical Review Letters 99(18) 184501-(1-4) (Nov. 2, 2007).
Fercher, et al., "Measurement of Intraocular Distances by Backscattering Spectral Interferometry," Optics Communications, 1995, vol. 117, pp. 43-48.
Fernandez, D. C., Bhargava, R., Hewitt, S. M. & Levin, I. W., "Infrared spectroscopic imaging for histopathologic recognition," Nat. Biotechnol. 23, 469-474 (2005).
Foster, et al., "Advances in ultrasound biomicroscopy" Ultrasound in Medicine & Biology, vol. 26, No. 1, Jan. 2000, pp. 1-27.
Fujita, K., et al., "Confocal multipoint multiphoton excitation microscope with microlens and pinhole arrays," Opt. Comm. 174, 7-12 (Jan. 15, 2000).
Furstenberg, et. al., "Chemical Imaging using Infrared Photothermal Microspectroscopy," In Proceedings of SPIE Defense, Security, and Sensing (eds Druy, M.A. & Crocombe, R. A.) 837411 (SPIE, 2012).
Gaihre, et al., "Gelatin-coated magnetic iron oxide nanoparticles as carrier system: Drug loading and in vitro drug release study," Int. J. Pharm. 365, (2009) pp. 180-189.

(56) References Cited

OTHER PUBLICATIONS

Gao, et al., "Single-shot compressed ultrafast photography at one hundred billion frames per second," Nature 516(7529) 74-77 (Dec. 4, 2014).

Gao, et al., "A review of snapshot multidimensional optical imaging: measuring photon tags in parallel" Phys Rep. 616, Feb. 29, 2016, pp. 1-37. <doi:10.1016/j.physrep.2015.12.004>.

Gao, et al., "Artificial micromotors in the mouse's stomach: A step toward in vivo use of synthetic motors,"ACS Nano 9, (2015) pp. 117-123.

Gibson, et al., "Recent advances in diffuse optical imaging" Physics in Medicine and Biology 50, 2005, pp. R1-R43, Inslilule of Physics Publishing, UK.

Gong, L. et al., "Breaking the diffraction limit by saturation in stimulated-Raman-scattering microscopy: a theoretical study," Phys. Rev. A 90, 13818 (2014).

Griffiths, P., "Fourier transform infrared spectrometry," Science 21, 297-302 (1983).

Guggenheim, et al., "Ultrasensitive planoconcave optical microresonators for ultrasound sensing", Nat. Photon. 11, 714-721 (2017).

Guittet C, et al., "In vivo high-frequency ultrasonic characterization of human dermis" IEEE Transactions on Bio-medical Engineering. Jun. 1999;46(6):740-746. <doi:10.1109/10.764950>.

Guo, et al., "Calibration-free absolute quantification of optical absorption coefficients using acoustic spectra in three-dimensional photoacoustic microscopy of biological tissue" Opt Lett. 2010 ; 35(12): 2067-2069. <doi:10.1364/OL.35.002067>.

Guo, et al., "CsxWO3 nanorods coated with polyelectrolyte multilayers as a multifunctional nanomaterial for bimodal imaging-guided photothermal/photodynamic cancer treatment," Adv. Mater. 29, 1604157 (2017).

Haas, J. et al., "Advances in Mid-Infrared Spectroscopy for Chemical Analysis," Annu. Rev. Anal. Chem. 9 (2016) pp. 45-68.

Hai, et al., "Near-infrared optical-resolution photoacoustic microscopy", Opt. Lett. 39, 5192-5195 (Sep. 1, 2014).

Hai, et al., "High-throughput, label-free, single-cell photoacoustic microscopy of intratumoral metabolic heterogeneity," Nature Biomedical Engineering 3(5) 381-391 (May 2019).

Hebden et al., "Enhanced time-resolved imaging with a diffusion model of photon transport" Optics Letters, vol. 19, No. 5, 1994, pp. 311-313.

Hee, et al., "Femtosecond transillumination tomography in thick tissues" Optics Letters, vol. 18, No. 13, 1993, pp. 1107-1109.

Hillman, et al., "Laminar optical tomography: demonstration of millimeter-scale depth-resolved imaging in turbid media," Optics Letters, vol. 29, No. 14, Jul. 15, 2004, pp. 1650-1652.

Hoelen, et al., "Three Dimensional Photoacoustic Imaging of Blood Vessels in Tissue" Optics Letters, 1998, pp. 648-650, vol. 23, No. 8, Optical Society of America, USA.

Hong, et al., "Simple Method to Produce Janus Colloidal Particles in Large Quantity" Langmuir 22, (2006) pp. 9495-9499.

Hu, C., et al., "Soft Micro- and Nanorobotics," Annu. Rev. Control. Robot. Auton. Syst. 1, (2018) pp. 53-75.

Hu, W., et al., "Small-scale soft-bodied robot with multimodal locomotion," Nature 554, 81-85, (2018).

Hu, S. et al., "Three-dimensional optical-resolution photoacoustic microscopy," Journal of Visualized Experiments 51 (2011).

Hu, S., et al., "Label-free Photoacoustic Ophthalmic Angiography" Optics Letters, 35(1), Jan. 1, 2010, pp. 1-3.

Huang, et al., "Aberration correction for transcranial photoacoustic tomography of primates employing adjunct image data," Journal of Biomedical Optics, vol. 17, No. 6, Jun. 2012, pp. 066016-1 to 066016-8.

Huang, et al., "Optical Coherence Tomography," Science, New Series, vol. 254, No. 5035, Nov. 22, 1991 , pp. 1178-1181.

Huber, et al., "Three-Dimensional and C-Mode 6 OCT Imaging with a Compact, Frequency Swept Laser Source at 1300 nn" Optics Express, vol. 13, No. 26, Dec. 26, 2005, pp. 10523-10526.

Imai, T. et al., "High-throughput ultraviolet photoacoustic microscopy with multifocal excitation," Journal of Biomedical Optics 23(3), 036007 (Mar. 15, 2018).

Ing, R. K., Quieffin, N., Catheline, S., Fink, M., "In solid localization of finger impacts using acoustic time-reversal process," Appl. Phys. Lett. 87, 204104 (Nov. 14, 2005).

Ji, M. et al., "Detection of human brain tumor infiltration with quantitative stimulated Raman scattering microscopy," Sci. Transl. Med 7, 309ra163 (2015).

Ji, T. et al. "Preparation, Characterization, and Application of Au-Shell/Polystyrene Beads and Au-hell/Magnetic Beads" Adv. Mater. 13(16), Aug. 2001, pp. 1253-1256.

Karamata, et al., "Multiple Scattering in Optical Coherence Tomography I Investigation and Modeling" Journal of Optical Society of America, vol. 22, No. 7 (2005) pp. 1369-1379.

Karamata, et al., "Multiple scattering in optical coherence tomography. II. Experimental and theoretical investigation of cross talk in wide-field optical coherence tomography" J. Opt. Soc. Am. A/vol. 22, No. 7/Jul. 2005, pp. 1380-1388.

Karshalev, E. et al., "Micromotor Pills as a Dynamic Oral Delivery Platform" American Chemical Society Nano, 2018, vol. 12, No. 8, pp. 8397-8405 <DOI: 10.1021/acsnano.8b03760>.

Kim, C. et al., "In vivo molecular photoacoustic tomography of melanomas targeted by bio-conjugated gold nanocages" ACS Nano, 2010; 4(8), pp. 4559-4564. <doi:10.1021/nn100736c>.

Kirch, J., et al., "Optical tweezers reveal relationship between microstructure and nanoparticle penetration of pulmonary mucus," Proc. Natl. Acad. Sci. 109, (2012) pp. 18355-18360.

Knoll, B. & Keilmann, F., "Near-field probing of vibrational absorption for chemical microscopy," Nature 399, 134-137 (1999).

Kole, M. R., et al., "Discrete frequency infrared microspectroscopy and imaging with a tunable quantum cascade laser," Anal. Chem. 84, 10366-10372 (2012).

Kolkman, et al., "In Vivo Photoacoustic Imaging of Blood Vessels Using an Extreme-Narrow Aperture Sensor" IEEE Journal of Selected Topics in Quantum Electronics, vol. 9, No. 2, Mar./Apr. 2003, pp. 343-346.

Koziolek, et al., "Navigating the human gastrointestinal tract for oral drug delivery: Uncharted waters and new frontiers," Adv. Drug Delivery Rev. 101, (2016) pp. 75-88.

Kruger et al., "Photoacoustic Ultrasound (PAUS)-Reconstruction Tomography" Med. Phys., Oct. 1995, vol. 22 (10) Am. Assoc. Phys. Med., USA, pp. 1605-1609.

Kruger, et al., "Thermoacoustic computed tomography—technical considerations" Medical Physics, 26(9): 1832-1837 (1999).

Kruger et al., "Thermoacoustic computed tomography using a conventional linear transducer array," Medical Physics, 30(5): 856-860 (2003).

Kruger, et al., "Thermoacoustic Molecular Imaging of Small Animals," Molecular Imaging, 2(2): 113-123 (2003).

Kruger, et al., "Thermoacoustic CT: imaging principles," Proc. SPIE 3916, (2000) pp. 150-160.

Kruger, et al., "Breast Cancer in Vivo: Contrast Enhancement with Thermoacoustic CT at 434 MHz-Feasibility Study," Radiology, 216(1): 279-283 (2000).

Ku and Wang, "Scanning thermoacoustic tomography in biological tissue." Medical physics 27.5 (2000): 1195-1202.

Ku and Wang, "Scanning microwave-induced thermoacoustic tomography: Signal, resolution, and contrast," Medical Physics, 28(1): 4-10 (2001).

Ku, G. et al., "Multiple-bandwidth photoacoustic tomography," Physics in Medicine & Biology, 49(7): 1329-1338 (2004).

Ku and Wang, "Deeply penetrating photoacoustic tomography in biological tissues enhanced with an optical contrast agent," Optics Letters, 30(5): 507-509 (2005).

Ku, et al., "Imaging of tumor angiogenesis in rat brains in vivo by photoacoustic tomography," Applied Optics, 44(5): 770-775 (2005).

Ku, et al., "Thermoacoustic and Photoacoustic Tomography of Thick Biological Tissues Toward Breast Imaging," Technology in Cancer Research & Treatment, 4(5): 559-566 (2005).

Kunitz, M., "Crystalline desoxyribonuclease; isolation and general properties; spectrophotometric method for the measurement of

(56) References Cited

OTHER PUBLICATIONS desoxyribonuclease activity," The Journal General Physiology, vol. 33, Mar. 20, 1950, pp. 349-362. <URL:http://doi.org./10.1085/jgp.33.4.349>.

Kuppusami, S. et al., "Parylene Coatings in Medical Devices and Implants: A Review" Universal Journal of Biomedical Engineering, 2015, vol. 3, No. 2, pp. 9-14 <DOI: 10.13189/ujbe.2015.030201>.

Lai, S. et al., "Mucus-penetrating nanoparticles for drug and gene delivery to mucosal tissues," Adv. Drug Deliv. Rev. 61(2), Feb. 27, 2009, pp. 158-171. <doi:10.1016/j.addr.2008.11.002>.

Lai, P. et al., "Photoacoustically guided wavefront shaping for enhanced optical focusing in scattering media," Nature Photonics 9 126-132 (Jan. 19, 2015).

Lai, P. et al., "Dependence of optical scattering from Intralipid in gelatin-gel based tissue-mimicking phantoms on mixing temperature and time" Journal of Biomedical Optics, vol. 19, No. 3, Mar. 2014, pp. 035002-1-035002-6.

Larina, et al., Real-time optoacoustic monitoring of temperature in tissues: Journal of Physics D: Applied Physics, vol. 38, (2005) pp. 2633-2639.

Lasch, et al., "FT-IR spectroscopic investigations of single cells on the subcellular level," Vibr. Spectrosc. 28, 147-157 (2002).

Laser Institute of America, "American National Standard for the safe use of lasers," American National Standard Institute (ANSI Z136.1-2007 Revision of ANSI Z136.1-2000).

Leal, et al., "Physicochemical properties of mucus and their impact on transmucosal drug delivery," Int. J. Pharm. 532, (2017) pp. 555-572.

Lewis, E. N. et al., "Fourier transform spectroscopic imaging using an infrared focal-Plane array detector," Anal. Chem. 67, 3377-3381 (1995).

Leitgeb, et al., "Performance of fourier domain vs. time domain optical coherence tomography," Optical Express, vol. 11, No. 8, Apr. 21, 2003, pp. 889-894.

Li, et al., "An Enteric Micromotor Can Selectively Position and Spontaneously Propel in the Gastrointestinal Tract," ACS Nano. 10(10), Oct. 25, 2016, pp. 9536-9542. <doi:10.1021/acsnano.6b04795>.

Li, et al., "Autonomous Collision-Free Navigation of Microvehicles in Complex and Dynamically Changing Environments" ACS Nano, 11, (2017) pp. 9268-9275.

Li, G., et al., "Reflection-mode multifocal optical-resolution photoacoustic microscopy," J. Biomed. Opt. 18, 030501 (Feb. 12, 2013).

Li, J. et al., "Micromotors Spontaneously Neutralize Gastric Acid for pH-Responsive Payload Release" Angewandte Chemie International Edition, vol. 56, No. 8, 2017, pp. 2156-2161. <DOI: 10.1002/anie.201611774>.

Li, L., et al., "Small near-infrared photochromic protein for photoacoustic multi-contrast imaging and detection of protein interactions in vivo," Nature Communications 9(1) 2734 (Jul. 16, 2018).

Li, et al., "Single-impulse panoramic photoacoustic computed tomography of small-animal whole-body dynamics at high spatiotemporal resolution," Nat Biomed Eng. 1(5) May 2017, pp. 1-11. <doi:10.1038/s41551-017-0071>.

Li, L.., et al., "Simultaneous Molecular and Hypoxia Imaging of Brain Tumors in Vivo Using Spectroscopic Photoacoustic Tomography," Proceedings of the IEEE, 96(3): 481-489 (2008).

Li, J. et al., "Micro/Nanorobots for Biomedicine: Delivery, Surgery, Sensing, and Detoxification" Sci Robot, 2(4), Mar. 15, 2017, pp. 1-20. <doi:10.1126/scirobotics.aam6431>.

Li, Y. et al., "Multifocal photoacoustic microscopy through an ergodic relay (Conference Presentation)", Proc. SPIE 10878, Photons Plus Ultrasound: Imaging and Sensing 2019, 108781C, presented Feb. 4, 2019, published Mar. 4, 2019, https://doi.org/10.1117/12.2513502.

Li, et al., "Optical Coherence Computed Tomography," Applied Physics Letters, vol. 91, American Institute of Physics, 2007, pp. 141107-1-141107-3.

Li, et al., "Snapshot photoacoustic topography through an ergodic relay for high-throughput imaging of optical absorption," Nature Photonics 14(3) (2020) pp. 164-170. <URL:https://doi.org/10.1038/s41566-019-0576-2>.

Li, Z., et al., "Super-resolution far-field infrared imaging by photothermal heterodyne imaging," The Journal of Physical Chemistry B, vol. 121 (2017) pp. 8838-8846.

Li, Z., et al., "Super-resolution imaging with mid-IR photothermal microscopy on the single particle level," in Proceedings of SPIE Physical Chemistry of Interfaces and Nano-materials XIV, vol. 9549, Aug. 20, 2015, pp. 9549121-1-954912-8.

Liang, et al., "Single-shot real-time femtosecond imaging of temporal focusing," Light-Science & Applications 7(1) 42 (Aug. 8, 2018).

Liang, et al., "Single-shot real-time video recording of a photonic Mach cone induced by a scattered light pulse," Science Advances 3(1) e1601814 (Jan. 20, 2017).

Liang, et al., "Single-shot ultrafast optical imaging," Optica 5(9) 1113-1127 (Sep. 2018).

Lin, et al., "Single-breath-hold photoacoustic computed tomography of the breast," Nature Communications 9(1) 2352 (Jun. 15, 2018).

Liu, et al., "Optical focusing deep inside dynamic scattering media with near-infrared time-reversed ultrasonically encoded (TRUE) light," Nature Communications 6 5409 (Jan. 5, 2015).

Liu, et al., "Label-free cell nuclear imaging by Grüneisen relaxation photoacoustic microscopy" Opt Lett. Feb. 15, 2018; 43(4), (2018) pp. 947-950.

Lovell, et al., "Porphysome nanovesicles generated by porphyrin bilayers for use as multimodal biophotonic contrast agents," Nature Materials 10(4) 324-32 (Mar. 20, 2011).

Lu, F., et al., "Tip-enhanced infrared nanospectroscopy via molecular expansion force detection," Nat. Photon. 8, 307-312 (2014).

Lu, F.-K. et al., "Label-free DNA imaging in vivo with stimulated Raman scattering microscopy," Proc. Natl Acad Sci. USA 112, 11624-11629 (2015).

Ma, et al., "Time-reversed adapted-perturbation (TRAP) optical focusing onto dynamic objects inside scattering media," Nature Photonics 8(12) 931-936 (Nov. 2, 2014).

Manohar, et al., "Initial results of in vivo non-invasive cancer imaging in the human breast using near-infrared photoacoustics," Optics Express, 15(19): 12277-12285 (2007).

Maslov, et al., "In vivo dark-field reflection-mode photoacoustic microscopy," Optics Letters 30(6), Mar. 15, 2005, pp. 625-627.

Maslov, et al., "Optical-resolution photoacoustic microcropy for in vivo imaging of single capillaries," Optical Letters, 33(9): 929-931 (2008).

Maslov, et al., "Photoacoustic Imaging of biological tissue with Intensity-Modulated Continuous-Wave Laser" Journal of Biomedical Optics, 2008, pp. 024006 1-5, vol. 13(2), SPIE, USA.

Medina-Sanchez, et al., "Medical microbots need better imaging and control," Nature 545, (2017) pp. 406-408.

Michaelian, Kirk H. "Photoacoustic IR spectroscopy: instrumentation, applications and data analysis" John Wiley & Sons; Dec 1, 2010. <Preface Only>.

Miller, et al., "Synchrotron-based biological microspectroscopy: From the mid-infrared through the far-infrared regimes," Journal of Biological Physics 29, 219-230 (2003).

Mishra et al., "Development and comparison of the DTM, the DOM and the FVM formulations for the short-pulse laser transport through a participating medium" International Journal of Heat and Mass Transfer, vol. 49 (2006) pp. 1820-1832.

Montaldo, et al., "Building three-dimensional images using time-reversal chaotic cavity", IEEE Trans. Ultrason. Ferroelectr. Freq. Control 52, pp. 1489-1497 (2005).

Morgner et al., "Spectroscopic optical coherence tomography," Optics Letters, vol. 25, No. 2, Jan. 15, 2000, pp. 111-113.

Murray et al., "High-Sensitivity Laser-Based Acoustic Microscopy Using a Modulated Excitation Source," Applied Physics Letters, vol. 85, No. 14, American Institute of Physics, USA., Oct. 4, 2004, pp. 2974-2976.

(56) References Cited

OTHER PUBLICATIONS

Nakajima, et al., "Three-dimensional analysis and classification of arteries in the skin and subcutaneous adipofascial tissue by computer graphics imaging," Plastic and Reconstructive Surgery, 102(3): 748-760 (1998).
Nasiriavanaki, et al., "High-resolution photoacoustic tomography of resting-state functional connectivity in the mouse brain," Proceedings of the National Academy of Sciences 111(1) 21-26 (Jan. 7, 2014).
Nasse, M. J. et al., "High-resolution Fourier-transform infrared chemical imaging with multiple synchrotron beams," Nat. Methods 8, 413-416 (2011).
Nelson et al., "Imaging Glioblastoma Multiforme," The Cancer Journal vol. 9, No. 2, Mar./Apr. 2003, pp. 134-145.
Niederhauser et al., "Combined Ultrasound and Optoacoustic System for Real-Time High-Contrast Vascular imaging in Vivo," IEEE Transactions on MedicalImaging, 24(4): 436-440 (2005).
Nowak, D. et al., "Nanoscale chemical imaging by photoinduced force microscopy," Sci. Adv. 2, Mar. 25, 2016, e1501571, pp. 1-9.
Ntziachristos, V., "Going deeper than microscopy: the optical imaging frontier in biology" Nature Methods vol. 7, No. 8, Aug. 2010, pp. 603-614.
Oraevsky et al., "Optoacoustic Tomography," Biomedical Photonics Handbook, 2003, chapter 34: pp. 931-964, CRC Press LLC, USA.
Oraevsky et al., "Ultimate Sensitivity of Time-Resolved Opto-Acoustic Detection," Biomedical Optoacoustics, 2000, pp. 228-239, vol. 3916, SPIE, USA.
Oraevsky et al., "Laser Optoacoustic Tomography of Layered Tissues: Signal Processing" Proceedings of SPIE, 2979: 59-70 (1997).
Oraevsky et al., "Laser opto-acoustic imaging of the breast: Detection of cancer angiogenesis" Proceedings of SPIE, 3597: 352-363 (1999).
Patel, et al., "Pulsed optoacoustic spectroscopy of condensed matter," Rev. Mod. Phys., vol. 53 (1981) pp. 517-550.
Paxton, et al., "Catalytic nanomotors: Autonomous movement of striped nanorods," J. Am. Chem. Soc. 126, 13424-13431 (2004).
Petrov, et al., "Optoacoustic, Noninvasive, Real-Time, Continuous Monitoring of Cerebral Blood Oxygenation: An in Vivo Study in Sheep" Anesthesiology, vol. 102, No. 1, Jan. 2005, pp. 69-75.
Potter, et al., "Capillary diameter and geometry in cardiac and skeletal muscle studied by means of corrosion casts" Microvascular Research, 25(1): 68-84 (1983).
Prati, et al., "New advances in the application of FTIR microscopy and spectroscopy for the characterization of artistic materials," Accounts of Chemical Research, vol. 43, (2010) pp. 792-801.
Prevedel, et al., "Simultaneous whole-animal 3D imaging of neuronal activity using light-field microscopy," Nat. Methods 11, 727-730 (Jul. 2014).
Quickenden, et al., "The ultraviolet absorption spectrum ofliquid water," J Chem. Phys. 72, 4416-4428 (1980).
Razansky, et al., "Multispectral opto-acoustic tomography of deep-seated fluorescent proteins in vivo," Nature Photonics 3, (2009) pp. 412-417.
Robert et al., "Fabrication of Focused Poly (Vinylidene Fluoride-Trifluoroethylene) P19 (VDF-TrFE) Copolymer 40-50 MHz Ultrasound Transducers on Curved Surfaces," Journal of Applied Physics, vol. 96, No. 1. Jul. 1, 2004, pp. 252-256.
Rockley, M.G., "Fourier-transformed infrared photoacoustic spectroscopy of polystyrene film," Chem. Phys. Lett. 68, 455-456 (1979).
Rosenblum, et al., "Progress and challenges towards targeted delivery of cancer therapeutics" Nat. Commun. 9, (2018) 1410, pp. 1-12.
Saager et al., "Direct characterization and removal of interfering absorption trends in two-layer turbid media" J. Opt. Soc. Am. A, vol. 22, No. 9, Sep. 2005, pp. 1874-1882.
Sanchez, et al., "Chemically powered micro- and nanomotors," Angew. Chem. Int. Ed. 54, (2015) pp. 1414-1444.
Sakadzic, et al., "Correlation transfer and diffusion of ultrasound-modulated multiply scattered light," Physical Review Letters 96(16) 163902-(1-4) (Apr. 28, 2006).
Savateeva, et al., "Noninvasive detection and staging or oral cancer in vivo with confocal opto-acoustic tomography" Biomedical Optoacoustics, vol. 3916, International Society for Optics and Photonics 2000, pp. 55-66.
Schambach, et al., "Application of micro-CT in small animal imaging" Methods, vol. 50, No. 1, Jan. 2010, pp. 2-13.
Schmidt, et al., "A 32-Channel Time Resolved Instrument for Medical Optical Tomography" Review of Scientific Instruments, vol. 71, No. 1, Jan. 2000, pp. 256-265.
Scholte, Rick et al. "On Spatial Sampling and Aliasing in Acoustic Imaging", In 12th Intern. Congress on Sound and Vibration, (Jul. 2005) Lisbon, Portugal.
Schroeter, et al., "Spontaneous slow hemodynamic oscillations are impaired in cerebral microangiopathy," Journal of Cerebral Blood Flow & Metabolism (2005) 25, pp. 1675-1684.
Servant, et al., "Controlled in Vivo Swimming of a Swarm of Bacteria-Like Microrobotic Flagella" Advanced Materials 27, (2015) pp. 2981-2988.
Sezer, et al., "Review of magnesium-based biomaterials and their applications," J. Magnesium Alloys 6, (2018) pp. 23-43.
Sethuraman et al., "Development of a combined intravascular ultrasound and photoacoustic imaging system" Proceedings of SPIE, 6086: 60860F.1-60860F.10 (2006).
Sethuraman et al., "Intravascular photoacoustic imaging of atherosclerotic plaques: Ex vivo study using a rabbit model of atherosclerosis" Proceedings of SPIE, 6437: 643729.1-643729.9 (2007).
Shah, J. et al, "Photoacoustic imaging and temperature measurement for photothermal cancer therapy," Journal of Biomedical Optics, vol. 13, No. 3, (May/Jun. 2008) pp. 034024-1-034024-9.
Sheth, et al., "Columnar Specificity of Microvascular Oxygenation and Volume Responses: Implications for Functional Brain Mapping," The Journal of Neuroscience, vol. 24, No. 3, Jan. 21, 2004, pp. 634-641.
Shi, J., et al., "High-resolution, high-contrast mid-infrared imaging of fresh biological samples with ultraviolet-localized photoacoustic microscopy," Nature Photonics 13 609-615 (May 2019).
Shmueli, et al., "Low Frequency Fluctuations in the Cardiac Rate as a Source of Variance in the Resting-State fMRI BOLD Signal," Neuroimage, vol. 38, No. 2, Nov. 1 2007, pp. 306-320.
Silva, et al., "Toward Label-Free Super-Resolution Microscopy," ACS Photon. 3, 79-86 (2016).
Sim, et al., "In vivo Microscopic Photoacoustic Spectroscopy for Non-Invasive Glucose Monitoring Invulnerable to Skin Secretion Products," Sci. Rep. 8, 1059 (2018).
Siphanto et al., "Imaging of Small Vessels Using Photoacoustics: an in Vivo Study," Lasers in Surgery and Medicince, vol. 35, Wiley-Liss, Inc., Netherlands, Dec. 20, 2004, pp. 354-362.
Sitti, M., "Miniature soft robots-road to the clinic," Nat. Rev. Mater, 3, (2018) pp. 74-75.
Smith, et al., "Beyond C, H, O, and Ni analysis of the elemental composition of U.S. FDA approved drug architectures," J. Med. Chem. 57, pp. 9764-9773 (2014).
Sommer, A. J., et al., "Attenuated total internal reflection infrared mapping microspectroscopy using an imaging microscope," Appl. Spectrosc. 55, 252-256 (2001).
Song, et al., "Fast 3-D dark-field reflection-mode photoacoustic microscopy in vivo with a 30-MHz ultrasound linear array" Journal of Biomedical Optics, 13(5): 054028.1-054028.5 (2008).
Song et al., "Multi-focal optical-resolution photoacoustic microscopy in vivo." NIH Public Access Author Manuscript, May 13, 2011. pp. 1-7.
Song, et al., "Section-illumination photoacoustic microscopy for dynamic 3D imaging of microcirculation in vivo" Optics Letters, 35(9): 1482-1484 (2010).
Soppimath, et al., "Microspheres as floating drug-delivery systems to increase gastric retention of drugs" Drug Metab. Rev. 33, (2001) pp. 149-160.
Steinbrink, et al., "Illuminating the BOLD signal: combined fMRI-fNIRS studies" Magnetic Resonance Imaging, vol. 24, No. 4, May 2006, pp. 495-505.

(56) References Cited

OTHER PUBLICATIONS

Stern, MD., "In vivo evaluation of microcirculation by coherent light scattering," Nature, 254(5495): 56-58 (1975).
Tay, et al., "Magnetic Particle Imaging Guided Heating in Vivo using Gradient Fields for Arbitrary Localization of Magnetic Hyperthermia Therapy" ACS Nano. 12(4), Apr. 24, 2018, pp. 3699-3713. <doi:10.1021/acsnano.8b00893>.
Tam, A. C., "Applications of photoacoustic sensing techniques," Reviews of Modern Physics, vol. 58, No. 2, Apr. 1986, pp. 381-431.
Tearney, et al., "Scanning single-mode fiber optic catheter-endoscope for optical coherence tomography" Optics Letters, 21(7): 543-545 (1996).
Tran, et al., "In vivo endoscopic optical coherence tomography by use of a rotational microelectromechanical system probe" Optics Letters, 29(11): 1236-1238 (2004).
Treeby B. E., et al., "Photoacoustic tomography in absorbing acoustic media using time reversal," Inverse Probl. (2010) 26(11), pp. 1-20.
Tu, et al., "Self-propelled supramolecular nanomotors with temperature-responsive speed regulation," Nat. Chem. 9, 480 (2016).
Van Essen, et al., "An Integrated Software Suite for Surface-based Analyses of Cerebral Cortex" Journal of the American Medical Informatics Association, vol. 8, No. 5, Sep./Oct. 2001, pp. 443-459.
Velasco, E., "Ultrafast Camera Takes 1 Trillion Frames Per Second of Transparent Objects and Phenomena" [Webpage] Caltech, California Institute of Technology, Jan. 17, 2020, pp. 1-2. <URL:https://www.eurekalert.org/pub_releases/2020-01/ciot-uct012120.php>.
Viator et al., "Design testing of an endoscopic photoacoustic probe for determination of treatment depth after photodynamic therapy" Proceedings of SPIE in Biomedical Optoacoustics II, 4256: 16-27 (2001).
Vilela, et al., "Medical imaging for the tracking of micromotors," ACS Nano 12, (2018) pp. 1220-1227.
Wang, et al., "Ballistic 2-D Imaging Through Scattering Walls Using an Ultrafast Optical Kerr Gale," Science, vol. 253, Aug. 16, 1991, pp. 769-771.
Wang, et al., "Biomedical Optics, Principles and Imaging," Wiley-Interscience, A John Wiley & Sons, Inc., (2007) p. 7.
Wang, et al., "Fabrication of micro/nanoscale motors" Chem. Rev. 115, (2015) pp. 8704-8735.
Wang, B. et al., "Recent progress on micro- and nano-robots: towards in vivo tracking and localization" Quantitative Imaging in Medicine and Surgery, 2018, vol. 8, No. 5, pp. 461-479. <DOI: 10.21037/qims.2018.06.07>.
Wang, L. et al., "Grueneisen relaxation photoacoustic microscopy," Physical Review Letters 113 174301 (Oct. 24, 2014).
Wang, L. V & Yao, J., "A practical guide to photoacoustic tomography in the life sciences," Nat. Methods 13, 627-638 (Jul. 28, 2016).
Wang, L. V., "Multiscale photoacoustic microscopy and computed tomography," Nat. Photon. 3, 503-509 (Aug. 29, 2009).
Wang, L. V.; "Mechanisms of ultrasonic modulation of multiply scattered coherent light: an analytic model," Physical Review Letters 87(4) 043903-(1-4) (Jul. 23, 2001).
Wang, L. V.; "Prospects of photoacoustic tomography," Medical Physics 35(12), Nov. 19, 2008, pp. 5758-5767.
Wang, L., et al., "Single-cell label-free photoacoustic flowoxigraphy in vivo," Proceedings of the National Academy of Sciences 110(15) 5759-5764 (Apr. 9, 2013).
Wang, L., et al., "Ultrasonically encoded photoacoustic flowgraphy in biological tissue," Physical Review Letters 111(20), 204301 (Nov. 15, 2013).
Wang, L.V., Hu, S. "Photoacoustic Tomography: in vivo imaging from organelles to organs," Science 335, 1458-1462 (Mar. 23, 2012).
Wang, X. D., et al., "Noninvasive laser-induced photoacoustic tomography for structural and functional in vivo imaging of the brain," Nature Biotechnology 21(7) 803-806 (Jul. 2003).
Wang, et al., "MCML—Monte Carlo modeling of light transport in multi-layered tissues" Computer Methods and Programs in Biomedicine, vol. 47, No. 2, Jul. 1995, pp. 131-146.
Wang et al., "Three-dimensional laser-induced photoacoustic tomography of mouse brain with the skin and skull intact," Optics Letters, 28(19): 1739-1741 (2003).
Wang et al., "Noninvasive photoacoustic angiography of animal brains in vivo with near-infrared light and an optical contrast agent" Optics Letters, 29(7): 730-732 (2004).
Wang, et al., "Intravascular Photoacoustic Imaging" IEEE J Quantum Electronics, 16(3): 588-599 (2010).
Wang, et al., "Nano/microscale motors: biomedical opportunities and challenges," ACS Nano 6, (2012) pp. 5745-5751.
Wetzel, et al., "Imaging molecular chemistry with infrared microscopy," Science, New Series, vol. 285, No. 5431, Aug. 20, 1999, pp. 1224-1225.
Wong, T. et al., "Fast label-free multilayered histology-like imaging of human breast cancer by photoacoustic microscopy," Sci. Adv. 3, 1602168 (May 17, 2017).
Wong, T. et al., "Label-free automated three-dimensional imaging of whole organ by microtomy-assisted photoacoustic microscopy," Nat. Comm. 8, (Nov. 9, 2017).
Wu, Z., et al., "A microrobotic system guided by photoacoustic computed tomography for targeted navigation in intestines in vivo," Science Robotics 4(32) eaax0613 (Jul. 24, 2019).
Wu, D., et al., "In vivo Mapping of Macroscopic Neuronal Projections in the Mouse Hippocampus using High-resolution Diffusion MRI," Neuroimage 125, Jan. 15, 2016, pp. 84-93.
Xia, J., et al., "Photoacoustic tomography: principles and advances," Electromagn. Waves 147, 1 (2014; available in PMC Jan. 30, 2015).
Xia, J., et al., "Wide-field two-dimensional multifocal optical-resolution photoacoustic-computed microscopy," Opt. Lett. 38(24), Dec. 15, 2013, pp. 5236-5239.
Xu, et al., "Photoacoustic Imaging in Biomedicine," Review of Scientific Instruments, American Institute of Physics, vol. 77 (2006) pp. 041101 1-22.
Xu, et al., "Rhesus monkey brain imaging through intact skull with thermoacoustic tomography," IEEE Trans. Ultrason. Ferroelectr. Freq. Control, vol. 53, No. 3, Mar. 2006, pp. 542-548.
Xu, M. H.; Wang, L. V.; "Time-domain reconstruction for thermoacoustic tomography in a spherical geometry," IEEE Transactions on Medical Imaging 21(7) 814-822 (Jul. 2002).
Xu, M. H.; Wang, L. V.; "Universal back-projection algorithm for photoacoustic computed tomography," Physical Review E 71(1) 016706-(1-7) (Jan. 19, 2005).
Xu, S., et al., "Thermal expansion of confined water," Langmuir 25, 5076-5083 (2009).
Xu, X. et al., "Time-reversed ultrasonically encoded optical focusing into scattering media," Nature Photonics 5(3) 154-157 (Jan. 16, 2011).
Xu, Y.; Wang, L. V.; "Time reversal and its application to tomography with diffracting sources," Physical Review Letters 92(3) 033902-(1-4) (Jan. 23, 2004).
Yadlowsky, et al., "Multiple scattering in optical coherence microscopy" Applied Optics, vol. 34, No. 25 (1995) pp. 5699-5707. <doi.org/10.1364/AO.34.005699>.
Yan, et al., "Multifunctional biohybrid magnetite microrobots for imaging-guided therapy" Yan et al., Sci. Robot. 2, eaaq1155, Nov. 22, 2017, pp. 1-14.
Yang, "Optical coherence and Doppler tomography for monitoring tissue changes induced by laser thermal therapy—An in vivo feasibility study" Review of Scientific Instruments, vol. 74, No. 1, Jan. 2003, p. 437-440.
Yang, J. M. et al., "Simultaneous functional photoacoustic and ultrasonic endoscopy of internal organs in vivo," Nature Medicine 18(8) 1297-1303 (Aug. 2012).
Yang, J., et al., "Motionless volumetric photoacoustic microscopy with spatially invariant resolution," Nature Communications 8(1) 780 (Oct. 3, 2017).
Yang, et al., "Novel biomedical imaging that combines intravascular ultrasound (IVUS) and optical coherence tomography (OCT)" IEEE International Ultrasonics Symposium, Beijing, China, Nov. 2-5, 2008, pp. 1769-1772.

(56) References Cited

OTHER PUBLICATIONS

Yang, et al., "Time-reversed ultrasonically encoded optical focusing using two ultrasonic transducers for improved ultrasonic axial resolution" Journal of Biomedical Optics 18(11), 110502 (Nov. 2013) pp. 110502-1-110502-4.
Yang, et al., "The grand challenges of science robotics," Science Robotics 3, Jan. 31, 2018, eaar7650, pp. 1-14.
Yang, J.M., et al., "Focusing light inside live tissue using reversibly switchable bacterial phytochrome as a genetically encoded photochromic guide star" Science Advances 5(12) (2019) pp. 1-9.
Yao, et al., "Monte Carlo simulation of an optical coherence tomography signal in homogeneous turbid media" Phys. Med. Biol. 44(9), Jul. 8, 1999, pp. 2307-2320.
Yao, et al., "Absolute photoacoustic thermometry in deep tissue," Opt. Lett. 38, 5228-5231 (2013).
Yao, et al., "In vivo label-free photoacoustic microscopy of cell nuclei by excitation of DNA and RNA," Opt. Lett. 35, 4139-4141 (2010).
Yao, et al., "Optimal ultraviolet wavelength for in vivo photoacoustic imaging of cell nuclei," J Biomed. Opt. 17, 056004 (2012).
Yao, et al., "Photoimprint photoacoustic microscopy for three-dimensional label-free sub-diffraction imaging," Physical Review Letters 112(1) 014302 (Jan. 10, 2014).
Yao, L. et al., "Multiscale photoacoustic tomography using reversibly switchable bacterial phytochrome as near-infrared photochromic probe," Nature Methods 13(1) 67-73 (Jan. 2016).
Yao, L. et al., "High-speed label-free functional photoacoustic microscopy of mouse brain in action," Nat. Methods 12(5), 407-410 (May 12, 2015).
Yao, L. et al., "Photoacoustic microscopy: superdepth, superresolution, and superb contrast", IEEE Pulse 6, 34-7 (May 13, 2015).
Yagoob, et al., "Methods and application areas of endoscopic optical coherence tomography" Journal of Biomedical Optics, 11(6): 063001. 1-063001.19 (2006).
Yavuz, M. S., et al., "Gold nanocages covered by smart polymers for controlled release with near-infrared light," Nature Materials 8(12) 935-939 (Nov. 1, 2009).
Yin, et al., "Agarose particle-templated porous bacterial cellulose and its application in cartilage growth in vitro" Acta Biomater. Jan. 12, 2015, pp. 129-138. <doi:10.1016/j.actbio.2014.10.019>.
Yodh et al., "Functional Imaging with Diffusing Light" Biomedical Photonics Handbook, 2003, Ch. 21 , pp. 45, CRC Press, Boca Raton.
Yodh, et al. "Spectroscopy and Imaging with Diffusing Light" Physics Today 48(3), Mar. 1995, pp. 34-40.
Zeff, et al., "Retinotopic mapping of adult human visual cortex with high-density diffuse optical tomography" PNAS, vol. 104, No. 29, Jul. 17, 2007, pp. 12169-12174.
Zemp, et al., "Realtime photoacoustic microscopy in vivo with a 30MHZ ultrasonic array transducer" Optics Express, 16(11): 7915-7928 (2008).
Zhang, C., et al., "Coherent Raman scattering microscopy in biology and medicine," Annu. Rev. Biomed. Eng. 17, 415-445 (2015).
Zhang, D. et al., "Depth-resolved mid-infrared photothermal imaging of living cells and organisms with submicrometer spatial resolution," Sci. Adv. 2, e1600521 (2016).
Zhang, H. F. et al., "Functional photoacoustic microscopy for high-resolution and noninvasive in vivo imaging," Nature Biotechnology 24(7) 848-851 (Jul. 2006).
Zhang, H. F. et al., "In vivo imaging of subcutaneous structures using functional photoacoustic microscopy," Nature Protocols 2(4) 797-804 (Apr. 5, 2007).
Zhang, et al., "Intrinsic Functional Relations Between Human Cerebral Cortex and Thalamus" Journal of Neurophysiology, vol. 100, No. 4, Oct. 2008, pp. 1740-1748.
Zharov, et al., "In vivo photoacoustic flow cytometry for monitor of circulating single cancer cells and contrast agents," Optics Letters, 31(24): 3623-3625 (2006).
Zou, et al., "BOLD responses to visual stimulation in survivors of childhood cancer" NeuroImage, vol. 24, No. 1, Jan. 1, 2005, pp. 61-69.
U.S. Appl. No. 16/946,496, filed Jun. 24, 2020, Gao et al.
U.S. Appl. No. 16/611,939, filed Nov. 8, 2019, Wang et al.
Arridge, et al., "Accelerated high-resolution photoacoustic tomography via compressed sensing," ArXiv Prepr. ArXiv160500133, 2016, pp. 8908-8940.
Cox, et al., "Artifact trapping during time reversal photoacoustic imaging for acoustically heterogeneous media," IEEE Trans. Med. Imaging, vol. 29, No. 2, (2010) pp. 387-396.
Deán-Ben, et al., "Functional optoacoustic neuro-tomography for scalable whole-brain monitoring of calcium indicators," Light Sci. Appl., vol. 5, No. 12, p. e16201, 2016, pp. 1-7.
Deén-Ben, et al., "Portable spherical array probe for volumetric real-time optoacoustic imaging at centimeter-scale depths," Opt. Express, vol. 21, No. 23, 2013, pp. 28062-28071.
Deserno, M., "How to generate equidistributed points on the surface of a sphere," Polym. Ed, p. 99, 2004, p.1.
Han, Y. et al., "Three-dimensional optoacoustic reconstruction using fast sparse representation," Opt. Lett., vol. 42, No. 5, (2017) pp. 979-982.
Han, et al., "Optoacoustic image reconstruction and system analysis for finite-aperture detectors under the wavelet-packet framework," J. Biomed. Opt., vol. 21, No. 1, Jan. 2016, pp. 016002-1-016002-9.
Huang, et al., "Full-wave iterative image reconstruction in photoacoustic tomography with acoustically inhomogeneous media," IEEE Trans. Med. Imaging, vol. 32, No. 6, Jun. 2013, pp. 1097-1110.
R. A. Kruger, et al., "Dedicated 3D photoacoustic breast imaging," Med. Phys., vol. 40, No. 11, 2013, pp. 113301-1-113301-8.
Maslov, et al., "Label-free automated three-dimensional imaging of whole organs by microtomy-assisted photoacoustic microscopy," Nature Communications 8(1) 1386 (2017), pp. 1-8.
Matthews, et al., "Parameterized Joint Reconstruction of the Initial Pressure and Sound Speed Distributions for Photoacoustic Computed Tomography," SIAM J. Imaging Sci., vol. 11, No. 2, (2018) pp. 1560-1588.
Matsumoto, et al., "Label-free photoacoustic imaging of human palmar vessels: a structural morphological analysis," Sci. Rep., vol. 8, No. 1, (2018) p. 786.
Mitsuhashi, et al., "A forward-adjoint operator pair based on the elastic wave equation for use in transcranial photoacoustic computed tomography," SIAM J. Imaging Sci., vol. 10, No. 4, 2017, pp. 2022-2048.
Mitsuhashi, et al., "Investigation of the far-field approximation for modeling a transducer's spatial impulse response in photoacoustic computed tomography," Photoacoustics, vol. 2, No. 1, 2014, pp. 21-32.
Ogunlade, et al., "In vivo three-dimensional photoacoustic imaging of the renal vasculature in preclinical rodent models," Am. J. Physiol.-Ren. Physiol., vol. 314, No. 6, (2018) pp. F1145-F1153.
Pramanik, M., "Improving tangential resolution with a modified delayand-sum reconstruction algorithm in photoacoustic and thermoacoustic tomography," Josa A, vol. 31, No. 3, (2014) pp. 621-627.
Schoeder, et al., "Optoacoustic image reconstruction: the full inverse problem with variable bases," Proc. R. Soc. A, vol. 474, No. 2219, (2018) pp. 1-20.
Treeby, et al., "k-Wave: MATLAB toolbox for the simulation and reconstruction of photoacoustic wave fields," J. Biomed. Opt., vol. 15, No. 2, Mar./Apr. 2010, pp. 021314.
Treeby, et al., "Advanced photoacoustic image reconstruction using the k-Wave toolbox," in Photons Plus Ultrasound: Imaging and Sensing 2016, 2016, vol. 9708, p. 97082P.
Tzoumas, et al., "Eigenspectra optoacoustic tomography achieves quantitative blood oxygenation imaging deep in tissues," Nat. Commun., vol. 7, 2016, pp. 1-10.
Wang et al., "Biomedical optics: principles and imaging," Section 12.5; Photoacoustic Tomography, John Wiley & Sons (2012) pp. 288-290.
Wang, K. et al., "Investigation of iterative image reconstruction in three-dimensional optoacoustic tomography," Phys. Med. Biol., vol. 57, No. 17, 2012, p. 5399-5423.

(56) References Cited

OTHER PUBLICATIONS

Xu, et al., "Exact frequency-domain reconstruction for thermoacoustic tomography-II: Cylindrical geometry," IEEE Trans. Med. Imaging, vol. 21, No. 7, (2002) pp. 829-833.

Zhou, et al., "Tutorial on photoacoustic tomography," J. Biomed. Opt., vol. 21, No. 6, Jun. 2016, pp. 061007-1-061007-14.

Duan, T. et al., "Hybrid Multi-wavelength Photoacoustic Imaging", 40th Annual International Conference of the IEEE Engineering in Medicine and Biology Society (EMBC), Jul. 18, 2018, pp. 4804-4807.

EP Office Action dated May 11, 2022, in Application No. EP19849860.2.

Extended European Search Report dated Apr. 22, 2022, in Application No. 19849860.2.

Extended European search report dated May 23, 2022, in Application No. EP19857631.6.

International Preliminary Report on Patentability dated Feb. 25, 2021, issued in Application No. PCT/US2019/046574.

International Preliminary Report on Patentability dated Jan. 6, 2022 in PCT Application No. PCT/US2020/070174.

International Preliminary Report on Patentability dated Mar. 18, 2021, issued in Application No. PCT/US2019/049594.

International Preliminary Report on Patentability dated May 19, 2022, in PCT Application No. PCT/US2020/059214.

International Preliminary Report on Patentability dated Sep. 2, 2021, issued in Application No. PCT/US2020/019368.

International Search Report and Written Opinion dated Mar. 2, 2021 issued in PCT/US2020/059214.

Li, Y. et al., "Multifocal Photoacoustic Microscopy Using a Single-element Ultrasonic Transducer Through an Ergodic Relay", Light: Science & Applications, Jul. 31, 2020, vol. 9, No. 135, pp. 1-7.

Notice of Allowance dated Feb. 2, 2021 issued in U.S. Appl. No. 16/372,597.

Notice of Allowance dated Jan. 26, 2021 issued in U.S. Appl. No. 14/436,581.

Notice of Allowance dated Jan. 5, 2022 issued in U.S. Appl. No. 16/540,936.

Notice of Allowance dated Jun. 23, 2021 issued in U.S. Appl. No. 15/037,468.

U.S. Notice of Allowance dated Oct. 19, 2022 in U.S. Appl. No. 16/560,680.

U.S. Notice of Allowance dated Sep. 7, 2022 in U.S. Appl. No. 16/611,939.

U.S. Corrected Notice of Allowance dated Nov. 14, 2022 in U.S. Appl. No. 16/540,936.

U.S. Corrected Notice of Allowance dated Oct. 26, 2022 in U.S. Appl. No. 16/560,680.

U.S. Corrected Notice of Allowance dated Apr. 27, 2022 in U.S. Appl. No. 16/540,936.

U.S. Corrected Notice of Allowance dated Jun. 2, 2022 In U.S. Appl. No. 16/806,796.

U.S. Ex Parte Quayle Action dated Dec. 13, 2021 in U.S. Appl. No. 16/611,939.

U.S. Final office Action dated Jan. 27, 2023 in U.S. Appl. No. 16/798,204.

U.S. Non Final Office Action dated Aug. 26, 2022 in U.S. Appl. No. 17/302,313.

U.S. Non-Final office Action dated Jan. 23, 2023 in U.S. Appl. No. 17/302,313.

U.S. Non-Final Office Action dated Mar. 20, 2023 in U.S. Appl. No. 17/302,041.

U.S. Non-Final Office Action dated May 2, 2022 in U.S. Appl. No. 16/798,204.

U.S. Notice of Allowance dated Apr. 19, 2022 in U.S. Appl. No. 16/540,936.

U.S. Notice of Allowance dated Aug. 5, 2022 in U.S. Appl. No. 16/540,936.

U.S. Notice of Allowance dated Dec. 22, 2022 in U.S. Appl. No. 16/611,939.

U.S. Notice of Allowance dated Feb. 23, 2022 in U.S. Appl. No. 16/806,796.

U.S. Notice of Allowance dated Jan. 26, 2023 in U.S. Appl. No. 16/560,680.

U.S. Office Action dated Apr. 7, 2022, in U.S. Appl. No. 16/560,680.

U.S. Requirement for Restriction dated Oct. 29, 2021 in U.S. Appl. No. 16/560,680.

U.S. Restriction Requirement dated Dec. 15, 2022 in U.S. Appl. No. 17/302,041.

White D.N., et al., "Effect of Skull in Degrading the Display of Echoencephalographic Band C Scans," The Journal of the Acoustical Society of America, Nov. 1968, vol. 44(5), pp. 1339-1345.

Xu et al., "Time Reversal Ultrasound Modulated Optical Tomography Using a BSO Phase Conjugate Mirror," poster presented at SIPE Conference 7177 on Jan. 26, 2009, 1 page.

Yao, J. et al., "Double-illumination Photoacoustic Microscopy", Optics Letters, Feb. 15, 2012, vol. 37, No. 4, pp. 659-661.

Bee-Dimmer, L., et al., "The Epidemiology of Chronic Venous Insufficiency and Varicose Veins," Annals of epidemiology, 2005, vol. 15(3), pp. 175-184.

Boas, D. A. and Dunn, A. K., "Laser speckle contrast imaging in biomedical optics," Journal of Biomedical Optics, (Jan./Feb. 2010), vol. 15, No. 1, p. 011109, 12 pages.

Cinotti, E., et al., "Quantification of Capillary Blood Cell Flow Using Reflectance Confocal Microscopy," Skin Research and Technology, 2014, vol. 20, pp. 373-378.

Demene, C. et al., Spatiotemporal clutter filtering of ultrafast ultrasound data highly increases Doppler and fUltrasound sensitivity, IEEE transactions on medical imaging, (Apr. 30, 2015), 34(11):2271-85.

Dong, J., et al., "Walled Vessel-mimicking Phantom for Ultrasound Imaging Using 3d Printing With a Water-soluble Filament: Design Principle, Fluid-structure Interaction (Fsi) Simulation, and Experimental Validation," Physics in medicine and biology, 2020, vol. 65(8).

Errico, C., et al., "Ultrafast Ultrasound Localization Microscopy for Deep Super-resolution Vascular Imaging," Nature, 2015, vol. 527(7579), pp. 499-502.

Farneback, G., et al., "Two-frame motion estimation based on polynomial expansion, in Scandinavian conference on Image analysis," 2003, pp. 363-370.

Fernandez-Colino, A., et al., "Advances in Engineering Venous Valves: The Pursuit of a Definite Solution for Chronic Venous Disease," Tissue engineering. Part B, Reviews, 2021, vol. 27(3), pp. 253-265.

Guo, Z., et al., "On the Speckle-free Nature of Photoacoustic Tomography," Medical Physics, 2009, vol. 36(9), pp. 4084-4088.

Hindelang, et al., "Enabling Precision Monitoring of Psoriasis Treatment by Optoacoustic Mesoscopy," Science Translational Medicine, 2022, vol. 14(644).

Hu P et al., "Location-Dependent Spatiotemporal Antialiasing in Photoacoustic Computed Tomography," IEEE Transactions on Medical Imaging, Apr. 2023, vol. 42(4), pp. 1210-1224.

Jaipan, P., et al., "Gelatin-based Hydrogels for Biomedical Applications," MRS Communications, 2017, vol. 7, pp. 416-426.https://doi.org/10.1557/mrc.2017.92.

Keys, A., et al., "The Oxygen Saturation of the Venous Blood in Normal Human Subjects,"American Journal of Physiology-Legacy Content, 1938, vol. 124(1), pp. 13-21.

Kinnunen, M., et al., "Effect of the Size and Shape of a Red Blood Cell On Elastic Light Scattering Properties At the Single-cell Level," Biomedical Optics Express, 2011, vol. 2(7), pp. 1-12.

Kothapalli, S., et al., "Simultaneous Transrectal Ultrasound and Photoacoustic Human Prostate Imaging," Science Translational Medicine, 2019, vol. 11 (507), pp. 1-12.

Lai P., et al., "Time-reversed Ultrasonically Encoded Optical Focusing in Biological Tissue," Journal of Biomedical Optics, 2012, vol. 17 (3), pp. 1-4.

Lee, Y., et al., "Automatic Dynamic Range Adjustment for Ultrasound B-mode Imaging," Ultrasonics, 2015, vol. 56, pp. 435-443.

Leitgeb, R., et al., "Doppler Optical Coherence Tomography," Progress in Retinal and Eye Research, 2014, vol. 41, pp. 26-43.

(56) References Cited

OTHER PUBLICATIONS

Lin, L., et al., "The Emerging Role of Photoacoustic Imaging in Clinical Oncology," Nature reviews. Clinical oncology, 2022, vol. 19(6), pp. 365-384.
Lurie, F., et al., "Mechanism of Venous Valve Closure and Role of the Valve in Circulation: a New Concept," Journal of vascular surgery, 2003, vol. 38(5), pp. 955-961.
Montaldo, et al., "Coherent Plane-Wave Compounding for Very High Frame Rate Ultrasonography and Transient Elastography," IEEE Trans. Ultrason. Ferroelectr. Freq. Control, vol. 56, No. 3, Mar. 2009, pp. 489-506.
Murray, C., et al., "The Physiological Principle of Minimum Work: I. The Vascular System and the Cost of Blood Volume," Proceedings of the National Academy of Sciences of the United States of America, 1926, vol. 12(3), pp. 207-214.
Na, S., et al., "Cross-ray Ultrasound Tomography and Photoacoustic Tomography of Cerebral Hemodynamics in Rodents," Advanced science, 2022, vol. 9(25).
Na, S., et al., "Massively Parallel Functional Photoacoustic Computed Tomography of the Human Brain," Nature Biomedical Engineering 2021, vol. 6(5), pp. 584-592.
Petrila, T., et al., "Basics of Fluid Mechanics and Introduction to Computational Fluid Dynamics," Springer Science & Business Media, 2004, vol. 3, pp. 1-512.
Qureshi, M., et al., "Quantitative Blood Flow Estimation in Vivo by Optical Speckle Image Velocimetry," 2021, Optica, vol. 8, p. 1326-1326.
Rajan, V., et al., "Review of Methodological Developments In Laser Doppler Flowmetry," Lasers in Medical Science, 2008, vol. 24(2), pp. 269-283.
Tanter, M., et al., "Ultrafast Imaging in Biomedical Ultrasound," IEEE, 2014, vol. 61 (1), pp. 102-119.
U.S. Final office Action dated Jun. 20, 2023 in U.S. Appl. No. 17/302,313.
U.S. Final Office Action dated Sep. 25, 2023, in U.S. Appl. No. 17/302,041.
U.S. Non-Final Office Action dated Aug. 14, 2023, in U.S. Appl. No. 16/798,204.
U.S. Non-Final Office Action dated Oct. 20, 2023, in U.S. Appl. No. 16/946,496.
U.S. Notice of Allowance dated Nov. 29, 2023 in U.S. Appl. No. 17/302,313.
U.S. Notice of Allowance dated Sep. 13, 2023 in U.S. Appl. No. 17/302,313.
U.S. Appl. No. 18/336,834, inventors Zhang et al., filed Jun. 16, 2023.
U.S. Appl. No. 18/450,597, inventors Hu P, et al., filed Aug. 16, 2023.
U.S Restriction requirement dated Aug. 9, 2023 in U.S. Appl. No. 16/946,496.
Wang, L., et al., "Biomedical optics: principles and imaging," 2012.
Wang, L., et al., "Tutorial on Photoacoustic Microscopy and Computed Tomography," IEEE Journal of Selected Topics in Quantum Electronics, 2008, vol. 14(1), pp. 171-179.
Wiedeman, M., et al., "Dimensions of Blood Vessels From Distributing Artery to Collecting Vein,"Circulation research, 1963, vol. 12(4), pp. 375-378.
Won, R., et al., "Mapping Blood Flow," Nature Photonics, 2011, p. 393-393.
Xu, X. et al., "Time Reversal Ultrasound Modulated Optical Tomography Using a BSO Phase Conjugate Mirror," Society of Photo-Optical Instrumentation Engineers (SPIE) Conference (Feb. 12, 2009), 1 page.
Yao, J., et al., "Photoacoustic brain imaging: from microscopic to macroscopic scales," Neurophotonics, 2014, vol. 1(1), 13 Pages.
Yao, J., "Label-free Oxygen-metabolic Photoacoustic Microscopy in Vivo," Journal of biomedical optics, 2011, vol. 16(7).
Yoa, J., et al., "In vivo Photoacoustic Tomography of Total Blood Flow and Potential Imaging of Cancer Angiogenesis and Hypermetabolism," Technology in Cancer Research and Treatment, 2012, vol. 11(4), pp. 301-307.
Yoa, J., et al., "Transverse Flow Imaging Based on Photoacoustic Doppler Bandwidth Broadening," Journal of Biomedical Optics, 2010, vol. 15(2), 5 Pages.
Zangabad, R., et al., "Photoacoustic Flow Velocity Imaging Based on Complex Field Decorrelation," Photoacoustic, 2021,8 pages.
Zeniieh, D., et al., Parylene-C as High Performance Encapsulation Material for Implantable Sensors, Procedia Engineering, 2014, vol. 87, pp. 1398-1401. https://doi.org/10.1016/j.proeng.2014.11.704.
Zhang, Y., et al., "Transcranial Photoacoustic Computed Tomography of Human Brain Function," Arxiv, 2022, pp. 1-12.
Zhang, Y., et al., Ultrafast Ultrasound Imaging With Cascaded Dual-polarity Waves, IEEE, 2018, vol. 37(4), pp. 906-917.
U.S. Non-Final Office Action dated Mar. 27, 2024 in U.S. Appl. No. 17/302,041.
U.S. Notice of Allowance dated Mar. 13, 2024 in U.S. Appl. No. 17/302,313.
U.S. Appl. No. 18/410,842, inventor Wang L, et al., filed Jan. 11, 2024.

* cited by examiner

SPATIOTEMPORAL ANTIALIASING IN PHOTOACOUSTIC COMPUTED TOMOGRAPHY

CROSS-REFERENCES TO RELATED APPLICATIONS

This application claims priority to and benefit of U.S. Provisional Patent Application No. 62/931,024, titled "SPATIOTEMPORAL ANTIALIASING IN PHOTOACOUSTIC COMPUTED TOMOGRAPHY" and filed on Nov. 5, 2019, which is hereby incorporated by reference in its entirety and for all purposes.

FEDERALLY SPONSORED RESEARCH OR DEVELOPMENT

This invention was made with government support under Grant No(s). CA186567 & EB016963 & NS090579 & NS099717 awarded by the National Institutes of Health. The government has certain rights in the invention.

FIELD

Certain aspects generally pertain to photoacoustic imaging and, more specifically, to photoacoustic computed tomography systems and methods.

BACKGROUND

Photoacoustic tomography provides high-resolution images beyond the optical diffusion limit by combining optical absorption contrast and ultrasonic spatial resolution. By converting highly scattered photons into ultrasonic waves, which are much less scattered than light in biological tissues, photoacoustic tomography can be a useful technique for forming high-resolution images of the optical properties of biological tissues.

SUMMARY

Certain aspects pertain to photoacoustic computed tomography with spatiotemporal antialiasing techniques as can be used, for example, to image biological tissues.

Certain aspects pertain to photoacoustic computed tomography methods that include acquiring photoacoustic data recorded by one or more data acquisition devices of a photoacoustic computed tomography system. The methods also include applying location-based temporal filtering to the photoacoustic data acquired. The location-based temporal filtering is based at least in part on geometry of the ultrasonic transducer array of the photoacoustic computed tomography system. The methods also include reconstructing one or more photoacoustic images from the filtered photoacoustic data. In some cases, an upper cutoff frequency is determined based at least in part on the geometry of the ultrasonic transducer array and one or more lowpass filters with the upper cutoff frequency determined is applied. According to one aspect, spatial interpolation may also be applied after location-based temporal filtering.

Certain aspects pertain to photoacoustic computed tomography methods that include determining whether a reconstruction location is at or inside, or outside an alias-free region. If it is determined that the reconstruction location is outside the alias-free region, location-based temporal filtering is applied to the photoacoustic data acquired. The application of location-based temporal filtering includes applying one or more lowpass filters with an upper cutoff frequency based at least in part on the geometry of the ultrasonic transducer array. The methods also include reconstructing one or more photoacoustic images from the filtered photoacoustic data. According to one aspect, spatial interpolation may also be applied after location-based temporal filtering.

Certain aspects pertain to non-transitory computer readable media for generating one or more photoacoustic images of a specimen being imaged, the non-transitory computer readable media, when read by one or more processors, is configured to perform operations. The operations performed include: acquiring photoacoustic data recorded by one or more data acquisition devices of a photoacoustic computed tomography system, applying location-based temporal filtering to the photoacoustic data acquired, wherein the location-based temporal filtering is based at least in part on geometry of the ultrasonic transducer array of the photoacoustic computed tomography system, and reconstructing one or more photoacoustic images from the filtered photoacoustic data.

Certain aspects pertain to non-transitory computer readable media for generating one or more photoacoustic images of a specimen being imaged, the non-transitory computer readable media, when read by one or more processors, is configured to perform operations. The operations performed include: (i) determining whether a reconstruction location is at or inside, or outside an alias-free region, (ii) if it is determined that the reconstruction location is outside the alias-free region, applying location-based temporal filtering to the photoacoustic data acquired, wherein the applying location-based temporal filtering includes applying one or more lowpass filters with an upper cutoff frequency based at least in part on the geometry of the ultrasonic transducer array, and (iii) reconstructing one or more photoacoustic images from the filtered photoacoustic data.

These and other features are described in more detail below with reference to the associated drawings.

according to one implementation.

Figure 33A:
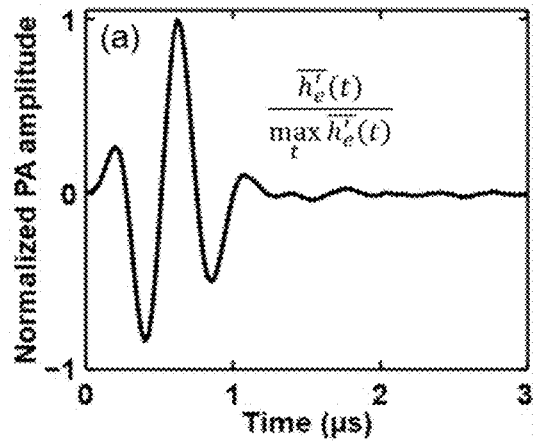

FIG. 33A is a graph with a plot of a normalized estimated point source response, according to one implementation.

Figure 33B:
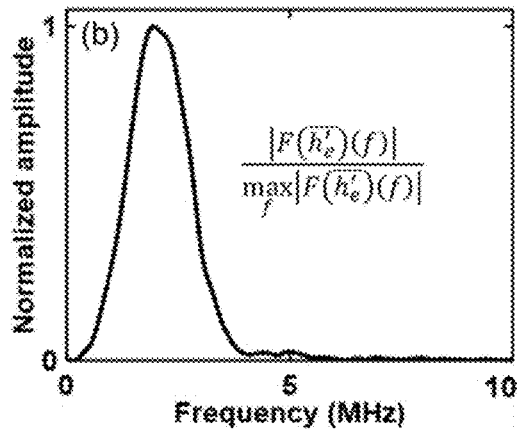

FIG. 33B is a graph with a plot of a normalized frequency spectrum of the estimated point source response, according to an implementation.

Figure 33C:
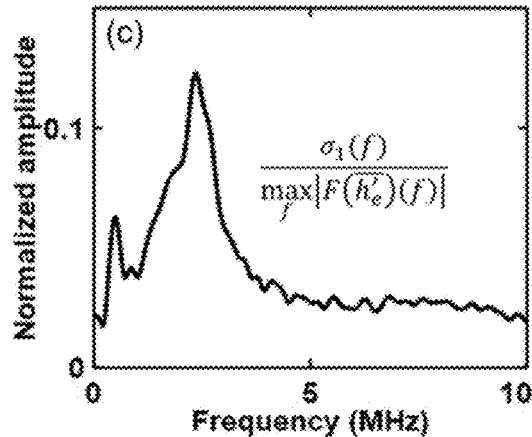

FIG. 33C is a graph with a plot of a normalized frequency spectrum of the noise, according to an implementation.

Figure 33D:
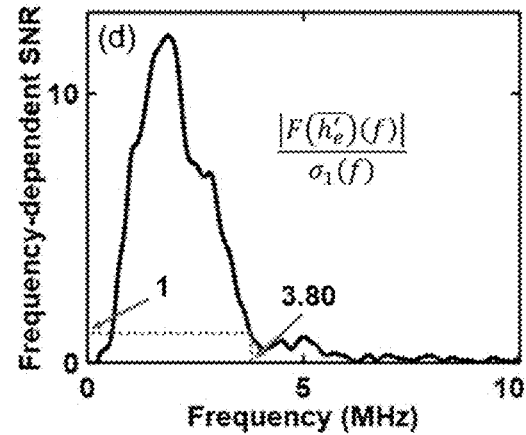

FIG. 33D is a graph with a plot of a frequency-dependent signal-to-noise ratio, according to an implementation.

Figure 33E:
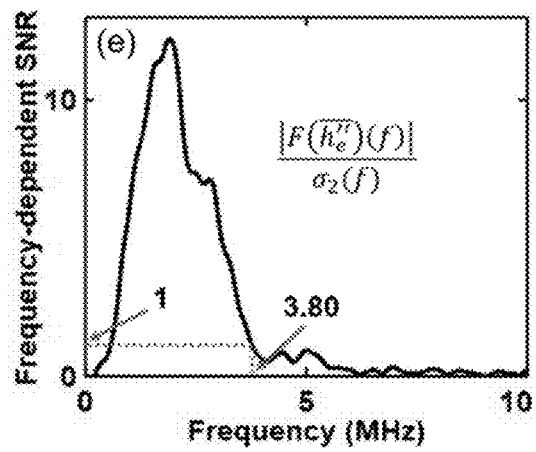

FIG. 33E is a graph with a plot of frequency-dependent SNR of the derivative of the point source response, according to an implementation.

Figure 33F:
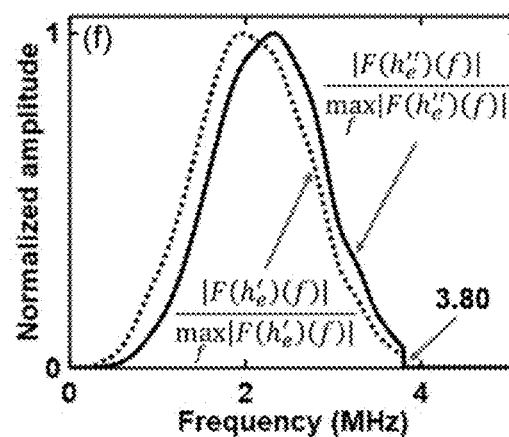

FIG. 33F is a graph with a plot of normalized frequency spectra, according to an implementation.

Figure 34:
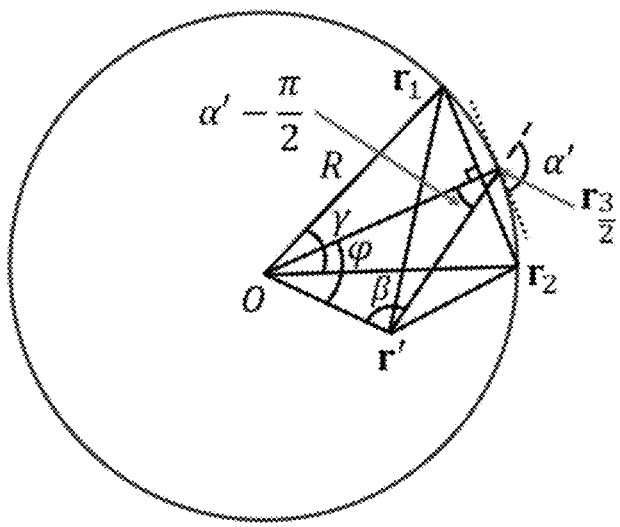

FIG. 34 is a schematic diagram of a full-ring transducer array, according to an implementation.

Figure 35:
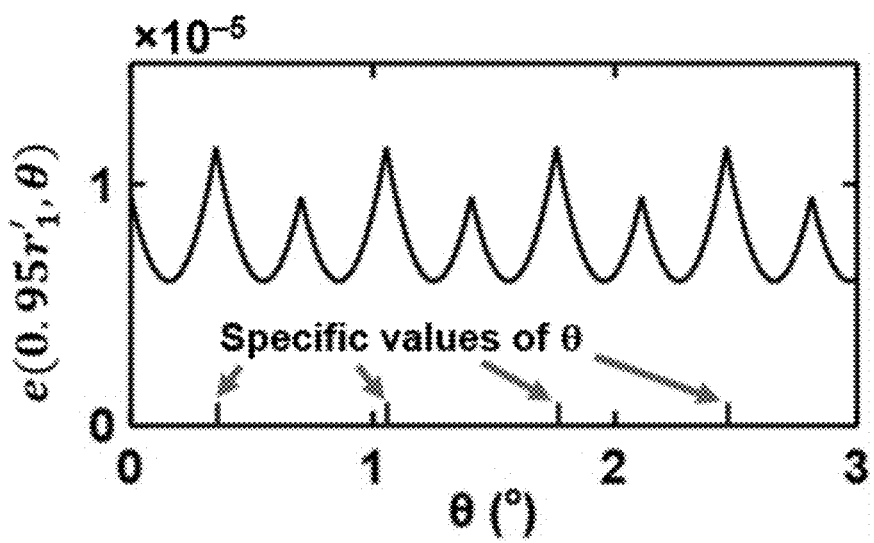

FIG. 35 is a graph with a plot of examples of calculated errors in sample size approximation, according to an implementation.

Figure 36:
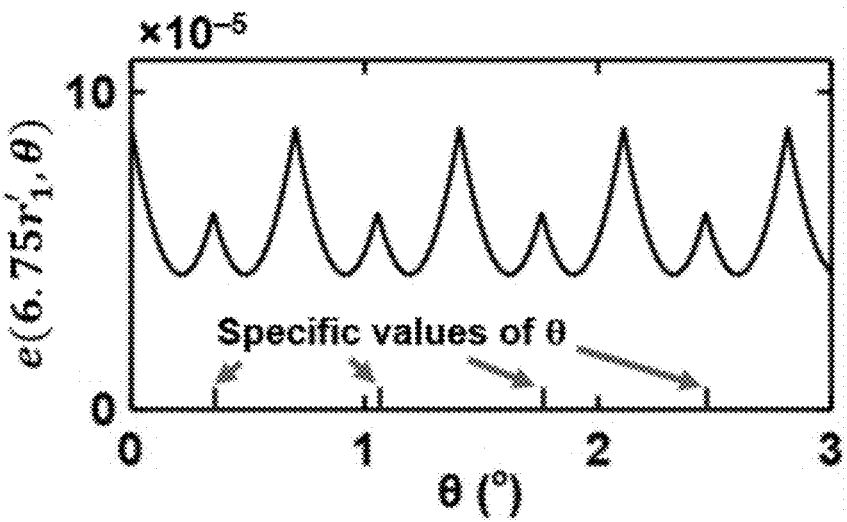

FIG. 36 is a graph with a plot of examples of calculated errors in sample size approximation, according to an implementation.

These and other features are described in more detail below with reference to the associated drawings.

DETAILED DESCRIPTION

Different aspects are described below with reference to the accompanying drawings. The features illustrated in the drawings may not be to scale. In the following description, numerous specific details are set forth in order to provide a thorough understanding of the presented embodiments. The disclosed embodiments may be practiced without one or more of these specific details. In other instances, well-known operations have not been described in detail to avoid unnecessarily obscuring the disclosed embodiments. While the disclosed embodiments will be described in conjunction with the specific embodiments, it will be understood that it is not intended to limit the disclosed embodiments.

I. Introduction to Photoacoustic Computed Tomography (PACT)

Photoacoustic computed tomography (PACT) is an imaging modality that ultrasonically images optical contrast via the photoacoustic effect. PACT can provide tomographic images (e.g., two-dimensional (2D) section(s) and/or 3D volume(s) constructed from 2D sections) of biological tissues and other samples. By converting highly scattered photons into ultrasonic waves, which are much less scattered than light in biological tissues, PACT can form high-resolution images of the optical properties of these tissues at different depths. Some examples of photoacoustic imaging of biological tissues can be found in Kruger, R. A., Kuzmiak, C. M., Lam, R. B., Reinecke, D. R., Del Rio, S. P. and Steed, D., "Dedicated 3D photoacoustic breast imaging," *Med. Phys.*, vol. 40, no. 11 (2013) (hereinafter "Kruger"), Tzoumas, S., et al., "Eigenspectra optoacoustic tomography achieves quantitative blood oxygenation imaging deep in tissues," *Nat. Commun.*, vol. 7 (2016), Dean-Ben, X. L. et al., "Functional optoacoustic neuro-tomography for scalable whole-brain monitoring of calcium indicators," *Light Sci. Appl.*, vol. 5, no. 12, p. e16201, (2016), Li, L. et al., "Single-impulse panoramic photoacoustic computed tomography of small-animal whole-body dynamics at high spatiotemporal resolution," *Nat. Biomed. Eng.*, vol. 1, no. 5, p. 0071 (2017), Matsumoto, Y., et al., "Label-free photoacoustic imaging of human palmar vessels: a structural morphological analysis," *Sci. Rep.*, vol. 8, no. 1, p. 786 (2018), Lin, L. et al., "Single-breath-hold photoacoustic computed tomography of the breast," *Nat. Commun.*, vol. 9, no. 1, p. 2352 (2018), Li, L., "Small near-infrared photochromic protein for photoacoustic multi-contrast imaging and detection of protein interactions in vivo," *Nat. Commun.*, vol. 9, no. 1, p. 2734 (2018), and Wu, Z. et al., "A microrobotic system guided by photoacoustic computed tomography for targeted navigation in intestines in vivo," *Sci. Robot.*, vol. 4, no. 32, p. 0613, (2019), which are hereby incorporated by reference in their entireties. Some examples of PACT methods and systems can be found in U.S. patent application Ser. No. 16/798,204, titled "PHOTOACOUSTIC COMPUTED TOMOGRAPHY (PACT) SYSTEMS AND METHODS," filed on Feb. 21, 2020; PCT publication WO2018102446, titled "SINGLE-IMPULSE PANORAMIC PHOTOACOUSTIC COMPUTED TOMOGRAPHY (SIP-PACT), filed on Nov. 29, 2017; U.S. Patent Publication US 2016/0262628, titled "PHOTOACOUSTIC COMPUTED TOMOGRAPHY WITH AN ACOUSTIC REFLECTOR." filed on Nov. 12, 2014; which are hereby incorporated by reference in their entireties.

PACT methods generally include a data acquisition phase and an image reconstruction phase. During the data acquisition phase, photon-induced acoustic waves (sometimes referred to herein as "photoacoustic waves") are detected by an ultrasonic transducer array or its scanning equivalent, such as a full-ring ultrasonic transducer array, a linear array, or two-dimensional array. During the image reconstruction phase, the detected acoustic signals are used to reconstruct the sample's optical absorption via inverse reconstruction algorithms. Some examples of inverse reconstruction algorithms that can be used include: (i) forward-model-based iterative methods, (ii) time-reversal methods, and (iii) the universal back-projection (UBP) method. Examples of the universal back-projection (UBP) method can be found in Kruger, Li, L. et al., "Single-impulse panoramic photoacoustic computed tomography of small-animal whole-body dynamics at high spatiotemporal resolution," *Nat. Biomed. Eng.*, vol. 1, no. 5, p. 0071 (2017), Lin, L. et al., "Single-breath-hold photoacoustic computed tomography of the breast," *Nat. Commun.*, vol. 9, no. 1, p. 2352 (2018), Xu M. and Wang, L. V., "Universal back-projection algorithm for photoacoustic computed tomography," *Phys. Rev. E*, vol. 71, no. 1, p. 016706 (2005), Song, L., Maslov, K. I., Bitton, R., Shung, K. K., and Wang, L. V., "Fast 3-D dark-field reflection-mode photoacoustic microscopy in vivo with a 30-MHz ultrasound linear array," *J. Biomed. Opt.*, vol. 13, no. 5, p. 054028 (2008), Dean-Ben, X. L. and Razansky, D., "Portable spherical array probe for volumetric real-time optoacoustic imaging at centimeter-scale depths," *Opt. Express*, vol. 21, no. 23, pp. 28062-28071 (2013), and Pramanik, M., "Improving tangential resolution with a modified delay-and-sum reconstruction algorithm in photoacoustic and thermoacoustic tomography," JOSA A, vol. 31, no. 3, pp. 621-627 (2014), which are hereby incorporated by reference in their entireties. Examples of forward-model-based iterative methods can be found in Wang, K., et al. "Investigation of iterative image reconstruction in three-dimensional optoacoustic tomography," *Phys. Med. Biol.*, vol. 57, no. 17, p. 5399 (2012), Huang, Chao et al., "Full-wave iterative image reconstruction in photoacoustic tomography with acoustically inhomogeneous media," *IEEE Trans. Med. Imaging*, vol. 32, no. 6, pp. 1097-1110 (June 2013), Mitsuhashi, K., et al., "A forward-adjoint operator pair based on the elastic wave equation for use in transcranial photoacoustic computed tomography," *SIAM J. Imaging Sci.*, vol. 10, no. 4, pp. 2022-2048 (2017), Treeby, B. E. and Cox, B. T., "k-Wave: MATLAB toolbox for the simulation and reconstruction of photoacoustic wave fields," *J. Biomed. Opt.*, vol. 15, no. 2, p. 021314, (2010), Mitsuhashi, K., Wang, K. and Anastasio, M. A., "Investigation of the far-field approximation for modeling a transducer's spatial impulse response in photoacoustic computed tomography," *Photoacoustics*, vol. 2, no. 1, pp. 21-32 (2014), Han, Y., Ntziachristos, V. and Rosenthal, A., "Optoacoustic image reconstruction and system analysis for finite-aperture detectors under the wavelet-packet framework," *J. Biomed. Opt.*, vol. 21, no. 1, p. 016002 (2016), Arridge, S., et al., "Accelerated high-resolution photoacoustic tomography via compressed sensing," ArXiv Prepr., ArXiv160500133 (2016), Han, Y. et al., "Three-dimensional optoacoustic reconstruction using fast sparse representation," *Opt. Lett.*, vol. 42, no. 5, pp. 979-982 (2017), Schoeder, S. et al. "Optoacoustic image reconstruction: the full inverse problem with variable bases," *Proc. R. Soc. A.*, vol. 474, no. 2219, p. 20180369 (2018), and Matthews, T. P., Poudel, J., Li, L., Wang, L. V. and Anastasio, M. A., "Parameterized Joint Reconstruction of the Initial Pressure and Sound Speed Distributions for Photoacoustic Computed Tomography," SIAM *J. Imaging Sci.*, vol. 11, no. 2, pp. 1560-1588 (2018), which are hereby incorporated by reference in their entireties. Examples of time reversal methods can be found in Xu, Y. and Wang, L. V., "Time reversal and its application to tomography with diffracting sources," *Phys. Rev. Lett.*, vol. 92, no. 3, p. 033902 (2004), Treeby, B. E., Zhang, E. Z. and Cox, B., "Photoacoustic tomography in absorbing acoustic media using time reversal," *Inverse Probl.*, vol. 26, no. 11, p. 115003 (2010), Cox, B. T. and Treeby, B. E., "Artifact trapping during time reversal photoacoustic imaging for acoustically heterogeneous media," *IEEE Trans. Med. Imaging*, vol. 29, no. 2, pp. 387-396 (2010), Treeby, B. E., Jaros, J. and Cox, B. T., "Advanced photoacoustic image reconstruction using the k-Wave toolbox," in *Photons Plus Ultrasound: Imaging and Sensing* 2016, vol. 9708, p. 97082P (2016), and Ogunlade, O. et al., "In vivo three-dimensional photoacoustic imaging of the renal vasculature in preclinical rodent models," *Am. J. Physiol.-Ren. Physiol.*, vol. 314, no. 6, pp. F1145-F1153 (2017), which are hereby incorporated by reference in their entireties. Examples of universal back-projection (UBP) method can be found in Kruger, Li, L. et al., "Single-impulse panoramic photoacoustic computed tomography of small-animal whole-body dynamics at high spatiotemporal resolution," *Nat. Biomed. Eng.*, vol. 1, no. 5, p. 0071 (2017), Lin, L. et al., "Single-breath-hold photoacoustic computed tomography of the breast," *Nat. Commun.*, vol. 9, no. 1, p. 2352 (2018), Xu M. and Wang, L. V., "Universal back-projection algorithm for photoacoustic computed tomography," *Phys. Rev. E*, vol. 71, no. 1, p. 016706 (2005), Song, L., Maslov, K. I., Bitton, R., Shung, K. K., and Wang, L. V., "Fast 3-D dark-field reflection-mode photoacoustic microscopy in vivo with a 30-MHz ultrasound linear array," *J. Biomed. Opt.*, vol. 13, no. 5, p. 054028 (2008), Dean-Ben, X. L. and Razansky, D., "Portable spherical array probe for volumetric real-time optoacoustic imaging at centimeter-scale depths," *Opt. Express*, vol. 21, no. 23, pp. 28062-28071 (2013), and Pramanik, M., "Improving tangential resolution with a modified delay-and-sum reconstruction algorithm in photoacoustic and thermoacoustic tomography," *JOSA A*, vol. 31, no. 3, pp. 621-627 (2014), which are hereby incorporated by reference in their entireties.

PACT based on a full-ring ultrasonic transducer array is widely used for small animal wholebody and human organ imaging, thanks to its high in-plane resolution and full-view fidelity. Some discussion of PACT used to for small animal wholebody and/or human organ imaging can be found in Li, L. et al., "Single-impulse panoramic photoacoustic computed tomography of small-animal whole-body dynamics at high spatiotemporal resolution," *Nat. Biomed. Eng.*, vol. 1, no. 5, p. 0071 (2017), Xu, Y., Xu, M. and Wang, L. V., "Exact frequency-domain reconstruction for thermoacoustic tomography. II. Cylindrical geometry," *IEEE Trans. Med. Imaging*, vol. 21, no. 7, pp. 829-833, 2002, which are hereby incorporated by reference in their entireties. To help avoid any artifacts occurring in image reconstruction in PACT, the ultrasonic transducer array should provide dense spatial sampling around the object to satisfy the Nyquist sampling theorem. That is, the spatial sampling interval on the specimen surface should be less than half of the lowest detectable acoustic wavelength. Otherwise, artifacts may appear in image reconstruction, a problem called spatial aliasing. In practice, due to the high cost of a transducer array with a large number of elements or limited scanning time, spatially sparse sampling is common.

PACT systems and methods with spatiotemporal antialiasing described herein may mitigate artifacts caused by spatial undersampling without having to physically increase the number of elements in the transducer array to satisfy Nyquist sampling criterion. Moreover, in some implementations, the PACT systems and/or methods with spatiotemporal antialiasing may compensate for undersampling without substantially compromising image resolution. PACT systems/methods with spatiotemporal antialiasing may be advantageous in reducing equipment costs by being able to utilize less expensive ultrasonic transducer arrays that sparsely sample while still avoiding artifacts and maintaining high resolution in photoacoustic images.

In the following sections, the sources of spatial aliasing in a full-ring geometry PACT and linear array PACT and applications to other array geometries are discussed. The PACT systems and methods with spatiotemporal antialiasing described here implement one or more techniques that may mitigate artifacts caused by spatial aliasing without physically increasing the number of elements in an ultrasonic transducer array.

Based on spatiotemporal analysis, two sources of spatial aliasing are: spatial sampling and image reconstruction. To classify different cases of spatial aliasing based on locations (of source points and reconstruction locations), three zones are defined in the imaging domain of the ultrasonic transducer array: (1) a detection zone $S_0$, (2) a one-way Nyquist zone $S_1$, and (3) a two-way Nyquist zone $S_2$. Zone $S_1$ is contained in $S_0$, while $S_2$ is contained in $S_1$. Spatial aliasing in spatial sampling does not appear for objects inside $S_1$, but appears for objects outside $S_1$. Spatial aliasing in image reconstruction does not appear for objects and reconstruction locations inside $S_2$, but appears for other combinations of objects and reconstruction locations. Zone $S_2$ is the original aliasing-free region, which can be extended to $S_1$ by one or more antialiasing techniques described herein. The aliasing free region can also be further extended from $S_1$ to $S_1'$ by one or more antialiasing techniques described herein.

Two categories of antialiasing techniques include: spatial interpolation and temporal filtering. Spatial interpolation can be used to eliminate spatial aliasing in image reconstruction without compromising the spatial resolution, effectively extending the alias-free zone from $S_2$ to $S_1$. Temporal filtering that uses an upper cutoff frequency based on Nyquist sampling criterion can remove aliasing in spatial sampling, while compromising the spatial resolution in the affected regions. Thus, this combination of spatial interpolation with temporal filtering using the upper cutoff frequency based on Nyquist sampling criterion removes spatial aliasing in both spatial sampling and image reconstruction, while compromising the spatial resolution.

In certain aspects, as a balance between spatial antialiasing and high resolution, an antialiasing filter is designed based on the reconstruction location's distance to the center of the ultrasonic transducer array. In a full-ring transducer array implementation, the reconstruction location's distance is to the full-ring array center. Temporal filtering that implements an antialiasing filter designed based on the reconstruction location's distance to the center of the ultrasonic transducer array is referred to herein as location-dependent temporal filtering (also sometimes referred to as "radius-dependent" temporal filtering).

In these aspects, spatial interpolation can extend the alias-free zone from $S_2$ to $S_1$ and applying location-dependent temporal filtering along, the alias-free zone is further extended from $S_1$ to $S_1'$. The lower the upper cutoff frequency used in the location-based temporal filtering, the larger the extended region $S_1'$ and the poor the imaging resolution. As provided in Sections IV and V, the results from numerical simulations and in vivo experiments show that location-dependent temporal filtering along with spatial interpolation may be effective in mitigating artifacts caused by spatial aliasing in either image reconstruction or spatial sampling.

Antialiasing techniques that include spatial interpolation and/or location-based temporal filtering are discussed below with reference to a transducer array having circular geometry (e.g., full-ring array) and a linear geometry, for which expressions of for zones $S_2$ and $S_1$ are provided. It would be understood that the disclosure is not so limiting and that these antialiasing techniques may be used for other array geometries.

II. PACT Systems and Methods with Spatiotemporal Antialiasing

Spatial aliasing may be generally classified into two categories: (1) aliasing in spatial sampling and (2) aliasing in image reconstruction. In certain implementations, PACT systems and methods with spatiotemporal antialiasing described herein implement antialiasing techniques including: (i) spatial interpolation and/or (ii) location-dependent temporal filtering that is dependent on the geometry of the ultrasonic transducer array. Spatial interpolation can mitigate (reduce or eliminate) spatial aliasing in image reconstruction. Location-dependent temporal filtering can mitigate spatial aliasing in spatial sampling. In one aspect, location-dependent temporal filtering implements an antialiasing filter with one or more lowpass filters having an upper cutoff frequency that is based on the distance between the reconstruction location and the ultrasonic transducer array. In one implementation, an antialiasing technique determines whether the reconstruction location (and associated source point) is within the present alias-free zone and if it is determined that the reconstruction location is outside the present alias-free zone, an antialiasing filter is applied to the raw data to extend the present alias-free zone to an expanded alias-free zone to include the reconstruction location. In certain implementations, the PACT methods and systems with spatiotemporal antialiasing mitigate aliasing artifacts in image reconstruction.

Although the spatiotemporal antialiasing techniques are described in this section with reference to a transducer array having a circular geometry and a transducer array having a linear geometry, it would be understood that the disclosure is not so limiting, and that these techniques would apply to other array geometries. For example, based on the basic 1D circular and linear geometries, one can apply 2D/3D geometries, such as, a planar geometry and the spherical geometry, through decomposition. Moreover, although the antialiasing techniques are sometimes described being implementing with the universal back-projection (UBP) described in Xu, M. and Wang, L. V., "Universal back-projection algorithm for photoacoustic computed tomography," *Phys. Rev. E*, vol. 71, no. 1, p. 016706 (2005), it would be understood that other inverse reconstruction techniques can be used, such as those referenced in Section I. In addition, the antialiasing techniques described herein may apply to other image reconstruction methods. For example, spatial interpolation may be used in time reversal methods to generate a dense enough grid for numerical computation. Furthermore, location-dependent temporal filtering may be incorporated into a wave propagation model and be used in time reversal methods and/or iterative methods to mitigate aliasing in spatial sampling according to other aspect.

A. Photoacoustic Image Reconstruction

In a homogeneous medium, a photoacoustic wave can be expressed as:

$$p(r,t) = \frac{1}{4\pi c^2} \frac{\partial}{\partial t} \left( \frac{1}{ct} \int_V dr' p_0(r') \delta\left(t - \frac{\|r'-r\|}{c}\right) \right). \quad \text{(Eqn. 1)}$$

A detailed discussion of the expression in Eqn. 1 can be found Wang, L. V. and Wu, H., Biomedical optics: principles and imaging. John Wiley & Sons (2012), Zhou, Y., Yao, J. and Wang, L. V., "Tutorial on photoacoustic tomography," *J. Biomed. Opt.*, vol. 21, no. 6, p. 061007, 2016, which are hereby incorporated by reference in their entireties. In Eqn. 1, p(r, t) is the pressure at location r and time t, c is the speed of sound, V is the volumetric space occupied by the tissue, and $p_0(r')$ is the initial pressure at r'. Eqn. 1 can be rewritten as:

$$p(r,t) = \frac{1}{4\pi c^2} \int_V \frac{p_0(r')}{\|r'-r\|} \frac{\partial}{\partial t} \delta\left(t - \frac{\|r'-r\|}{c}\right) dr'. \quad \text{(Eqn. 2)}$$

Discreizing Eqn 2 in space, provides:

$$p(r_n, t) = \frac{1}{4\pi c^2} \sum_{m=1}^{M} v_m \frac{p_0(r')}{\|r'_m - r_n\|} \frac{\partial}{\partial t} \delta\left(t - \frac{\|r'-r\|}{c}\right), \quad \text{(Eqn. 3)}$$

$$n = 1, 2, \ldots, N.$$

Eqn. 3 refers to m source points distributed at $r_m'$, to =1, 2, . . . M, and N point detection elements distributed at $r_n$, n=1, 2, . . . , N. The term $v_m$ is the volume of the m-th source point. The response of an ultrasonic transducer array can be described as:

$$\hat{p}(r_n,t) = p(r_n,t) * h_e(t), n=1,2, \ldots, N. \quad \text{(Eqn. 4)}$$

Here, $\hat{p}(r_n, t)$ is the pressure impinging on the n-th point detection element (transducer element) at time t, and $h_e(t)$ is the ultrasonic transducer's electric impulse response. Substituting Eqn. 3 into Eqn. 4, the following is obtained:

$$\hat{p}(r_n, t) = \frac{1}{4\pi c^2} \sum_{m=1}^{M} v_m \frac{p_0(r'_m)}{\|r'_m - r_n\|} h'_e\left(t - \frac{\|r'_m - r_n\|}{c}\right). \quad \text{(Eqn. 5)}$$

The term $$h'_e\left(t - \frac{\|r'_m - r_n\|}{c}\right)$$

is a function of both time and space, where the first prime denotes a temporal derivative.

When photoacoustic signals received by the ultrasonic transducer array are digitized by one or more data acquisition systems (DAQs), an antialiasing filter (e.g. one or more low-pass filters) with an upper cutoff frequency selected for a sufficiently high temporal sampling rate may be used to mitigate temporal aliasing in certain implementations. For simplicity, the time variable is assumed to be continuous and spatial variables are discretized, which allows for a discussion of spatial sampling (sometimes referred to herein as "SS"). For different transducer detection geometries (e.g., planar, spherical, and cylindrical surfaces of transducer array), image flapping the initial pressure $p_0$ (r") using the Universal back-projection (UBP) algorithm found in Xu, M. and Wang, L. V., "Universal back-projection algorithm for photoacoustic computed tomography," *Phys. Rev. E*, vol. 71, no. 1, p. 016706 (2005), provides:

$$p_0(r'') = \int_{\Omega_0} b\left(r, t = \frac{\|r'' - r\|}{c}\right) \frac{d\Omega}{\Omega_0}, \quad \text{(Eqn. 6)}$$

where the back-projection term, $$b(r, t) = 2p(r, t) - 2t\frac{\partial p(r, t)}{\partial t}, \quad d\Omega = \frac{dS}{\|r'' - r\|^2} \frac{n_S(r) \cdot (r'' - r)}{\|r'' - r\|},$$

is the solid angle for the detection element at r with respect to reconstruction location r", dS is the detection element surface area, and $n_S(r)$ is the ingoing normal vector. The total solid angle is denoted as $\Omega_0$. The actual or true pressure p(r, t) may be approximated by the detected pressure $\hat{p}(r_n, t)$, leading to the following discretized form of Eqn. 6:

$$\hat{p}_0(r'') \approx \sum_{n=1}^{N} w_n \hat{b}\left(r_n, t = \frac{\|r'' - r_n\|}{c}\right). \quad \text{(Eqn. 7)}$$

Here, $\hat{p}_0(r'')$ is the reconstructed initial pressure an $$\hat{b}(r_n, t) = 2\hat{p}(r_n, t) - 2t\frac{\partial \hat{p}(r_n, t)}{\partial t}$$

is the back-projection term computed from the detected pressure by the ultrasonic transducer array. The weights $w_n$, n=1, 2, . . . , N come from $$\frac{d\Omega}{\Omega_0}$$

in Eqn. 6.

B. Spatiotemporal Analysis of Spatial Aliasing in Spatial Sampling (SS) and Image Reconstruction (IR)

To determine the source of spatial aliasing in a PACT system, spatiotemporal analysis is used to analyze the detection geometry of a transducer array. For a particular detection geometry, the spatial sampling frequency may be calculated using reciprocals of the distances between adjacent sampling positions of the transducer elements in the array. In this section, a spatiotemporal analysis of a full-ring transducer array with point detection elements is used as an example. It would be understood that this spatiotemporal analysis can be applied to other array geometries such as a linear array as discussed in Section II(C)(2). The full-ring ultrasonic transducer array has a radius of R and has N evenly-distributed detection elements. The upper cutoff frequency of the full-ring ultrasonic transducer array is $f_c$, and the corresponding lower cutoff wavelength is $$\lambda_c = \frac{c}{f_c}.$$

An example of a method for estimating an upper cutoff frequency $f_c$ that would eliminate spatial aliasing due to spatial sampling in the entire detection zone (imaging domain) of the transducer array is provided in Section VII. In certain implementations, a PACT system/method implements an antialiasing filter with one or more low pass filters (e.g., a third-order lowpass Butterworth filter and a sinc filter, both with same cutoff frequency of $f_c$) with an upper cutoff frequency that is lower than this estimated upper cutoff frequency to substantially mitigate aliasing due to spatial sampling while maintaining the best level of image resolution as discussed in Section II(C). The higher the cutoff frequency, the better the image resolution. In certain implementations, the highest possible cutoff frequency is selected, and thus have the best image resolution.

For a full-ring transducer array, the detection zone, $S_0$, of the full-ring transducer array is defined as:

$$S_0 = \{r | \|r\| \leq R\}. \quad \text{(Eqn. 8)}$$

where the full-ring transducer array has a radius, R and r' is a source point or a reconstruction location.

Figure 1A:
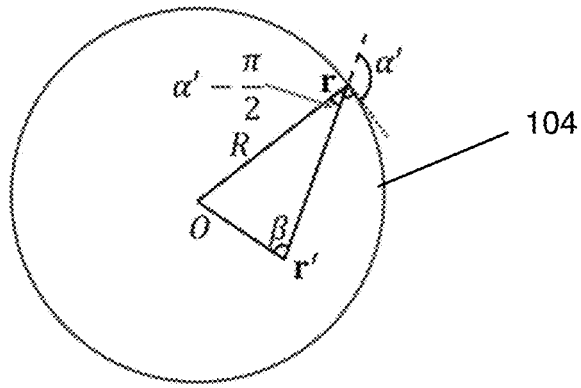
FIG. 1A is a schematic diagram depicting an analysis of spatial aliasing in spatial sampling by the full-ring ultrasonic transducer array, according to implementations.
Figure 1B:
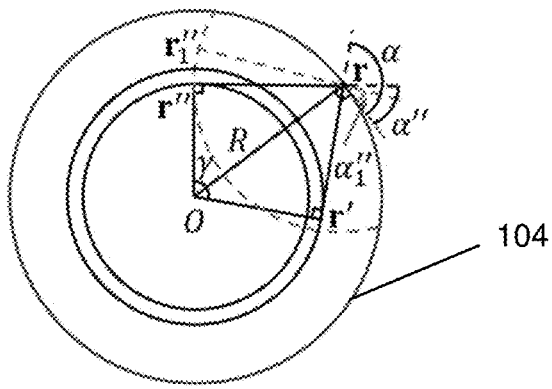
FIG. 1B is a schematic diagram depicting an analysis of spatial aliasing in image reconstruction, according to one implementation.
Figure 1C:
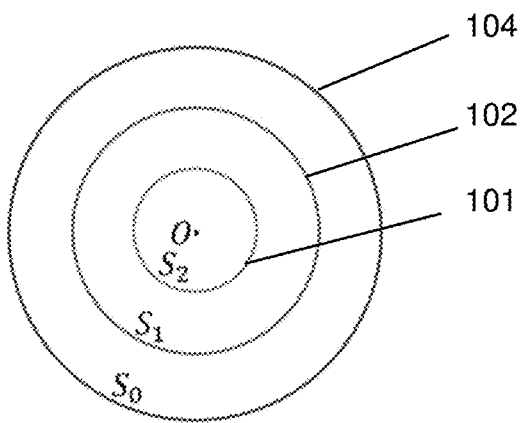
FIG. 1C is a schematic diagram illustrating three regions in the field-of-view of the full-ring transducer array that represent regions of different types of spatial aliasing, according to one implementation.

FIG. 1A, FIG. 1B, and FIG. 1C are schematic diagrams depicting an analysis of spatial aliasing in a PACT system with a full-ring ultrasonic transducer array, according to certain implementations. The diagrams include a detection zone, $S_0$, 104, with an outer circle representing the detection surface of a full-ring transducer array having a radius R and N evenly-distributed transducer elements. The center O of detection zone, $S_0$, 104, represents the origin of a coordinate system used in image reconstruction.

FIG. 1A is a schematic diagram depicting an analysis of spatial aliasing in spatial sampling (sometimes referred to herein as "SS") by the full-ring ultrasonic transducer array, according to implementations. The diagram includes a representative transducer detection element with location r and a representative source point with location r'.

FIG. 1B is a schematic diagram depicting an analysis of spatial aliasing in image reconstruction (sometimes referred to herein as "IR"), according to one implementation. The diagram includes a detection (transducer) element with a detection element location r. The diagram also includes two reconstruction locations r" and $r_1$", and a source point location r'.

FIG. 1C is a schematic diagram illustrating three regions in the field-of-view of the full-ring transducer array that represent where different types of aliasing might arise, according to one implementation. The diagram includes an alias-free two-way Nyquist zone, $S_2$, 101, which contains all source points and reconstruction locations where image reconstruction, e.g., reconstruction including universal back projection (UBP), yields no spatial aliasing. The diagram also includes a one-way Nyquist zone, $S_1$, 102, within which aliasing does not exist in spatial sampling, but may exist in image reconstruction. The diagram also includes a third zone, $S_0$, which is the imaging domain. Within the third zone, $S_0$, 103 aliasing may exist due to spatial sampling.

First, aliasing from spatial sampling of the full-ring transducer array is analyzed. When the detection element at location r varies discretely, the step size along the perimeter of the full-ring transducer array is $$\frac{2\pi R}{N}.$$

The tangential direction to the perimeter is shown as a dotted line in FIG. 1A, which is perpendicular to the vector r from the center O of the circle. When considering a source point at r', and extending the line segment r–r' as a dashed line extension in FIG. 1A. Vectors –r and r–r' form an angle while vector r–r' forms an angle $\alpha'$ with the tangential dotted line that is perpendicular to the vector r. The angle formed by vectors –r and r'–r can be expressed as $$\alpha' - \frac{\pi}{2}.$$

The local sampling step size of ‖r–r'‖ may be approximated as:

$$\frac{2\pi R}{N}\cos\alpha'. \quad \text{(Eqn. 9)}$$

The absolute value means the length of the local sampling step size, while the sign (positive or negative of the value in Eqn. 9 means the sampling direction. An example of a method that can be used to approximate the sampling step size is discussed in Section VIII. From Eqn. 5, at a given time t, and with the lower cutoff wavelength $\lambda_c$, the Nyquist criterion can be expressed as:

$$\frac{2\pi R |\cos\alpha'|}{N} < \frac{\lambda_c}{2}. \quad \text{(Eqn. 10)}$$

The Law of Sines can be used to transform this inequality to a constraint for the source point location r', to:

$$\frac{R}{\sin\beta} = \frac{r'}{\sin\left(\alpha' - \frac{\pi}{2}\right)} = \frac{r'}{-\cos\alpha'}. \quad \text{(Eqn. 11)}$$

Here r'=‖r'‖. Using Eqn. 11, Eqn. 9 can be transformed to:

$$\frac{2\pi R\cos\alpha'}{N} = \frac{-2\pi r'\sin\beta}{N}. \quad \text{(Eqn. 12)}$$

Combining Inequality in Eqn. 10 and Eqn. 12, the following is obtained:

$$r' < \frac{N\lambda_c}{4\pi |\sin\beta|}, \quad \text{(Eqn. 13)}$$

which must be satisfied for any $\beta \in [0, 2\pi)$. When $$\beta = \frac{\pi}{2} \text{ or } \frac{3\pi}{2},$$

Eqn. 13 leads to the smallest upper limit of r':

$$r' < \frac{N\lambda_c}{4\pi}, \quad \text{(Eqn. 14)}$$

and the length of the local step size maximizes to $$\frac{2\pi r'}{N}.$$

If r' satisfies Eqn. 14, the length of the local step size of ‖r–r'‖ given by Eqn. 12 also satisfies the Nyquist criterion:

$$\frac{2\pi R |\cos\alpha'|}{N} = \frac{2\pi r' |\sin\beta|}{N} \leq \frac{2\pi r'}{N} < \frac{\lambda_c}{2}. \quad \text{(Eqn. 15)}$$

The one-way Nyquist zone $S_1$ may be defined as:

$$S_1 = \left\{ r' \mid \|r'\| < \frac{N\lambda_c}{4\pi} \right\}. \quad \text{(Eqn. 16)}$$

The boundary of one-way Nyquist zone $S_1$ can be considered a virtual detection surface, where the sampling spacing is scaled down from the actual detection spacing by $$\frac{R_1}{R}$$

with $R_1$ being the radius of one-way Nyquist zone $S_1$. For any source point inside zone $S_1$, there is no spatial aliasing due to spatial sampling because the sampling spacing of the transducer array is less than half of the lower cutoff wavelength.

Next, spatial aliasing due to image reconstruction is analyzed. Eqn. 5 is substituted into Eqn. 6, obtaining:

$$\hat{p}_0(r'') \approx \frac{1}{2\pi c^2} \sum_{n=1}^{N} w_n \sum_{m=1}^{M} v_m \frac{p_0(r'_m)}{\|r'_m - r_n\|} \quad \text{(Eqn. 17)}$$

-continued $$\left(1-\left(t+\frac{\|r'_m-r_n\|}{c}\right)\frac{\partial}{\partial t}\right)h'_e\left(\frac{\|r''-r_n\|}{c}-\frac{\|r'_m-r_n\|}{c}\right).$$

Using a differential operation, the following is obtained:

$$\left(1-\left(t+\frac{\|r'_m-r_n\|}{c}\right)\frac{\partial}{\partial t}\right)=h'_e(t)-\left(t+\frac{\|r'_m-r_n\|}{c}\right)h''_e(t). \quad \text{(Eqn. 18)}$$

The expression $$\left(1-\left(t+\frac{\|r'_m-r_n\|}{c}\right)\frac{\partial}{\partial t}\right)h'_e\left(\frac{\|r''-r_n\|}{c}-\frac{\|r'_m-r_n\|}{c}\right)$$

in Eqn. 17 includes two terms:

$$h'_e\left(\frac{\|r''-r_n\|}{c}-\frac{\|r'_m-r_n\|}{c}\right) \text{ and}$$

$$\frac{\|r''-r_n\|}{c}h''_e\left(\frac{\|r''-r_n\|}{c}-\frac{\|r'_m-r_n\|}{c}\right).$$

As provided in Section VI, the difference between the spectra of $$\frac{\|r''-r_n\|}{c}h''_e\left(\frac{\|r''-r_n\|}{c}-\frac{\|r'_m-r_n\|}{c}\right)$$

and $$h''_e\left(\frac{\|r''-r_n\|}{c}-\frac{\|r'_m-r_n\|}{c}\right)$$

is negligible. In addition, as shown in Section VII, $h_e''(t)$ has the same upper cutoff frequency as $h_e'(t)$. Thus, if $h_e'(t)$ has an upper cutoff frequency, $f_c$, $$\left(1-\left(t+\frac{\|r'_m-r_n\|}{c}\right)\frac{\partial}{\partial t}\right)h'_e(t)$$

has approximately the same upper cutoff frequency.

In FIG. 1B, extensions of the line segments $r-r''$, $r-r_1'$, and $r-r'$ form angles $\alpha''$, $\alpha_1''$ and $\alpha'$, respectively, with the tangential dotted line that is perpendicular to r. Vectors r" and r' form an angle $$\gamma=\arccos\left(\frac{r''}{R}\right)+\arccos\left(\frac{r'}{R}\right),$$

where $r''=\|r''\|$ and $r'=\|r'\|$. Points r" and $r_1$" are on the same circle centered at r. Given a reconstruction location r" and a source point location r' as shown in FIG. 1B, the sampling step size of $\|r-r\|-\|r'-r\|$ needs only be analyzed while the detection element location r varies. The lengths of the step sizes of both $\|r''-r\|$ and $\|r'r\|$ reach maxima when $r''-r$ and $r'-r$ are perpendicular to r" and r', respectively. If the angle $\gamma$ between vectors r" and r' satisfies $$\gamma=\arccos\left(\frac{r''}{R}\right)+\arccos\left(\frac{r'}{R}\right),$$

where $r''=\|r''\|$ and $r'=\|r'\|$, then the lengths of the step sizes of $\|r'-r\|$ and $\|r'-\|$ achieve maxima of $$\frac{2\pi r''}{N} \text{ and } \frac{2\pi r'}{N},$$

respectively, with r at the same location, as shown in FIG. 1B. In addition, as r passes this location clockwise, $\|r''-r\|$ increases while $\|r'-r\|$ decreases. Thus, the length of the step size of $\|r''-r\|-\|r'-r\|$ achieves its maximum of:

$$\frac{2\pi r''}{N}+\frac{2\pi r'}{N}=\frac{2\pi(r''+r')}{N}. \quad \text{(Eqn. 19)}$$

The Nyquist sampling criterion provides that:

$$\frac{2\pi(r''+r')}{N}<\frac{\lambda_c}{2}, \quad \text{(Eqn. 20)}$$

which is equivalent to:

$$r''+r'<\frac{N\lambda_c}{4\pi}. \quad \text{(Eqn. 21)}$$

The physical propagation of the photoacoustic wave from the object being imaged to the transducer detector elements is succeeded by a time-reversal propagation for the image reconstruction. The combined region encompasses a disc with a radius of r"+r'. On the perimeter of this disc, the Nyquist sampling criterion provides that the sampling spacing be less than half of the lower cutoff wavelength, i.e., Eqn. 20.

The two-way Nyquist zone $S_2$ may be defined as:

$$S_2=\left\{r'\,\Big|\,\|r'\|<\frac{N\lambda_c}{8\pi}\right\}. \quad \text{(Eqn. 22)}$$

The boundary of two-way Nyquist zone $S_2$ may be considered a virtual detection surface where the sampling spacing is scaled down from the actual detection spacing by $$\frac{R_2}{R}$$

with $R_2$ being the radius of two-way Nyquist zone $S_2$. If the source points are inside zone $S_2$ and there is image reconstruction at points within zone $S_2$, then $$r'<\frac{N\lambda_c}{8\pi} \text{ and } r''<\frac{N\lambda_c}{8\pi},$$

respectively, and the inequality of Eqn. 21 is satisfied. Thus, there is no spatial aliasing in image reconstruction, and zone $S_2$ can be considered an aliasing-free region.

Due to the finite duration of the ultrasonic transducer's temporal response, the function $$\left(1 - \left(t + \frac{\|r'_m - r_n\|}{c}\right)\frac{\partial}{\partial t}\right)h'_e(t)$$

has a nonzero value only when t is within a finite interval, denoted as $T_e$. The broader the bandwidth of $h_e(t)$, the shorter $T_e$. When $$\frac{\|r'' - r\|}{c} - \frac{\|r' - r\|}{c}$$

is out of $T_e$, signals from source point r' that are detected by the element at r have no contribution to the reconstruction at r''.

Assuming that $$\frac{\|r'' - r\|}{c} - \frac{\|r' - r\|}{c}$$

belongs to $T_e$, and with source points inside $S_2$, there may still be aliasing for reconstruction locations in a region outside zone $S_2$, but inside zone $S_1$. For example, where both r'' and r' are on the boundary of $S_2$, and the length of the step size of $\|r-r\|-\|r'-r\|$ achieves the maximum value of $$\frac{2\pi R(\cos\alpha'' - \cos\alpha')}{N} = \frac{\lambda_c}{2},$$

there may be aliasing outside zone $S_2$, but inside zone $S_1$. In this example, $\alpha''$ and $\alpha'$ denote the angles formed by the line segments r-r'' and r-r', respectively, with the tangential dotted line that is perpendicular to r.

As shown in FIG. 1B, the reconstruction location r'' is moved to a new position $r_1''$ outside $S_2$, but inside $S_1$. The distance $\|r_1''-r\|=\|r''-r\|$ is kept constant and thus, $$\frac{\|r''_1 - r\|}{c} - \frac{\|r' - r\|}{c} = \frac{\|r'' - r\|}{c} - \frac{\|r' - r\|}{c}$$

still belongs to $T_e$. As r'' moves to $r_1''$, the angle $\alpha''$ decreases to $\alpha_1''$. Both $\alpha''$ and $\alpha_1''$ belong to $$\left(0, \frac{\pi}{2}\right),$$

then $\cos \alpha_1''$: >$\cos \alpha''$. Thus, for the local step size of $\|r_1''-r\|-\|t''-r\|$, there is the estimation $$\frac{2\pi R(\cos\alpha_1'' - \cos\alpha')}{N} > \frac{2\pi R(\cos\alpha'' - \cos\alpha')}{N} = \frac{\lambda_c}{2},$$

which means that spatial aliasing appears in image reconstruction. Switching the source point and reconstruction locations, the analysis is repeated and a similar conclusion is drawn: with source points inside zone $S_1$, but outside zone $S_2$, spatial aliasing may occur when doing reconstruction.

FIG. 1C illustrates an example of the relative sizes of the three zones: (1) the two-way Nyquist zone $S_2$, (2) one-way Nyquist zone, $S_1$, with no spatial aliasing due to spatial sampling, and (3) detection zone, $S_0$, with spatial aliasing due to spatial sampling and image reconstruction. The zones $S_0$, $S_1$, and $S_2$ can be defined by Eqn. 9, Eqn. 16, and Eqn. 22 respectively. Spatial aliasing due to spatial sampling do not appear for source points and reconstruction locations inside one-way Nyquist zone $S_1$ (e.g., zone $S_1$, 102, FIG. 1C), but do appear for objects outside one-way Nyquist zone, $S_1$. Spatial aliasing in image reconstruction does not appear for source points of objects and reconstruction locations inside two-way Nyquist zone $S_2$, (e.g., zone $S_2$, 102, in FIG. 1C), but appears for other combinations of objects and image reconstruction locations.

Figure 2A:
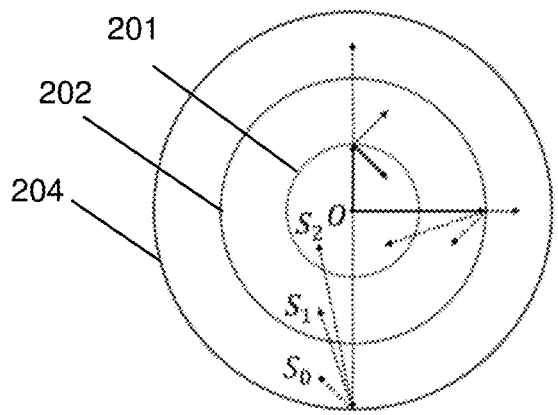
FIG. 2A is a schematic diagram depicting spatial aliasing appearing during image reconstruction in a PACT system with spatiotemporal antialiasing with a full-ring ultrasonic transducer array, according to one implementation.
Figure 2B:
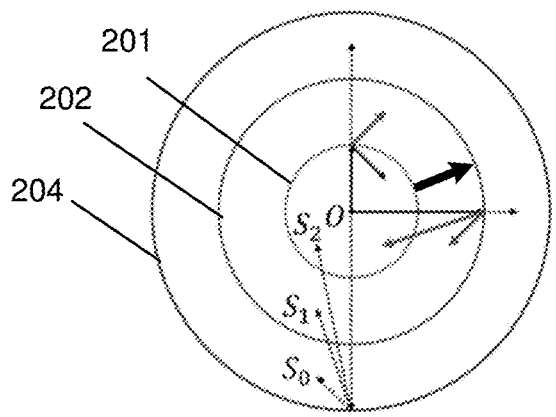
FIG. 2B is a schematic diagram representing mitigating spatial aliasing in image reconstruction using spatial interpolation, according to an implementation.
Figure 2C:
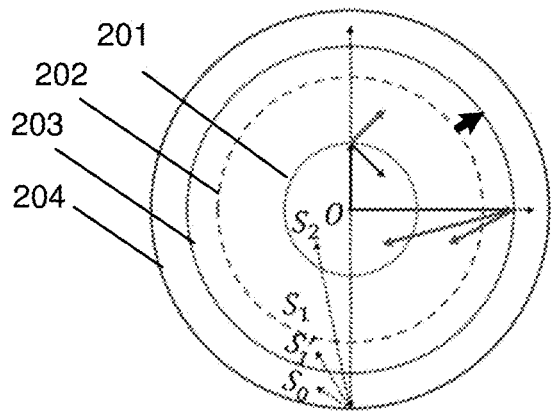
FIG. 2C is a schematic diagram representing mitigating spatial aliasing in spatial sampling using location-dependent temporal filtering, according to an implementation.

FIGS. 2A, 2B, and 2C are schematic diagrams of different combinations of source points and image reconstruction locations in the imaging domain of a full-ring ultrasonic array that are subject to no spatial aliasing or spatial aliasing due to spatial sampling and/or image reconstruction, according to certain aspects. The diagrams include a two-way Nyquist zone $S_2$ 201, an initial one-way Nyquist zone $S_1$ 202, and an imaging domain $S_0$ 204. The outer boundary of the imaging domain $S_0$ 204 represents the detection surface of the full-ring transducer array having a radius R and having N evenly-distributed transducer elements. The center O of the imaging domain $S_0$ 204 represents the origin of a coordinate system used in image reconstruction. The first line radiating from the origin O represents the range of source locations for spatial sampling, while the second line radiating from the tip of the first line represents the range of reconstruction locations for image reconstruction. A solid line means no aliasing, while a dotted line means aliasing. The boundaries for the zones $S_0$, $S_1$, and $S_2$ may be defined by Eqn. 9, Eqn. 16, and Eqn. 22 respectively.

FIG. 2A is a schematic diagram depicting spatial aliasing appearing during image reconstruction (e.g., image reconstruction that uses universal back projection) in a PACT system with a full-ring ultrasonic transducer array, according to one implementation. FIG. 2A illustrates three zones (regions): (1) an innermost two-way Nyquist zone, $S_2$, which is an aliasing-free region (2) a one-way Nyquist zone, $S_1$, does not have spatial aliasing due to spatial sampling, and (3) a detection zone, $S_0$, that has spatial aliasing in spatial sampling and in image reconstruction.

FIG. 2B is a schematic diagram representing mitigating spatial aliasing in image reconstruction using spatial interpolation, according to an implementation. The large arrow enlarging two-way Nyquist zone $S_2$ 201 to zone $S_1$ 202 depicts the mitigation resulting from spatial interpolation. In this example, spatial interpolation is shown to eliminate spatial aliasing in the three instances of image reconstruction, extending the two-way Nyquist zone $S_2$ to the one-way Nyquist zone $S_1$ to provide a larger aliasing-free region. This mitigation of spatial aliasing in image reconstruction is represented by the change from the dotted lines in the three instances in FIG. 2A to the solid lines in FIG. 2B.

FIG. 2C is a schematic diagram representing mitigating spatial aliasing in spatial sampling using location-dependent temporal filtering, according to an implementation. The large arrow depicts the extension of zone $S_1$ 202 to zone $S_1'$ 203 due to mitigation based on location-dependent temporal filtering. Location-dependent temporal filtering extends (adjusts) the initial one-way Nyquist zone $S_1$ to a larger adjusted one-way Nyquist zone $S_1'$. By further applying spatial interpolation to this example, the zone $S_1'$ becomes an aliasing-free region. As can be seen, zone $S_1'$ 203 is not extended all the way to edge zone $S_0$ 204 in order to maintain high resolution imaging.

In certain implementations, location-dependent temporal filtering extends (adjusts) an initial one-way Nyquist zone $S_1$ to a larger adjusted one-way Nyquist zone $S_1'$ that does not cover the area of the entire two-way Nyquist zone $S_0$. In one example, the one-way Nyquist zone $S_1'$ covers an area that is more than 95% of the area of the two-way Nyquist zone $S_0$. In one example, the one-way Nyquist zone $S_1'$ covers an area that is more than 90% of the area of the two-way Nyquist zone $S_0$. In one example, the one-way Nyquist zone $S_1'$ covers an area that is more than 80% of the area of the two-way Nyquist zone $S_0$. In one example, the one-way Nyquist zone $S_1'$ covers an area that is in a range from about 80% to 100% of the area of the two-way Nyquist zone $S_0$.

C. PACT Systems and Methods with Spatiotemporal Antialiasing

In certain aspects, PACT systems and methods with spatiotemporal antialiasing mitigate (substantially reduce or eliminate) spatial aliasing in image reconstruction using spatial interpolation and mitigate spatial aliasing in spatial sampling using a location-dependent temporal filtering technique. The location-dependent temporal filtering is designed based on the geometry of the ultrasonic transducer array being implemented. For example, in one implementation, it is determined whether a distance between the reconstruction location and the transducer array is within or outside a first distance or radius from the transducer array in a one-way Nyquist zone where spatial aliasing does not occur and then only apply location-based temporal filtering if the reconstruction location is outside the one-way Nyquist zone. According to one aspect, the location-dependent temporal filtering technique is designed to both maintain high resolution of the images being reconstructed while substantially mitigating spatial aliasing due to undersampling.

Spatial aliasing solely in image reconstruction, but not in spatial sampling, can be mitigated using spatial interpolation. For example, without spatial aliasing, spatially continuous photoacoustic signals can be accurately recovered from spatially discrete photoacoustic signals (e.g., digitized signals from one or more DAQs) through, e.g., Whittaker-Shannon spatial interpolation. In one aspect, if there is no spatial aliasing in spatial sampling, a PACT method implements spatial interpolation and no spatial aliasing occurs in reconstructing the image using spatially continuous photoacoustic signals.

1. Spatiotemporal Antialiasing for Circular Transducer Arrays (e.g., Full-Ring Array)

Although this section uses a circular transducer array as an example, one or more of the operations discussed in this section may also apply to a linear array or other array geometry. In one aspect, PACT methods with spatiotemporal antialiasing include image reconstruction operations that utilize spatial interpolation with an operation that numerically increases the number of detection elements in the transducer array. At any given time, t, a function sampled at $$\theta_n = \frac{2\pi n}{N},$$

n=0, 1, 2, ..., N−1 may be defined as:

$$f_R(\theta) = \hat{p}(r;t), \quad \text{(Eqn. 23)}$$

where r=(R cos θ, R sin θ), θ∈[0,2π). Referring to FIG. 1C, for objects inside zone $S_1$, there is no aliasing in spatial sampling. The function $f_R(\theta)$ can be recovered from $f_R(\theta_n)$, n=0, 1, 2, ..., N−1 through spatial interpolation such as, e.g., the Whittaker-Shannon spatial interpolation. To extend the aliasing-free region $S_2$ to a larger $S_2'$, the number of detection (transducer) elements may be numerically doubled from N'=2N during a spatial interpolation operation. Substituting N' for N in Eqn. 22, a larger aliasing-free region $S_2'$ is obtained:

$$S_2' = \left\{ r' \mid \|r'\| < \frac{N'\lambda_c}{8\pi} \right\} = \left\{ r' \mid \|r'\| < \frac{N\lambda_c}{4\pi} \right\} = S_1. \quad \text{(Eqn. 24)}$$

With source and reconstruction locations inside $S_2'$, image reconstruction has no aliasing. Since $S_1 = S_2'$, the spatial interpolation operation mitigated spatial aliasing in image reconstruction. For source points outside one-way Nyquist zone, $S_1$, spatial sampling has aliasing, and spatial interpolation cannot recover the lost information. The spatial aliasing in spatial sampling may be mitigated by temporal lowpass filtering, which expands zone $S_1$ to a larger region of zone $S_1'$:

$$S_1' = \{r'' \mid \|r''\| < r'\} \text{ with } r' > \frac{N\lambda_c}{4\pi}. \quad \text{(Eqn. 25)}$$

In certain aspects, PACT systems/methods with spatiotemporal antialiasing perform one or more location-dependent temporal filleting operations before performing spatial interpolation and image reconstruction operations. The one or more location-dependent temporal filtering operations process the photoacoustic signals using one or more lowpass filters with an upper cutoff frequency. In one aspect, one or more location-dependent temporal filtering operations apply an antialiasing filter with one or more lowpass filters having an upper cutoff frequency of $$f_c' = \frac{Nc}{4\pi r'}$$

where N is the number of elements in the transducer array, c is the speed of sound, r' is the distance between the center of the transducer array and the reconstruction location. By Replacing $\lambda_c$ in Eqn. 16 with $$\lambda_c' = \frac{c}{f_c'},$$

the zone $S_1$ is extended to:

$$S_1' = \left\{ r'' \mid \|r''\| < \frac{N\lambda_c'}{4\pi} \right\} = \{r'' \mid \|r''\| < r'\}. \quad \text{(Eqn. 26)}$$

By applying spatial interpolation during image reconstruction, for source points inside $S_1'$, any points inside $S_1'$ of an image can be reconstructed without aliasing artifacts.

This one-way Nyquist zone $S_1'$ may be further extended through temporal lowpass filtering. In one example, spatial antialiasing may extend the zone $S_1'$ depicted in FIG. 2C to the whole region $S_0$ by applying an antialiasing filter with one or more lowpass filters having an upper cutoff frequency of $$f_c' = \frac{Nc}{4\pi r'}.$$

Directly extending $S_1'$ to $S_0$ may, however, compromise image resolution. Since lowpass filtering removes high-frequency signals (i.e. with frequencies above the upper cutoff frequency), reconstructed images may be blurred if an upper cutoff frequency of $$f_c' = \frac{Nc}{4\pi r'}$$

is used.

In certain implementations, PACT systems/methods with spatial antialiasing implement location-dependent temporal filtering that balances image resolution with reducing aliasing from spatial sampling to extend the zone $S_1$. To reconstruct the image at $r' \in S_0$, these PACT systems/methods including an antialiasing filter with one or more lowpass filters that are designed based at least in part on the distance $r' = \|r'\|$ of an object of interest being imaged at an imaging plane) to the center of the transducer array.

For example, the PACT methods may include one or more location-dependent temporal filtering operations. During these operations, it is determined whether $$r' < \frac{N\lambda_c}{4\pi},$$

where N is the number of elements in the transducer array, $\lambda_c$ is the lower cutoff wavelength, and $r'$ is the distance between the center of the transducer array and the imaging location. In the region where $$r' < \frac{N\lambda_c}{4\pi},$$

there is no spatial aliasing in spatial sampling. If it is determined that $$r' < \frac{N\lambda_c}{4\pi},$$

spatial interpolation is applied and then image reconstruction is performed. If it is determined that $$r' \geq \frac{N\lambda_c}{4\pi},$$

the photoacoustic signals are filtered first with an antialiasing filter having one or more low pass filters with an upper cutoff frequency of $$f_c' = \frac{Nc}{4\pi r'},$$

and then spatial interpolation is applied, and then image reconstruction. N is the number of elements in the transducer array, c is the speed of sound, r' is the distance between the center of the transducer array and the reconstruction location.

2. Spatiotemporal antialiasing for Linear Transducer Arrays

Figure 3:
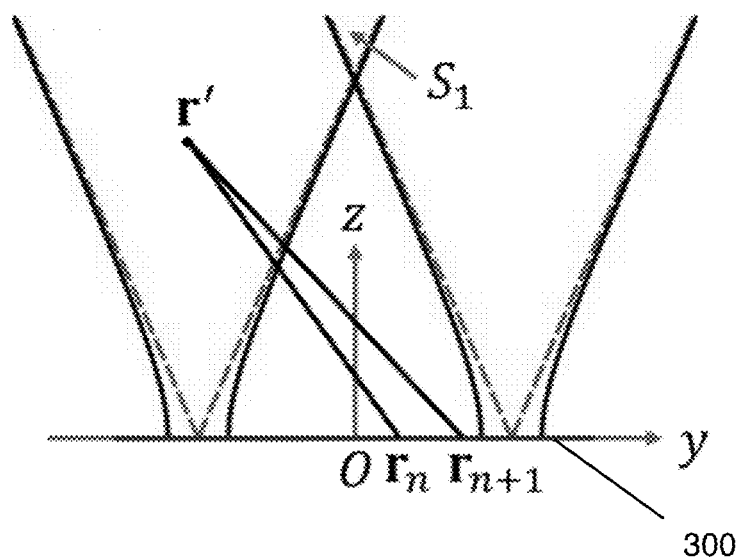
FIG. 3 is a schematic illustration of a portion of a surface of a linear ultrasonic transducer array, according to an implementation.

In another aspect, a PACT system with spatiotemporal antialiasing includes a linear array with N (e.g., N≥4) transducer elements, a pitch d, and a lower cutoff wavelength $\lambda_c < 2d$. (e. g., N≥4). FIG. 3 is a schematic illustration of a portion of a surface of a linear ultrasonic transducer array 300 with N elements and pitch d, according to an implementation. The illustration shows a center O of the linear ultrasonic transducer array 300. A Cartesian coordinate is formed with the array's center O as the origin, the array direction as a y-axis, and its normal vector as a z-axis. Two adjacent ransducer element locations $r_n$, $r_{n+1}$, and a source point location r' are also shown. Two symmetric hyperbolas (with sampling step size $$\frac{\lambda_c}{2})$$

with z≥0 are shown as solid curves and their asymptotes as dashed lines. The one-way Nyquist zone $S_1$ is formed by the points above the two asymptotes crossing z-axis.

Figure 4:
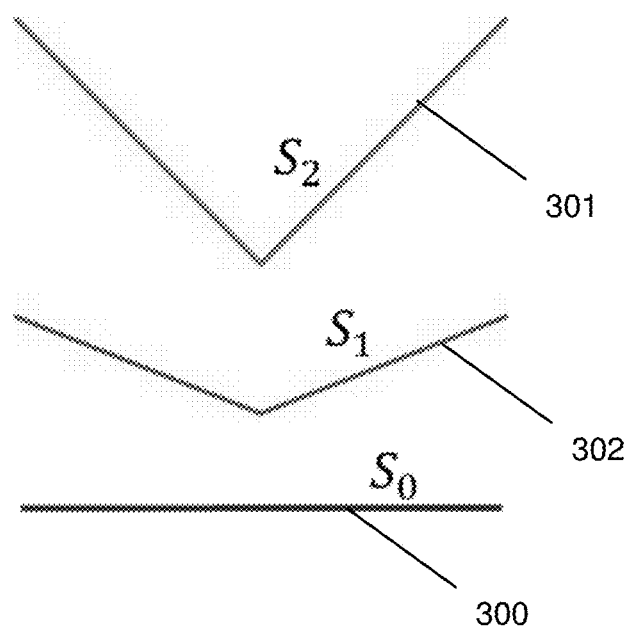
FIG. 4 is a schematic illustration of the portion of the linear ultrasonic transducer array in FIG. 3 depicting the imaging domain $S_0$, the one-way Nyquist zone $S_1$, and the two-way Nyquist zone $S_2$, according to an aspect.

FIG. 4 is a schematic illustration of the portion of the surface of the linear ultrasonic transducer array 300 in FIG. 3 depicting the imaging domain $S_0$, the one-way Nyquist zone $S_1$, and the two-way Nyquist zone $S_2$ outlined with three lines, respectively. The illustration includes outlined boundaries 302, 301 of the one-way Nyquist zone $S_1$, and the two-way Nyquist zone $S_2$, respectively.

Using the linear array center O as the origin, the linear transducer array 300 as one axis and its normal as another axis, a cartesian coordinate can be constructed as shown in FIG. 3. For a source point location r'=(y, z) and two adjacent element locations $$r_n = \left(\left(n - \frac{N-1}{2}\right)d, 0\right) \text{ and } r_{n+1} = \left(\left(n - \frac{N-3}{2}\right)d, 0\right),$$

n=0, . . . , N−2, the sampling step size can be expressed as:

$$\|\|r' - r_n\| - \|r' - r_{n+1}\|\| = \left|\sqrt{z^2 + \left(y - \left(n - \frac{N-1}{2}\right)d\right)^2} - \sqrt{z^2 + \left(y - \left(n - \frac{N-3}{2}\right)d\right)^2}\right|. \quad \text{(Eqn. 27)}$$

The sampling step size is $$\frac{\lambda_c}{2}$$

$$\| r' - r_n \| - \| r' - r_{n+1} \| | = \frac{\lambda_c}{2}, \quad \text{(Eqn. 28)}$$

which is a hyperbola with a standard form:

$$\frac{\left(y - \left(n - \frac{N-2}{2}\right)d\right)^2}{\left(\frac{\lambda_c}{4}\right)^2} - \frac{z^2}{\left(\frac{d}{2}\right)^2 - \left(\frac{\lambda_c}{4}\right)^2} = 1. \quad \text{(Eqn. 29)}$$

For any source points (e.g., $r_n$, $r_{n+1}$) that lie in between the two curves of this hyperbola, the spatial Nyquist criterion given by:

$$\| \| r' - r_n \| - \| r' - r_{n+1} \| \| < \frac{\lambda_c}{2}, \quad \text{(Eqn. 30)}$$

is satisfied. Based on this geometry, the spatial Nyquist criterion for all transducer element pairs can be simplified into two cases: the leftmost one $$\| \| r' - r_0 \| - \| r' - r_1 \| \| < \frac{\lambda_c}{2},$$

and the rightmost one $$\| \| r' - r_{N-2} \| - \| r' - r_{N-1} \| \| < \frac{\lambda_c}{2},$$

Illustrations of these two hyperbolas with $z \geq 0$ are shown in FIG. 3 as solid line curves and their asymptotes are shown as dashed lines. Due to the symmetry between these the two hyperbolas, they intersect with z axis at the same point $$(0, z_1') = \left(0, \sqrt{\left(\left(\frac{2d}{\lambda_c}\right)^2 - 1\right)\left(\left(\frac{N-2}{2}d\right)^2 - \left(\frac{\lambda_c}{4}\right)^2\right)}\right),$$

while their asymptotes intersect with the z axis at:

$$(0, z_1) = \left(0, \frac{N-2}{2} d \sqrt{\left(\frac{2d}{\lambda_c}\right)^2 - 1}\right). \quad \text{(Eqn. 31)}$$

The one-way Nyquist zone can be approximated by:

$$S_1 = \left\{ (y, z) \mid z > \max\left\{ \left| y - \frac{N-2}{2} d \right|, \left| y + \frac{N-2}{2} d \right| \right\} \sqrt{\left(\frac{2d}{\lambda_c}\right)^2 - 1} \right\}, \quad \text{(Eqn. 32)}$$

which is the region above the two intersecting asymptotes, as shown in FIG. 3. At y=0, the approximation error achieves the maximum value:

$$|z_1 - z_1'| \leq \frac{\left(\frac{\lambda_c}{4}\right)^2 \sqrt{\left(\frac{2d}{\lambda_c}\right)^2 - 1}}{\sqrt{(N-2)^2 d^2 - \left(\frac{\lambda_c}{2}\right)^2}} < \frac{\left(\frac{\lambda_c}{4}\right)^2 \sqrt{\left(\frac{2d}{\lambda_c}\right)^2 - 1}}{d \sqrt{(N-1)(N-3)}}. \quad \text{(Eqn. 33)}$$

For example, if c=1.5 mm·μs$^{-1}$, $f_c$=4.5 MHz, N=256, and d=0.25 mm, $z_1 \approx 35.5$ mm and $$\frac{2|z_1 - z_1'|}{\lambda_c} < 7.4 \times 10^{-4},$$

which proves the accuracy of using $S_1$ as the one-way Nyquist zone. Further, the two-way Nyquist zone may be approximated using:

$$S_2 = \left\{ (y, z) \mid z > \max\left\{ \left| y - \frac{N-2}{2} d \right|, \left| y + \frac{N-2}{2} d \right| \right\} \sqrt{\left(\frac{4d}{\lambda_c}\right)^2 - 1} \right\}, \quad \text{(Eqn. 34)}$$

The PACT system with spatiotemporal antialiasing can implement spatial interpolation to extend $S_2$ to $S_1$, and location-dependent temporal filtering can be implemented to further extend $S_1$.

III. Examples of PACT Systems and Methods with Spatiotemporal Antialiasing

A. Examples of PACT Systems with Spatiotemporal Antialiasing

Figure 5:
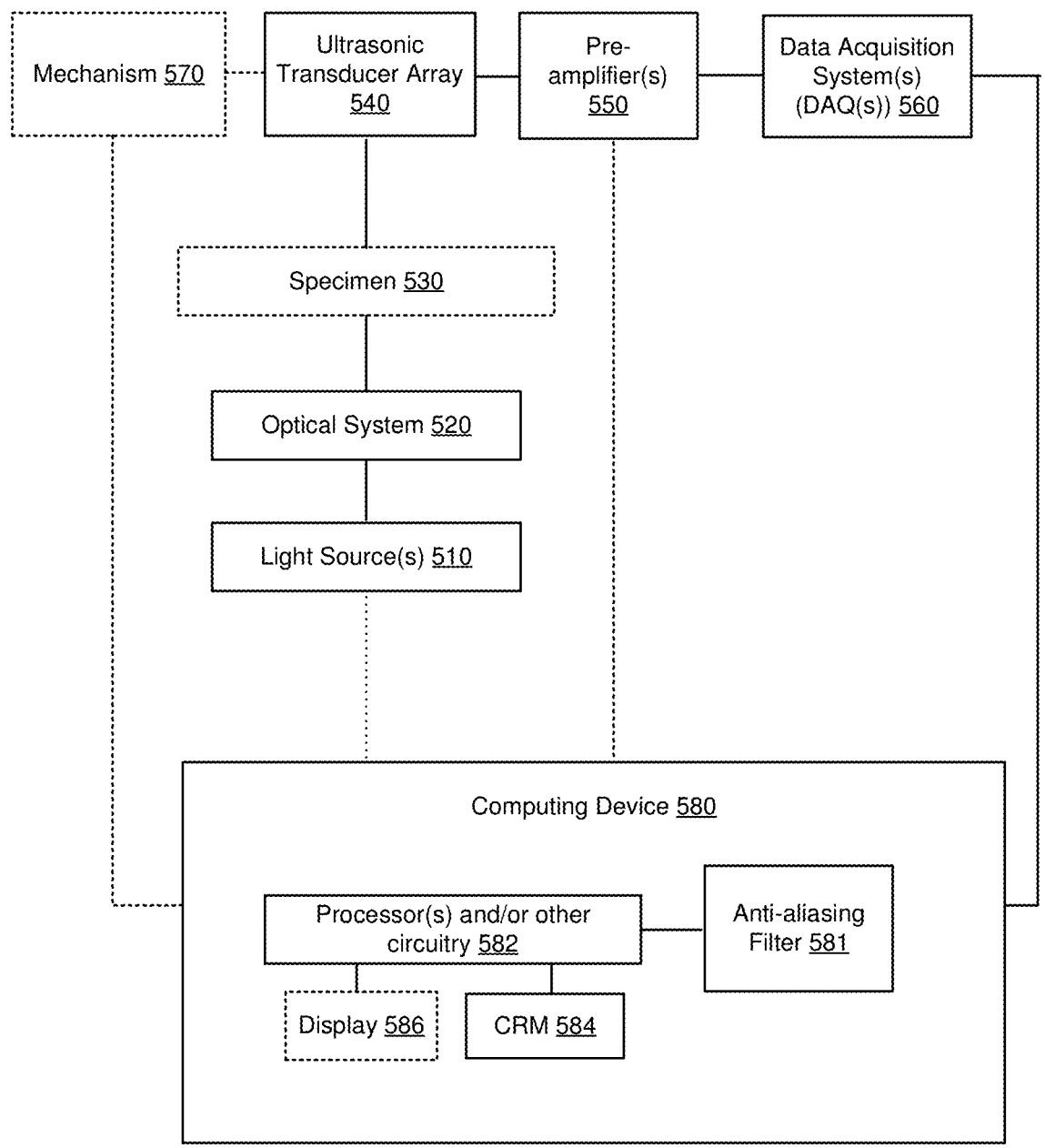
FIG. 5 is a schematic diagram of components of a PACT system with spatiotemporal antialiasing, according to certain implementations.

FIG. 5 is a schematic diagram of components of a PACT system with spatiotemporal antialiasing 500, according to certain implementations. The PACT system with spatiotemporal antialiasing 500 includes one or more light sources 510 (e.g., a pulsed laser) that provide illumination (e.g., generate pulsed or modulated light) and an optical system 520 having one or more optical components configured to propagate the illumination from the one or more light sources to a specimen 530 during operation. At the instant in time shown in FIG. 5, the specimen 530 is at a location at which it can receive the illumination during operation. It would be understood that at other times the specimen 530 may not be at this location as denoted by the dotted line.

The optical system 520 includes one or more optical components (e.g., lens(es), optical filter(s), mirror(s), beam steering device(s), beam-splitter(s), optical fiber(s), relay(s), and/or beam combiner(s)) configured to propagate and/or alter light from the one or more light sources 510 to provide the illumination to the specimen 530. The optical system 520 is in optical communication with the one or more light sources 510 to receive illumination during acquisition. In one aspect, the optical system 520 is configured to convert a light beam from the one or more light sources 510 into shaped illumination such as donut-shaped illumination (sometimes referred to herein as "donut illumination" or a "donut beam"). Donut-shaped illumination and other circular illumination may be generated by employing an engineered diffuser such as, e.g., an EDC15 diffuser made by RPC Photonics®.

In some implementations, a PACT system with spatiotemporal antialiasing includes one or more light sources (e.g., a pulsed laser) that can generate pulsed or modulated illumination such as, e.g., pulsed or modulated light at a near-infrared wavelength or a narrow band of near-infrared wavelengths. For example, a light source may be a pulsed laser that can generate near infrared pulses having a wavelength or narrow band of wavelengths in a range from about 700 nm to about 1000 nm. As another example, a light source may be a pulsed laser that can generate near infrared pulses having a wavelength or narrow band of wavelengths in a range from about 600 nm to about 1100 nm. In yet another example, a light source may be a pulsed laser that can generate near infrared pulses with a wavelength or narrow band of wavelengths greater than 760 nm. In yet another example, a light source may be a pulsed laser that can generate near infrared pulses with a wavelength or narrow band of wavelengths greater than 1000 nm. In another example, a light source may be a pulsed laser that can generate a 1064-nm laser beam. A commercially-available example of a suitable pulsed laser is the PRO-350-10, Quanta-Ray® laser with a 10-Hz pulse repetition rate and 8 ns-12 ns pulse width sold by Spectra-Physics®. The low optical attenuation of 1064 nm light or other near infrared light can be used to deeply penetrate to, e.g., a depth of 4 cm, into biological tissues. Imaging of biological tissues using near infrared light is discussed in Smith, A. M., Mancini, M. C. & Nie, S., "Bioimaging: second window for in vivo imaging," Nat. Nanotechnol. 4, 710-711 (2009), which is hereby incorporated by reference in its entirety. Alternatively, a light source may be a continuous wave laser source that is chopped, modulated and/or gated. In implementations that include a light source in the form of a pulsed laser, the pulse repetition rate may be about 10-Hz in some cases, about 20-Hz in other cases, about 50-Hz in other cases, and about 100-Hz in other cases. In another case, the pulse repetition rate is in a range from about 10-Hz to about 100-Hz.

In one aspect, the one or more light sources of a PACT system with spatiotemporal antialiasing include a tunable narrow-band pulsed laser such as, e.g., one of a quantum cascade laser, an interband cascade laser, an optical parametric oscillator, or other pulsed laser that can be tuned to different narrow bands (e.g., a near-infrared band). In another aspect, the one or more light sources may include a pulsed laser of a single wavelength or approximately a single wavelength. In another aspect, the one or more light sources may include multiple lasers of the same type. For example, multiple lasers of the same type may be used where each of the lasers has a lower power. In another aspect, the one or more light sources may include a combination of different types of lasers. For example, an optical parametric oscillator combined with an Nd:YAG laser may be used in one implementation.

In one aspect, the optical system is configured to a light beam from the one or more light sources into shaped illumination, e.g., a donut beam that may be used to circumferentially illuminate the specimen. For example, the optical system may include an axicon lens (e.g., an axicon lens having 25 mm diameter and a 160° apex angle) followed by an engineered diffuser (e.g., EDC-10-A-2s made by RPC Photonics) to convert a light beam from the one or more light sources into a donut beam. The axicon lens may be positioned to receive a single laser beam propagated from a pulsed laser source and may be configured to convert the beam into a ring having a thickness and diameter and the engineered diffuser may be configured to expand the ring into a donut beam. The donut beam may be used to provide mass energy in homogenized, uniform illumination deep into tissue. An example of a technique for generating donut-shaped illumination can be found in U.S. patent application Ser. No. 16/464,958, titled "SINGLE-IMPULSE PANORAMIC PHOTOACOUSTIC COMPUTED TOMOGRAPHY (SIP-PACT)," and filed on Nov. 29, 2017, which is hereby incorporated by reference in its entirety.

Returning to FIG. 5, the PACT system with spatiotemporal antialiasing 500 also includes an ultrasonic transducer array 540 for sampling photoacoustic waves, an optional mechanism 570 for moving (translating and/or rotating) the ultrasonic transducer array 540, one or more pre-amplifiers 550 for boosting (increasing amplitude) photoacoustic signals communicated from the ultrasonic transducer array 540, one or more data acquisition systems (DAQs) 560 for digitizing the one or more boosted photoacoustic signal, and a computing device 580 for receiving the digitized photoacoustic data from the DAQ(s) 560. The computing device 580 includes an antialiasing filter 581 including one or more lowpass filters that can perform location-dependent temporal filtering of the digitized photoacoustic data communicated from the DAQ(s) 560. The computing device 580 also includes one or more processors and/or other circuitry 582 in electrical communication with the anti-aliasing filter 581 to receive photoacoustic data and configured to perform operations such as spatial interpolation and image reconstruction, an optional (denoted by dotted line) display 586 in electrical communication with the one or more processors and/or other circuitry 582, and a computer readable media 584. The computing device 580 may also communicate one or more control signals to the antialiasing filter 581 to control the upper cutoff frequency or to trigger temporally filtering. For example, the computing device 580 may execute instructions with logic that determine whether the distance between the center of the ultrasonic transducer array and the reconstruction location, r' is less than $$\frac{N\lambda_c}{4\pi}$$

where N is the number of elements in the transducer array $$\left(r' < \frac{N\lambda_c}{4\pi}\right),$$

$\lambda_c$ is the lower cutoff wavelength, and r' is the distance between the center of the transducer array and the reconstruction location. If it is determined that r' is less than $$\frac{N\lambda_c}{4\pi},$$

then spatial interpolation operation(s) are applied and image reconstruction performed without temporal filtering. If it is determined that. If r' is greater than or equal to $$\frac{N\lambda_c}{4\pi},$$

then an upper cutoff frequency is determined based on the geometry of the ultrasonic transducer array. For example, the upper cutoff frequency may be calculated as $$f_c' = \frac{Nc}{4\pi r'},$$

where N is the number of elements in the transducer array, c is the speed of sound, r is the distance between the center of the transducer array and the imaging plane. The computing device may then send control signals to trigger the anti-aliasing filter to temporally filter the photoacoustic data. In one example, cutoff frequencies of 3.8 Hz or smaller are used. In other examples, a cutoff frequency in a range between about 1.5 Hz (low frequency transducer used for transcranial human brain imaging) to about 40 MHz (high frequency transducer used for superficial tissue imaging) may be used. In one implementation, a GPU will be used for acceleration of both location-dependent temporal filtering and image reconstruction.

In certain implementations, the PACT system with spatiotemporal antialiasing includes an antialiasing filter (e.g., anti-aliasing filter 581 in FIG. 5) including one or more lowpass filters for location-dependent temporal filtering one or more photoacoustic signals from the DAQ(s). The antialiasing filter may include a single lowpass filter or a combination of the same type or different types of lowpass filters. Some examples of lowpass filters that be implemented include a Butterworth filter, a Cheyshev filter and a Bessel filter. The antialiasing filter is in electrical communication with the one or more DAQs of the PACT system to receive digitized photoacoustic data and remove frequency components with frequencies higher than an upper cutoff frequency $f_c$ from digitized data communicated from the DAQ(s). The antialiasing filter may be a component of a computing device, a component of the controller, a component of one of the one or more DAQs, part of another system component, or a standalone device. Examples of one or more operations that can be used to perform location-dependent temporal filtering are described in Section III(B).

Returning to FIG. 5, the ultrasonic transducer array 540 is coupled or otherwise in acoustic communication with the specimen 530 to be able to receive one or more photoacoustic waves induced by the illumination from the one or more light sources 510 and output and/or record one or more photoacoustic signals. The one or more pre-amplifiers 550 are in electrical communication (directly or via other circuitry) with the ultrasonic transducer array 540 to receive one or more photoacoustic signals. The pre-amplifier(s) 550 can boost one or more photoacoustic signals received and output boosted photoacoustic signals. The DAQ(s) 560 is configured to process the photoacoustic signals, for example, digitize and/or record the digitized photoacoustic data. The DAQ(s) 560 may include at least one digitizer to digitize the signals.

During operation, the ultrasonic transducer array 540 is coupled to or otherwise in acoustic communication with the specimen 530 during signal acquisition. In some cases, an acoustic medium such as an acoustic gel, water, or other medium capable of conveying ultrasound pulses, is provided at least partially between the specimen 530 and the ultrasonic transducer array 540. In other cases, the acoustic medium may be omitted. The ultrasonic transducer array 540 is acoustically coupled to the specimen 530 to be able to detect photoacoustic waves induced by illumination and sample photoacoustic signals. These photoacoustic signals are indicative of the optical absorption of the specimen by the illumination. In one implementation, the PACT system with spatiotemporal antialiasing may also include a tank that is at least partially filed with acoustic medium such as a water tank (e.g., an acrylic water tank). The specimen being imaged may be located directly in the acoustic medium or in a portion of the tank that is submerged or otherwise located in the acoustic medium.

The ultrasonic transducer array 540 includes a plurality of N transducers (sometimes referred to herein as "transducer elements") operable to collect photoacoustic signals, e.g., in parallel. Each transducer element has an aperture (e.g., a flat-rectangular aperture). The transducer elements have a height, a width, and a pitch. In one case, the pitch is about 1.35 mm. In one case, the width is 0.65 mm. In another case, the pitch is in a range of 1.20 mm to 1.50 mm. In another case, the height is about 5 mm. In another case, the height is in a range of 2 mm to 10 mm. The N transducer elements in the ultrasonic transducer array 540 are arranged in, e.g., a circular array such as a full-ring array, a linear array, or a two-dimensional array. In one implementation, a full-ring ultrasonic transducer array is employed, e.g., to be able to provide panoramic detection. In this case, the full-ring ultrasonic transducer array (e.g., a 512-element full-ring ultrasonic transducer) includes transducer elements distributed along the circumference of a ring having a diameter and an inter-element spacing. The ring diameter may be at least 220 mm in one aspect, may be at least 200 mm in one aspect, or may be at least 250 mm in one aspect. In one aspect, the ring diameter is in a range of about 150 mm to about 400 mm. The inter-element spacing may be less than or equal to about 1.0 mm in one aspect, less than or equal to 0.7 mm in one aspect, less than or equal to 1.5 mm in one aspect, or less than or equal to 2.0 mm in one aspect. In one aspect, the inter-element spacing is in a range of 0 mm to about 5 mm.

In one aspect, the ultrasonic transducer array includes one or more unfocused transducer elements. One or more of the unfocused transducer elements may have a diffraction angle of about 10 degrees in one case, a diffraction angle in a range of about 5 degrees to about 30 degrees in another case, a diffraction angle of about 20 degrees in another case, a diffraction angle in a range of about 5 degrees to about 30 degrees in another case. In one case, each of the unfocused transducer elements has a central frequency in a range of 0.50 MHz to 2.25 MHz and a one-way bandwidth of more than 50%. In another aspect, each of the unfocused transducer elements has a central frequency in a range of 2.25 MHz to 10 MHz and a one-way bandwidth of more than 50%.

Returning to FIG. 5, the PACT system 500 includes an optional (denoted by dashed line) mechanism 570 coupled to or otherwise operably connected to the ultrasonic transducer array 540 to be able to move (translate and/or rotate) the ultrasonic transducer array 540 to one or more positions during operation, e.g., along an axis in one or both directions. For example, the mechanism 570 may be able to move ultrasonic transducer array 540 to two or more different positions along an axis (e.g., between $z_1$ and $z_2$ along a z-axis). In addition, the mechanism 570 may be able to hold the ultrasonic transducer array 540 at each position for a period of time. Some examples of time periods that may be used include about 10 seconds, about 15 seconds, and about 20 seconds. In one case, the time period may be in a range from about 10 seconds to about 20 seconds. The step size between positions may be defined by the elevational resolution of the 2d reconstructed image for the PACT implementation being used. For example, if the elevational resolution is 3-4 cm thick, the step size may be 3-4 cm. An example of a commercially-available mechanism for linear movement is a linear stage KR4610D made by THK America, Inc.

The one or more DAQ(s) 560 record photoacoustic signals at time intervals defined by a sampling frequency. In one example, the sampling frequency is in a range from about 4 MHz to about 100-Hz. In another example, the sampling frequency is 40 MHz.

According to one aspect, the one or more DAQs and one or more pre-amplifiers of a PACT system provide one-to-one mapped associations with the transducers in the ultrasonic transducer array. These one-to-one mapped associations allow for fully parallelized data acquisition of all ultrasonic transducer channels and avoids the need for multiplexing after each laser pulse excitation or other modulated or pulsed excitation illumination. With one-to-one mapped associations between pre-amplifiers and transducer elements, each ultrasound transducer element in the array is in electrical communication with one dedicated pre-amplifier channel (also referred to as "preamp channel"). The one dedicated pre-amplifier channel is configured to amplify only photoacoustic signals detected by the one associated/mapped ultrasound transducer. These one-to-one mapped associations between the transducers and the pre-amplifier channels allow for parallelized pre-amplification of the photoacoustic signals detected by the plurality of transducers in the ultrasound transducer array. With one-to-one mapped analog-to-digital sampling, each pre-amplifier is operatively coupled to a corresponding dedicated data channel of an analog-to-digital sampling device in a DAQ to enable parallelized analog-to-digital sampling of the plurality of pre-amplified PA signals. The pre-amplified PA signals produced by each individual preamp channel are received by a single dedicated data channel of the at least one analog-to-digital sampling devices. Any suitable number of pre-amplifier devices and/or DAQ devices may be used to provide the one-to-one mapping. For example, a PACT system may include four 128-channel DAQs (e.g., SonixDAQ made by Ultrasonix Medical ULC with 40 MHz sampling rate, 12-bit dynamic range, and programmable amplification up to 51 dB) in communication with four 128-channel pre-amplifiers to provide simultaneous one-to-one mapped associations with a 512-element transducer array. This PACT system can acquire photoacoustic signals from a cross section within 100 μs without multiplexing after each laser pulse excitation. The plurality of pre-amplifier channels may be directly coupled to the corresponding plurality of ultrasound transducers or may be coupled with electrical connecting cables. In one aspect, wireless communication may be employed.

Each of the one or more pre-amplifiers of a PACT system with spatiotemporal antialiasing may be set to a pre-amplifier gain that may be determined by one or more factors. For example, the pre-amplifier gain may be determined based on one or more of a minimum signal-to-noise ratio and one or more operating parameters of the data acquisition and processing system components such as analog-to-digital sampling devices (digitizers) of the DAQs, signal amplifiers, buffers, and the computing device. In one aspect, the pre-amplifier gain is in a range that is high enough to enable transmission of the photoacoustic signals with minimal signal contamination, but below a gain that may saturate the dynamic ranges of the DAQ system used to digitize the photoacoustic signals amplified by the pre-amplifier(s). In certain aspects, the gain of the plurality of pre-amplifier channels may be at least about 5 dB, at least about 7 dB, at least about 9 dB, at least about 11 dB, at least about 13 dB, at least about 15 dB, at least about 17 dB, at least about 19 dB, at least about 21 dB, at least about 23 dB, at least about 25 dB, or at least about 30 dB.

According to one aspect, a PACT system with spatiotemporal antialiasing includes a plurality of multi-channel pre-amplifiers (e.g., 128-channel preamplifiers) in electrical communication with an N-element ultrasonic transducer array and a plurality of multi-channel data acquisition systems (DAQs) in electrical communication with the plurality of pre-amplifiers respectively. Each of the DAQs is in communication with one of the preamplifiers. The plurality of multi-channel preamplifiers and the plurality of DAQs may also be in one-to-one mapping association with the N element ultrasonic transducer array. For example, a set of four 128-channel preamplifiers may be in electrical communication with a 512-element ultrasonic transducer array and a set of four 128-channel data acquisition systems (DAQs) may be in electrical communication with four 128-channel pre-amplifier(s) respectively. The four sets of 128-channel DAQs provide simultaneous one-to-one mapped associations with the 512-element ultrasonic transducer array to enable acquiring photoacoustic signals from a cross section without multiplexing after each laser pulse excitation.

Returning to FIG. 5, the PACT system with spatiotemporal antialiasing 500 also includes a computing device 580 having one or more processors or other circuitry 582, an optional (denoted by dashed line) display 586 in electrical communication with the processor(s) 582, and a computer readable media (CRM) 584 in electronic communication with the processor(s) or other circuitry 582. The computer readable media (CRM) 584 may be, e.g., a non-transitory computer readable media. Optionally (denoted by dashed line), the computing device 580 is in electronic communication with the light source(s) 510 to send control signals to trigger the illumination (e.g., triggering laser pulses). The computing device 580 is in electrical communication with the one or more DAQs 560 to receive data transmissions and/or to send control signal(s). Optionally (denoted by dashed line), the computing device 580 is in electronic communication with the one or more pre-amplifiers 550 to send control signal(s), e.g., to adjust amplification. The computing device 580 is in electrical communication with the antialiasing filter 581 to send control signals to adjust the cutoff frequency. The electrical communication between system components of the PACT system 500 may be in wired and/or wireless form. One or more of the electrical communications between components of the PACT system 500 may be able to provide power in addition to communicate signals. The computing device 580 may be, for example, a personal computer, an embedded computer, a single board computer (e.g. Raspberry Pi or similar), a portable computation device (e.g. tablet), a controller, or any other computation device or system of devices capable of performing the functions described herein. The computing device 580 is in electronic communication with the mechanism 570 to send control signals to control the movement and/or hold positions of the ultrasonic transducer array 540. The processor(s) 582 are in electrical communication with the CRM 584 to store and/or retrieve data such as the photoacoustic signal data. The one or more processor(s) and/or other circuitry 582 are in electrical communication with the optional display 586 to display data. Although not shown, the computing device 580 may also include a user input component for receiving data from a user.

The one or more processors and/or other circuitry 582 execute instructions stored on the CRM 584 to perform one or more operations of PACT methods. In certain implementations, the processor(s) 582 and/or other circuitry 582 execute instructions to perform one or more of: 1) determining an upper cutoff frequency for the antialiasing filter to trigger the antialiasing filter to comment temporal filtering; 2) communicating control signals to one or more components of the PACT system with spatiotemporal antialiasing 500, and 3) performing one or more reconstruction operations to reconstruct a two-dimensional or three-dimensional photoacoustic image of the specimen 530 using photoacoustic data. For example, the processor(s) and/or other circuitry 582 and/or one or more external processors may execute instructions that communicate control signals to the mechanism 570 to scan the ultrasonic transducer array 540 along a z-axis between to two elevations (3D mode) or move the ultrasonic transducer array 540 to one or more different elevations (2D mode) and send control signals to the digitizer in the DAQ(s) 560 to simultaneously record photoacoustic signals received by ultrasonic transducer array 540 from the illuminated regions of the specimen.

In some implementations, the PACT system includes one or more communication interfaces (e.g., a universal serial bus (USB) interface). Communication interfaces can be used, for example, to connect various peripherals and input/output (I/O) devices such as a wired keyboard or mouse or to connect a dongle for use in wirelessly connecting various wireless-enabled peripherals. Such additional interfaces also can include serial interfaces such as, for example, an interface to connect to a ribbon cable. It should also be appreciated that the various system components can be electrically coupled to communicate with various components over one or more of a variety of suitable interfaces and cables such as, for example, USB interfaces and cables, ribbon cables, Ethernet cables, among other suitable interfaces and cables.

Figure 6:
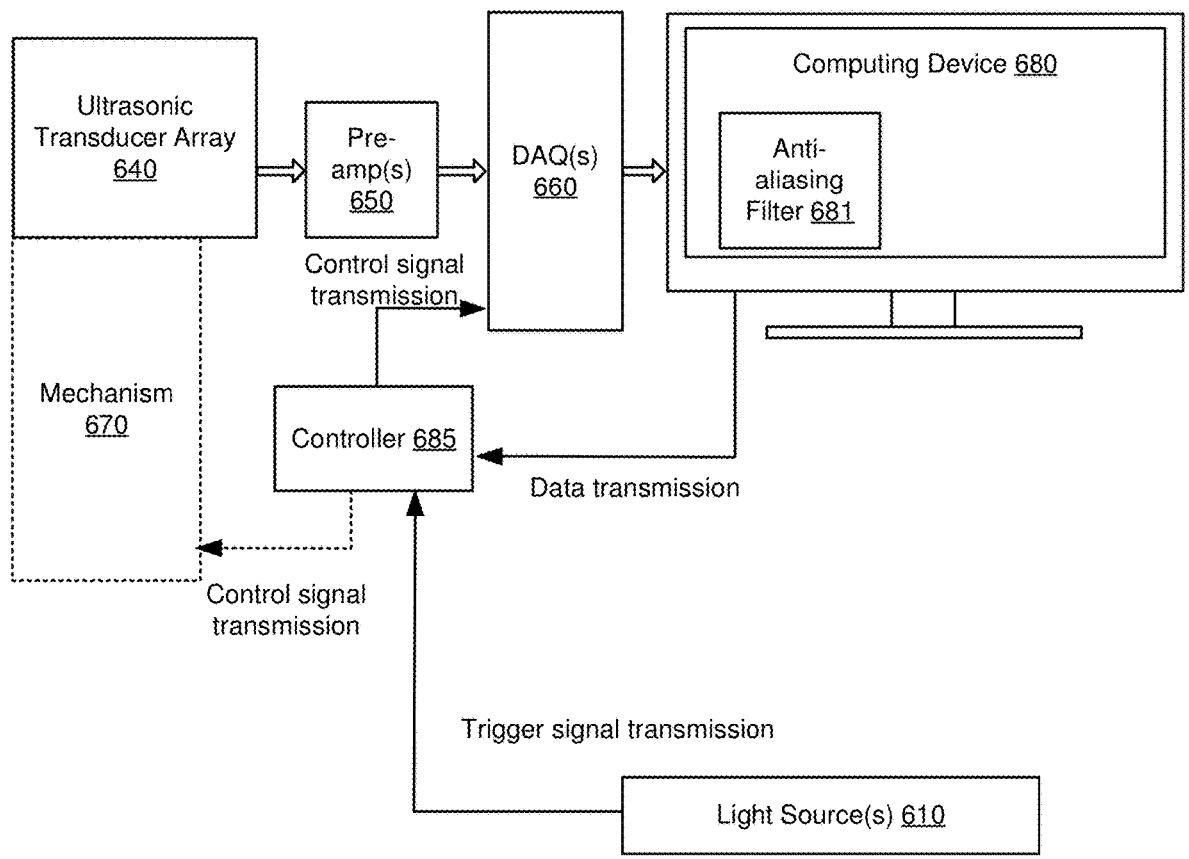
FIG. 6 is signal flow diagram of signals communicated between components of a PACT system with spatiotemporal antialiasing, according to implementations.

FIG. 6 is signal flow diagram of signals communicated between components of a PACT system with spatiotemporal antialiasing 600, according to implementations. The PACT system 600 includes one or more light sources 610 (e.g., a pulsed laser) and an optical system (not shown) that is configured to propagate/alter illumination from the one or more light sources 610 to a specimen being imaged. The PACT system 600 also includes an ultrasonic transducer array 640 that is coupled to or otherwise in acoustic communication with a specimen to receive photoacoustic signals induced by the illumination. The PACT system 600 also includes a optional (denoted by dotted line) mechanism 670 (e.g., a linear scanner) coupled to or otherwise operably connected to the ultrasonic transducer array 640 that can move the ultrasonic transducer array 640 to one or more elevational positions and/or scan the ultrasonic transducer array 640 between two elevational positions. The PACT system 600 also includes one or more pre-amplifiers 650 and one or more data acquisition systems (DAQs) 660 in one-to-one mapped association with the transducers in the ultrasonic transducer array 640. The one or more pre-amplifiers 650 are in electrical communication with the ultrasonic transducer array 640 to receive one or more photoacoustic signals and the DAQ(s) 660 are in electrical communication with the pre-amplifier(s) 650 to receive one or more boosted photoacoustic signals.

The PACT system with spatiotemporal antialiasing 600 also includes a computing device 680 having one or more processors or other circuitry and a computer readable media (CRM) in electronic communication with the processor(s). The PACT system 600 includes an anti-aliasing filter that may reside on the computer readable media. The antialiasing filter 681 is in electrical communication with the DAQ(s) 650 to receive photoacoustic data. The computing device 680 includes instructions residing on the computer readable media that can be executed to perform functions of the system 600 such as image reconstruction, spatial interpolation and determining an upper cutoff frequency of the anti-aliasing filter 681 and determining when to trigger temporal filtering.

The PACT system 600 also includes a controller 685 in electronic communication with the DAQ(s) 660 and the mechanism 670 to send control signals. The controller 685 may include one or more processors. To synchronize components of the PACT system 600, the one or more light sources 610 are configured to transmit a trigger signal to the controller 684 that triggers transmission of control signals to the DAQ(s) 660 to record signals and the mechanism 670 to move the ultrasonic transducer array 640. The computing device 680 is in communication with the controller 685 to be able to transmit control signals. The electrical communication between system components of the PACT system 600 may be in wired and/or wireless form. The electrical communications may be able to provide power in addition to communicate signals in some cases. During operation, digitized radio frequency data from the antialiasing filter 681 may be first stored in an onboard buffer, and then transferred to the computing device 680, e.g., through a universal serial bus 2.0. The DAQ(s) 660 may be configured to record photoacoustic signals within a time period, e.g., 100 μs, after each laser pulse excitation.

B. Examples of PACT Methods with Spatiotemporal Antialiasing

The PACT methods described in this section can be used to obtain one or more two-dimensional images and/or one or more three-dimensional volumetric images. The operations of these PACT methods can be performed by one or more components of a the PACT system with spatiotemporal antialiasing such as, e.g., the PACT system with spatiotemporal antialiasing 500 shown in FIG. 5 or the PACT system with spatiotemporal antialiasing 600 shown in FIG. 6. One or more of the operations may be performed executing instructions retrieved from computer readable media.

Figure 7:
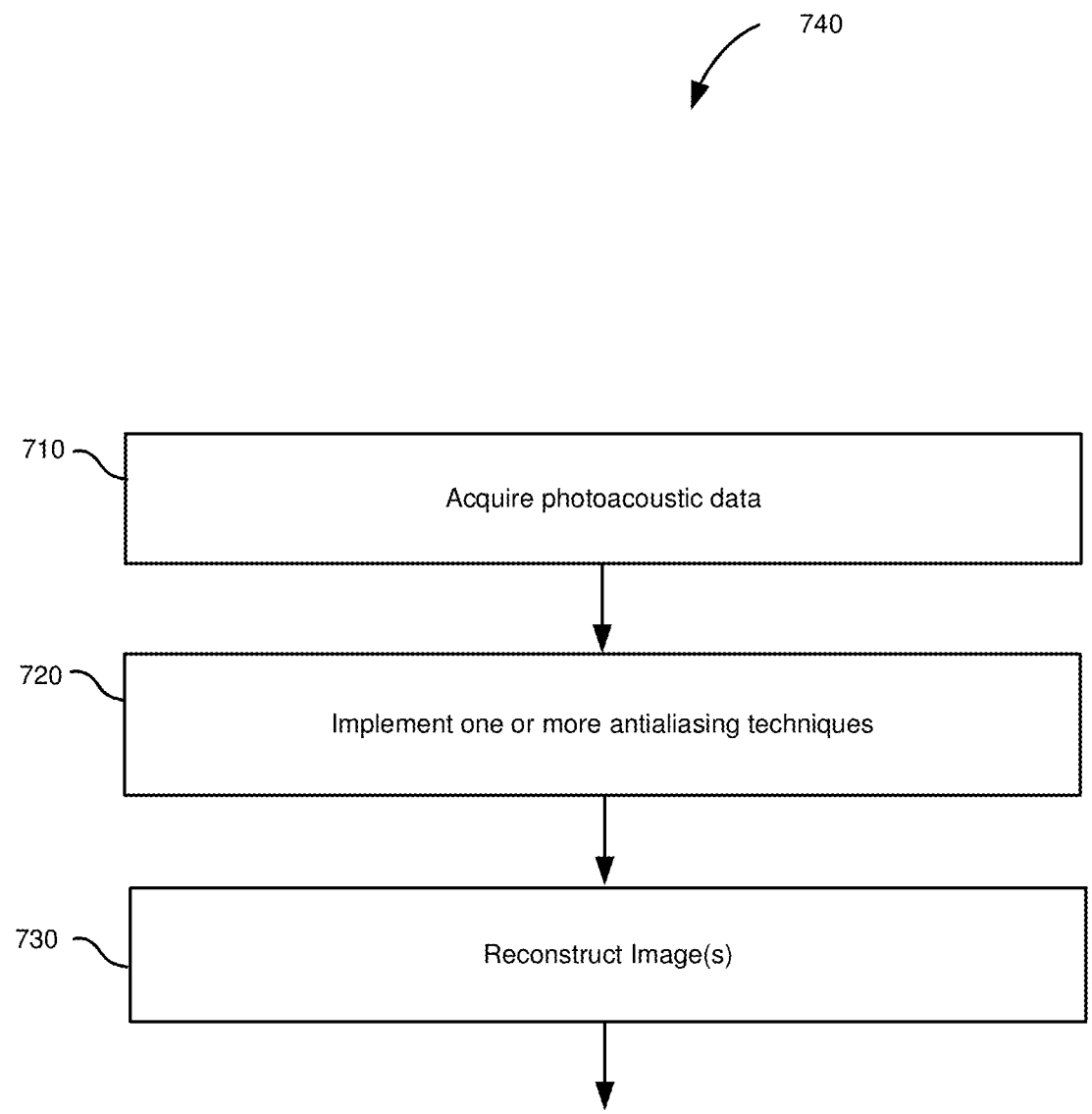
FIG. 7 is a flowchart depicting operations of a PACT method with spatiotemporal antialiasing that implements one or more antialiasing techniques, according to an implementation.

FIG. 7 is a flowchart depicting operations of a PACT method with spatiotemporal antialiasing that applies one or more antialiasing techniques (e.g., spatial interpolation and location-based temporal filtering), according to various implementations. Some examples of antialiasing techniques include one or both of spatial interpolation and location-based temporal filtering. For example, one implementation is directed to a method that applies spatial interpolation, but not location-based temporal filtering, and implements universal back-propagation for image reconstruction. As another example, one implementation is directed to a method that applies both spatial interpolation and location-based temporal filtering, and then applies universal back-propagation during image reconstruction. Spatial interpolation may be applied after location-based on temporal filtering in this example.

At operation 710, photoacoustic data is acquired. For example, one or more control signals may be sent to component(s) of the PACT system to perform data acquisition operations or recorded photoacoustic data may be retrieved from a computer readable media such as an onboard buffer.

In one aspect, the PACT system may control operations of system components to perform data acquisition. During the data acquisition phase, the recording of photoacoustic data by the one or more data acquisition systems (DAQs) may be synchronized with light pulses from the one or more light sources. To synchronize data acquisition with light pulses from the light source(s), the external trigger from the light source(s) may be used to trigger recording by the data acquisition systems and/or trigger movement of any mechanism that may be moving the transducer array according to one aspect. For example, during data acquisition in an exemplary two-dimensional (2D) mode, the ultrasonic transducer array may be moved to one or more elevational positions (e.g., different locations $z_1, z_2, \ldots$ along a z-axis of a linear stage) and held in each elevational position for a period of time during which the one or more DAQs record data. Some examples of time periods that may be used include: about 10 seconds, about 15 seconds, and about 20 seconds. In another example, the time period is in a range of about 10 seconds to about 20 seconds. At each cross section, photoacoustic data is continuously recorded at a certain sampling rate to monitor the cross section. As another example, during data acquisition in an exemplary three-dimensional (3D) mode, the ultrasonic transducer array is scanned through multiple scanning steps (elevational positions) through a depth.

During an exemplary data acquisition phase, digitized radio frequency data from the DAQs may be stored in an onboard buffer, and then transmitted to the computing device through e.g., a universal serial bus 2.0 or a universal serial bus 3.0. The photoacoustic data is recorded by the one or more data acquisition systems at a sampling frequency. In one aspect, the sampling frequency is 40 MHz. In another aspect, the sampling frequency may be in a range from 4 MHz to 100 MHz. The one or more data acquisition systems may be set to record photoacoustic data within a particular time period (e.g., 100 µs, 200 µs, or 300 µs) after each illumination e.g., laser pulse excitation. In certain implementations, a PACT system with spatiotemporal antialiasing is equipped with a one-to-one mapped signal amplification and data acquisition (DAQ) systems or DAQ circuits to the transducer elements. If there is one-to-one mapping associations, the one or more data acquisition systems can acquire photoacoustic signals from a cross-section of a specimen without multiplexing after illumination e.g., after each laser pulse excitation.

Returning to FIG. 7, at operation 720, one or more antialiasing techniques are implemented. For example, one or both of (i) location-based temporal filtering, and (ii) spatial interpolation may be implemented. If both spatial interpolation and location-based temporal filtering are implemented, location-dependent temporal filtering is applied before spatial interpolation according to one aspect. In some implementations, one or both of (i) location-based temporal filtering, and (ii) spatial interpolation may be used with UBP reconstruction.

An example of a spatial interpolation technique that may be used is the frequency domain implementation of Whittaker-Shannon interpolation. Given a time t, signals from all the detection elements formed a vector with length N. A fast Fourier transformation (FFT) is applied to the vector and zeros were padded behind the highest frequency components to double the vector length to 2N in a new vector. The inverse FFT is then applied to the new vector to spatially interpolate the data. Varying time t, one can generate a new set of signals from the detected signals. In this example, spatial interpolation numerically doubled the number of detection elements.

In certain implementations, the PACT methods implements location-based temporal filtering by applying an antialiasing filter with one or more low pass filters to remove components with frequencies higher than an upper cutoff frequency $f_c'$. The antialiasing filter may include a single lowpass filter or a combination of the same type or different types of lowpass filters. Some examples of lowpass filters that be implemented include a Butterworth filter, a Cheyshev filter, and a Bessel filter. In one example, the antialiasing filter includes at least in part a third-order lowpass Butterworth filter and a sinc filter (with the same cutoff frequency). The PACT method determines an upper cutoff frequency based on the distance between the reconstruction location and the transducer array being used in the PACT system. If the transducer array has a circular geometry, the upper cutoff frequency may be calculated as $$f_c' = \frac{Nc}{4\pi r'}$$

where N is the number of elements in the transducer array, c is the speed of sound, is the distance between the reconstruction location and the center of the transducer array. If the transducer array has a linear geometry, the upper cutoff frequency may be calculated using $$f_c' = \frac{c}{2d}\sqrt{1+\left(\frac{z}{\max\left\{\left|y-\frac{N-2}{2}d\right|,\left|y+\frac{N-2}{2}d\right|\right\}}\right)^2},$$

where d is the pitch of the transducer array, c is the speed of sound, and $f_c'$ is the upper cutoff frequency. Temporal filtering may be applied to every pixel/voxel location. In one implementation, location-based temporal filtering is applied to one or more groups of pixels/voxels with similar cutoff frequencies. The signals for these groups of pixels/voxels are filtered with different levels of cutoff frequencies before image reconstruction. During reconstruction, location-dependent cutoff frequencies are calculated, and the filtered signals are retrieved directly.

At operation 730, the PACT system performs image reconstruction. Image reconstruction may include (i) reconstructing one or more two-dimensional images at different positions of the ultrasonic transducer array and/or (ii) reconstructing a volumetric three-dimensional image for a depth scanned by the ultrasonic transducer array. Image reconstruction includes, at least in part, implementing an inverse reconstruction algorithm. Some examples of inverse reconstruction algorithms that can be used include: (i) forward-model-based iterative methods, (ii) time-reversal methods, and (iii) universal back-projection (UBP) method. For example, a 3D back projection algorithm can be used to reconstruct a 3D volumetric image or a 2D back projection algorithm can be used to reconstruct a 2D image. An example of a universal back-projection process can be found in Xu, M. And Wang, L., "Universal back-projection algorithm for photoacoustic computed tomography," *Physical Review E* 71, 016706 (2005), which is hereby incorporated by reference in its entirety. Another example of a back-projection process can be found in Anastasio, M. A. et al., "Half-time image reconstruction in thermoacoustic tomography," *IEEE Trans., Med. Imaging* 24, pp 199-210 (2005), which is hereby incorporated by reference in its entirety. In another aspect, a dual-speed-of sound (dual-SOS) photoacoustic reconstruction process may be used. Additional examples of inverse reconstruction algorithms are provided in Section I. An example of a single-impulse panoramic photoacoustic computed tomography system that employs a dual-SOS photoacoustic reconstruction process is described in U.S patent application 2019/0307334, titled "SINGLE- IMPULSE PANORAMIC PHOTOACOUSTIC COMPUTED TOMOGRAPHY" and filed on May 29, 2019, which is hereby incorporated by reference in its entirety.

Figure 9A:
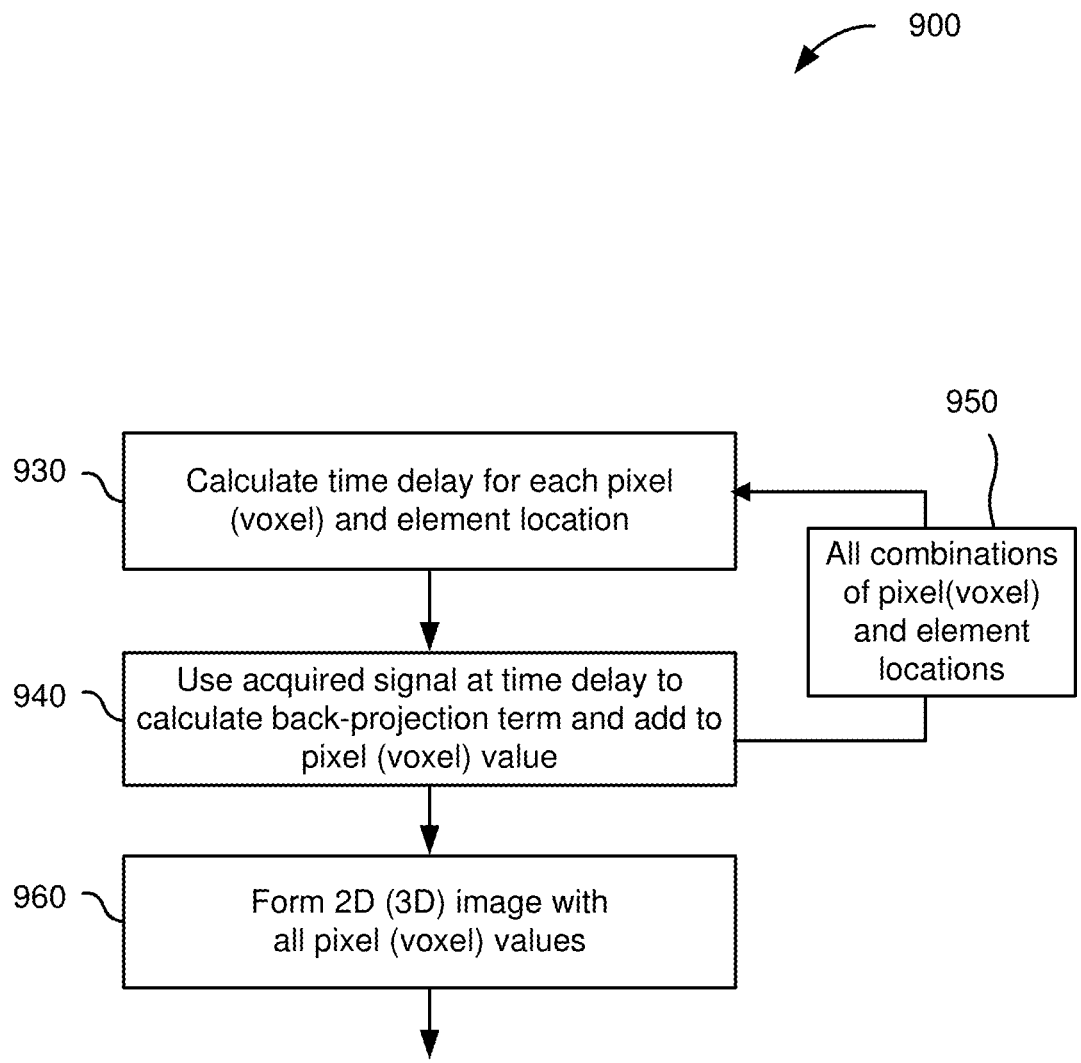
FIG. 9A is a flowchart of operations of a universal back-projection process that can be used to reconstruct either a 2D image or a 3D image, according to an implementation.
Figure 9B:
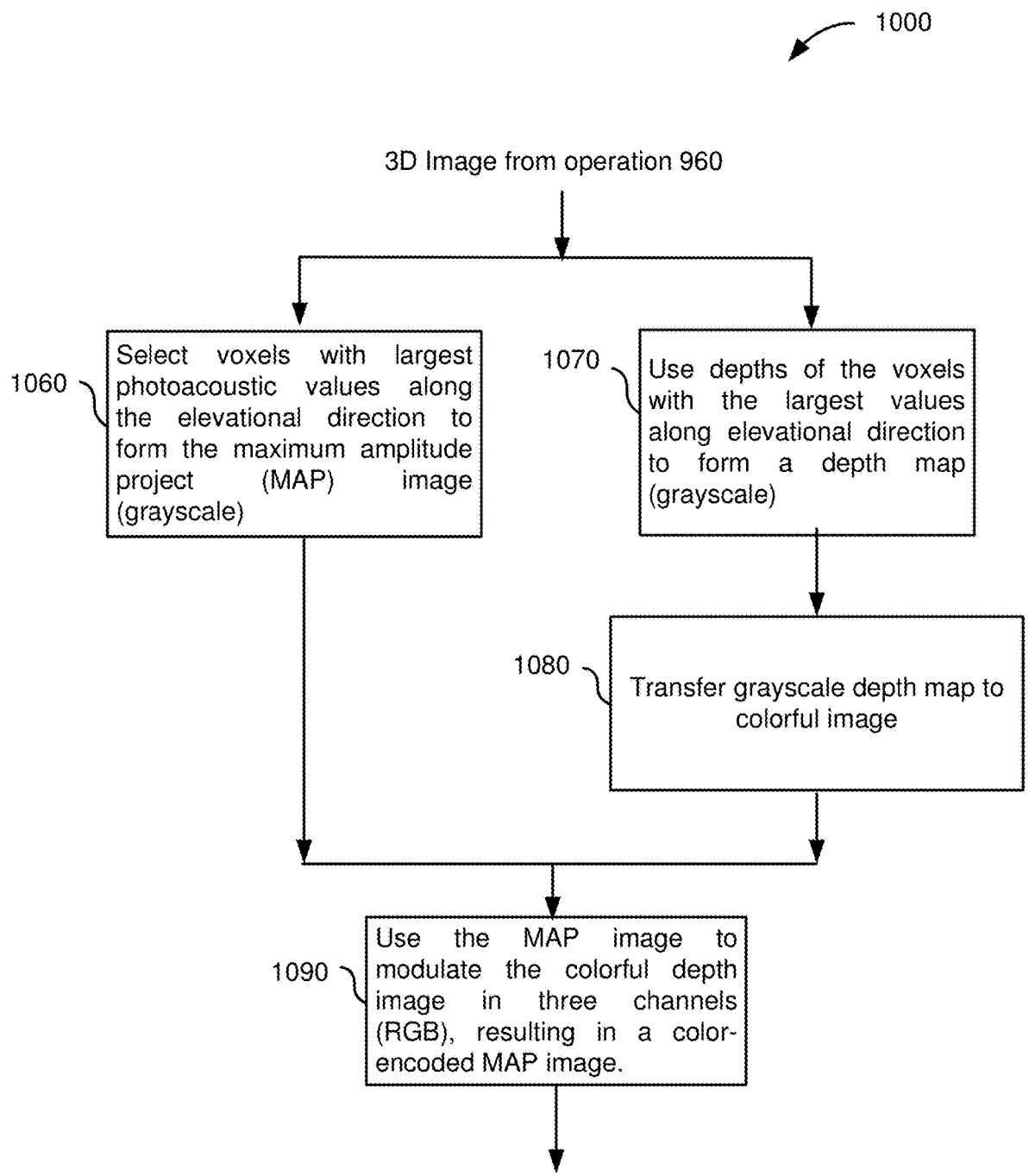
FIG. 9B is a flowchart of additional operations of the universal back-projection process in FIG. 9A as used for the 3D image, according to an implementation.

An example of a UBP method that can be implemented in the image reconstruction operation 730 is described with respect to the flowchart shown in FIGS. 9A and 9B. FIG. 9A is a flowchart of operations of a universal back-projection process that can be used to reconstruct either a 2D image or a 3D image, according to an implementation. FIG. 9B is a flowchart of additional operations of the universal back-projection process in FIG. 9A as used for the 3D image, according to an implementation. More details for an example of this process can be found in Anastasio, M. A. et al., "Half-time image reconstruction in thermoacoustic tomography," *IEEE Trans. Med. Imaging* 24, 199-210 (2005), which is hereby incorporated by reference in its entirety.

At operation 930, the time delay is calculated for a pixel (voxel) and transducer element location. At operation 940, an acquired photoacoustic signal at the time delay is used to calculate a back-projection term and this is added to the pixel (voxel) value. At operation 950, the method returns to repeat operations 930 and 940 for all combinations of pixel (voxel) and transducer element locations. At operation 960, a 2D (3D) image is formed of all the pixel (voxel) values.

In FIG. 9B, a three-dimensional image output from operation 960 in FIG. 9A is received. At operation 1060, in the elevational direction of each filtered volumetric 3D image, voxels are selected with the largest photoacoustic amplitudes to form a maximum amplitude projection (MAP) 2D image in grayscale. At operation 1070, the depths of the voxels along with their largest photoacoustic amplitude values from operation 1060 are used to form a depth map in grayscale. At operation 1080, the grayscale depth map is transferred to a colorful depth image. At operation 1090, the MAP image is used to modulate the colorful depth image in three channels (RGB), resulting in a color-encoded MAP image. A median filtration with a window size of 3×3 pixels to the depth image. Another median filtration with a window size of 6×6 pixels may be further applied. Different RGB (red, green, blue) color values were assigned to discrete depths. The 2D depth-resolved color-encoded image is multiplied by the MAP image pixel by pixel to represent the maximum amplitudes. In one aspect, to further reduce noise and improve image quality, the parameters are tuned in 2D slices at different depths.

Figure 8:
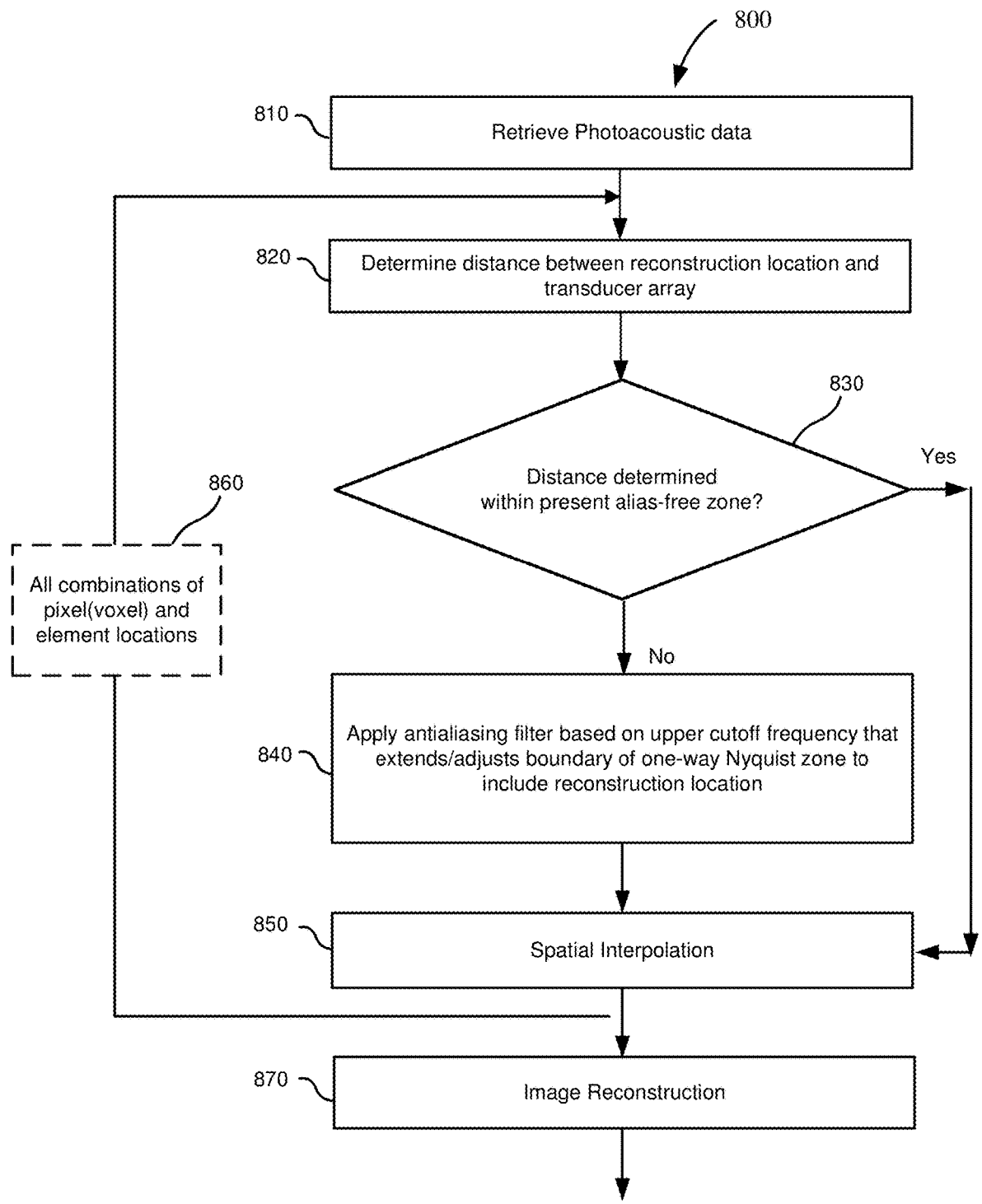
FIG. 8 is a flowchart depicting operations of a PACT method with spatiotemporal antialiasing that applies location-based temporal filtering, according to an implementation.

FIG. 8 is a flowchart depicting operations of a PACT method with spatiotemporal antialiasing that applies temporal filtering with a location-dependent antialiasing filter to the temporal signals before applying spatial interpolation. The location-dependent temporal filtering includes at least operations 820, 830, and 840.

At operation 810, one or more control signals are sent to component(s) of the PACT system to perform data acquisition or the photoacoustic data is received or retrieved from a component of the PACT system. For example, photoacoustic data may be retrieved or received from a computer readable media such as, e.g., an onboard buffer.

At operation 820, a distance between the reconstruction location of the pixel (voxel) and the transducer array is determined. At operation 830, it is determined whether the distance determined is places the reconstruction location within the present alias-free zone. In one implementation, the alias-free zone $S_2$ for a transducer array with a circular geometry may be determined from Eqn. 22. In one implementation, the alias-free zone $S_2$ for a transducer array with linear geometry may be determined from Eqn. 34. If it is determined that the distance determined places the reconstruction location within the present alias-free zone, the method continues to operation 850 to perform spatial interpolation. If it determined that the distance determined places the reconstruction location outside the present alias-free zone, the method continues to operation 840.

At operation 840, a location-dependent antialiasing filter is applied with an upper cutoff frequency that extends the one-way Nyquist zone (no aliasing in spatial sampling) $S_1$ to an adjusted one-way Nyquist zone $S_1'$ that includes the reconstruction location. The antialiasing filter includes one or more low pass filters that can remove components with frequencies higher than the upper cutoff frequency. The antialiasing filter may include a single lowpass filter or a combination of the same type or different types of lowpass filters. Some examples of lowpass filters that be implemented include a Butterworth filter, a Cheyshev filter, and a Bessel filter. In one example, the antialiasing filter includes at least in part a third-order lowpass Butterworth filter and a sinc filter (with the same cutoff frequency). The PACT method determines an upper cutoff frequency based on the distance between the reconstruction location and the transducer array. If the transducer array has a circular geometry, the upper cutoff frequency may be calculated as $$f_c' = \frac{Nc}{4\pi r'}$$

where N is the number of elements in the transducer array, c is the speed of sound, r' is the distance between the reconstruction location and the center of the transducer array. If the transducer array has a linear geometry, the upper cutoff frequency may be calculated using $$f_c' = \frac{c}{2d}\sqrt{1+\left(\frac{z}{\max\left\{\left|y-\frac{N-2}{2}d\right|,\left|y+\frac{N-2}{2}d\right|\right\}}\right)^2},$$

where d is the pitch of the transducer array, c is the speed of sound, and $f_c'$ is the upper cutoff frequency. Temporal filtering may be applied to every pixel/voxel location. In one implementation, location-based temporal filtering is applied to one or more groups of pixels/voxels with similar cutoff frequencies. The signals for these groups of pixels/voxels are filtered with different levels of cutoff frequencies before image reconstruction. During reconstruction, location-dependent cutoff frequencies are calculated, and the filtered signals are retrieved directly.

At operation 850, spatial interpolation is applied. The spatial interpolation operation may remove aliasing in image reconstruction to extend the present alias-free two-way Nyquist zone to an adjusted second two-way Nyquist zone that includes the reconstruction location. An example of a spatial interpolation technique that may be used is the frequency domain implementation of Whittaker-Shannon interpolation. Given a time t, signals from all the detection elements formed a vector with length N. A fast Fourier transformation (FFT) is applied to the vector and zeros were padded behind the highest frequency components to double the vector length to 2N in a new vector. The inverse FFT is then applied to the new vector to spatially interpolate the data. In this example, spatial interpolation numerically doubled the number of detection elements.

At optional (denoted by dashed line) operation 860, the method returns to repeat operations 830, 840, and 950 for all combinations of pixel (voxel) locations. In another implementation, location-based temporal filtering may be applied to one or more groups of pixels/voxels with similar cutoff frequencies. The signals for these groups of pixels/voxels are filtered with different levels of cutoff frequencies before image reconstruction. In this implementation, before reconstruction, photoacoustic signals are first filtered with different levels of cutoff frequencies associated with these groups. During reconstruction, location-dependent cutoff frequencies are calculated, and the filtered signals are retrieved directly, which may reduce time in data filtering.

At operation 870, image reconstruction operations are performed including at least on in part implementing an inverse reconstruction algorithm. Image reconstruction may include (i) reconstructing one or more two-dimensional images at different positions of the ultrasonic transducer array and/or (ii) reconstructing a volumetric three-dimensional image for a depth scanned by the ultrasonic transducer array. Some examples of inverse reconstruction algorithms that can be used include: (i) forward-model-based iterative methods, (ii) time-reversal methods, and (iii) universal back-projection (UBP) method. For example, a 3D back projection algorithm can be used to reconstruct a 3D volumetric image or a 2D back projection algorithm can be used to reconstruct a 2D image. An example of a universal back-projection process can be found in Xu, M. And Wang, L., "Universal back-projection algorithm for photoacoustic computed tomography," *Physical Review* E 71, 016706 (2005), which is hereby incorporated by reference in its entirety. Another example of a back-projection process can be found in Anastasio, M. A. et al., "Half-time image reconstruction in thermoacoustic tomography," *IEEE Trans., Med. Imaging* 24, pp 199-210 (2005), which is hereby incorporated by reference in its entirety. In another aspect, a dual-speed-of sound (dual-SOS) photoacoustic reconstruction process may be used. Additional examples of inverse reconstruction algorithms are provided in Section I. An example of a single-impulse panoramic photoacoustic computed tomography system that employs a dual-SOS photoacoustic reconstruction process is described in U.S patent application 2019/0307334, titled "SINGLE-IMPULSE PANORAMIC PHOTOACOUSTIC COMPUTED TOMOGRAPHY" and filed on May 29, 2019, which is hereby incorporated by reference in its entirety.

IV. Numerical Simulations

Numerical simulations of examples of three-dimensional and two-dimensional detection geometry were performed to evaluate the effects of spatial interpolation and/or location-dependent temporal filtering on mitigating spatial aliasing in image reconstruction.

A. Three-Dimensional Examples

To visualize artifacts caused by spatial aliasing without spatiotemporal antialiasing, a numerical simulation of a three-dimensional example of a hemispherical detection geometry was used. The k-wave toolbox discussed in Treeby B. E. and Cox, B. T., "k-Wave: MATLAB toolbox for the simulation and reconstruction of photoacoustic wave fields," *J. Biomed. Opt.*, vol. 15, no. 2, p. 021314 (2010) was used for the forward problem. The parameters used in the simulation were: the frequency range of the ultrasonic transducer is from 0.1 MHz to 4.5 MHz (2.3-MHz central frequency, 191% bandwidth, $f_c$=4.5 MHz), the speed of sound (SOS) c=1.5 mm·μ$^{-1}$, the number of detection elements N=651 (evenly distributed on the hemisphere based on the method in Deserno, M., "How to generate equidistributed points on the surface of a sphere," *Polym.* Ed, p. 99 (2004), which is hereby incorporated by reference in its entirety), the radius of the hemisphere R=30 mm, and the simulation grid size is 0.1×0.1×0.1 mm$^3$).

Figure 10A:
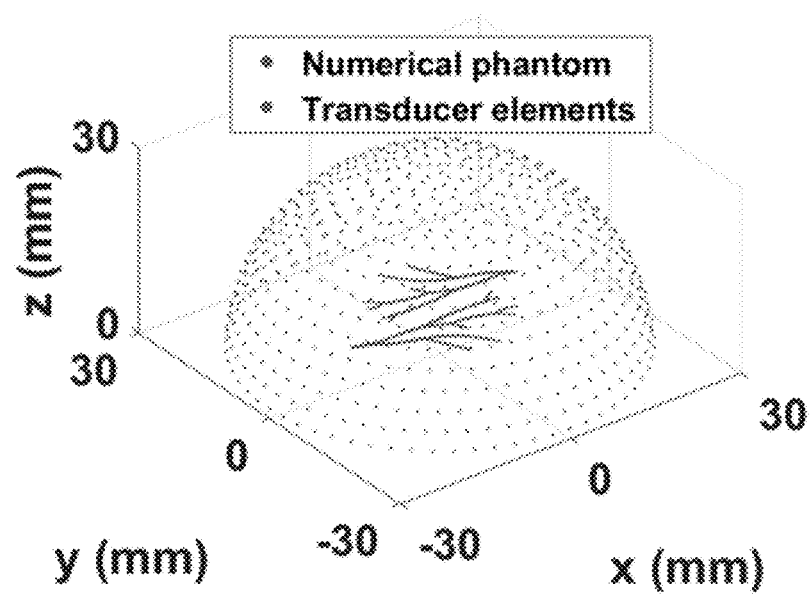
FIG. 10A is an illustration of a numerical simulation of a transducer array and a simple phantom, according to an implementation.
Figure 10B:
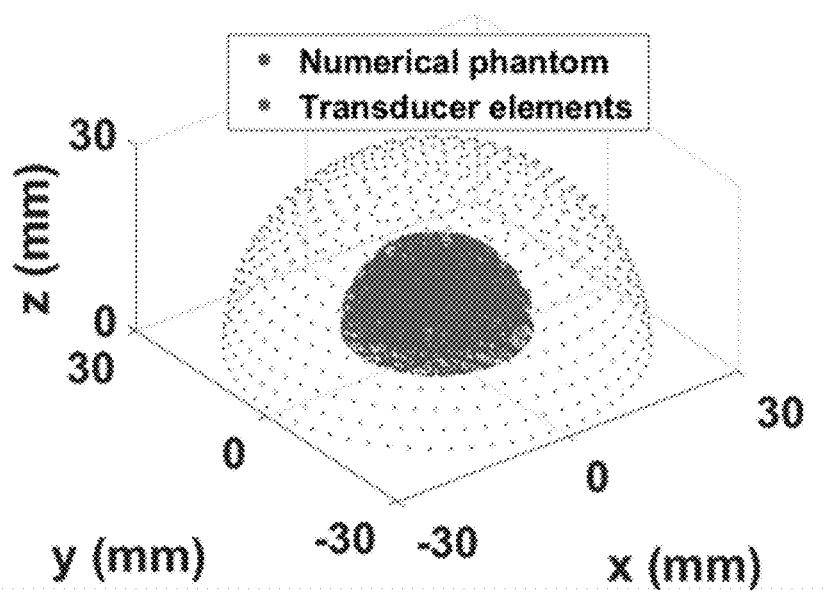
FIG. 10B is an illustration of a numerical simulation of the transducer array in FIG. 10A with a complex numerical phantom, according to an implementation.
Figure 11:
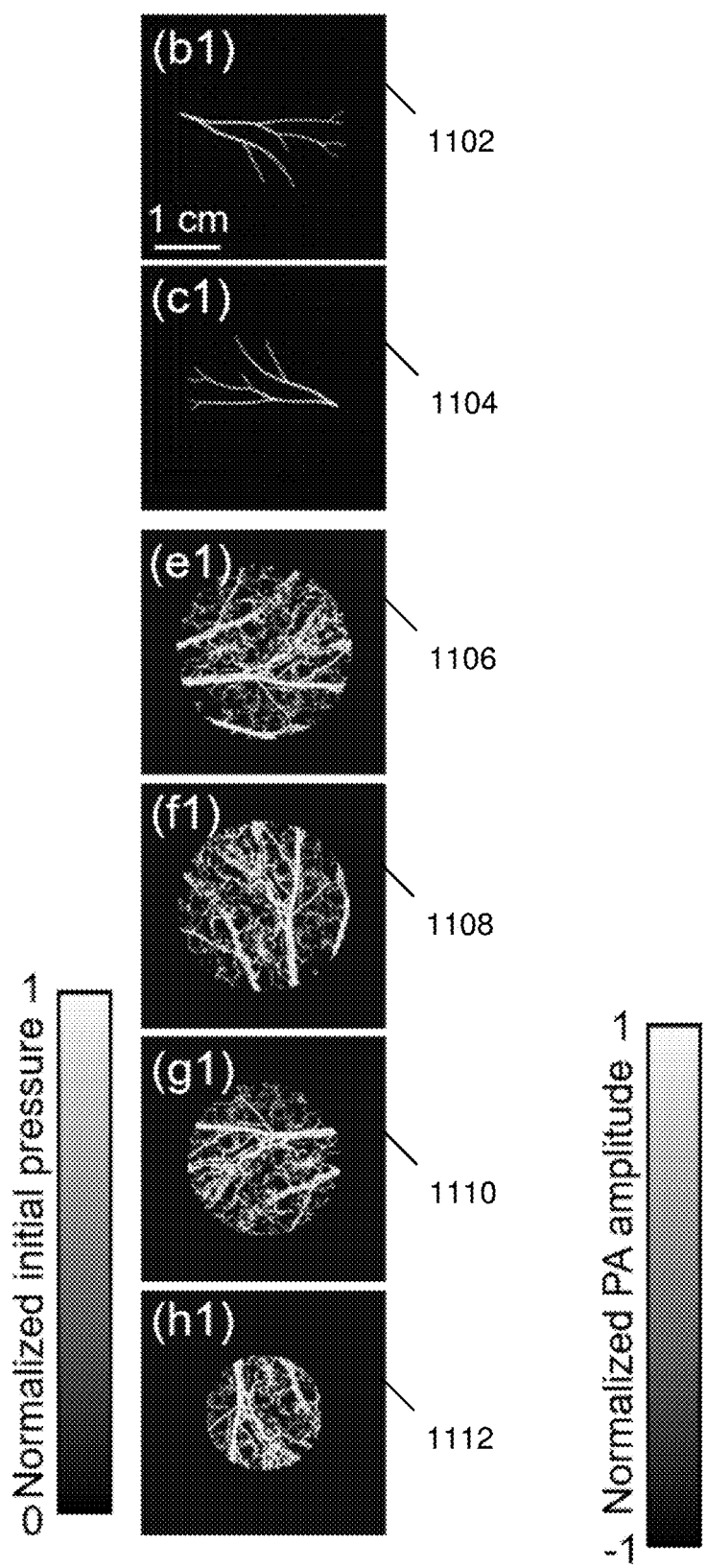
FIG. 11 depicts ground truth slices, according to an implementation.
Figure 12:
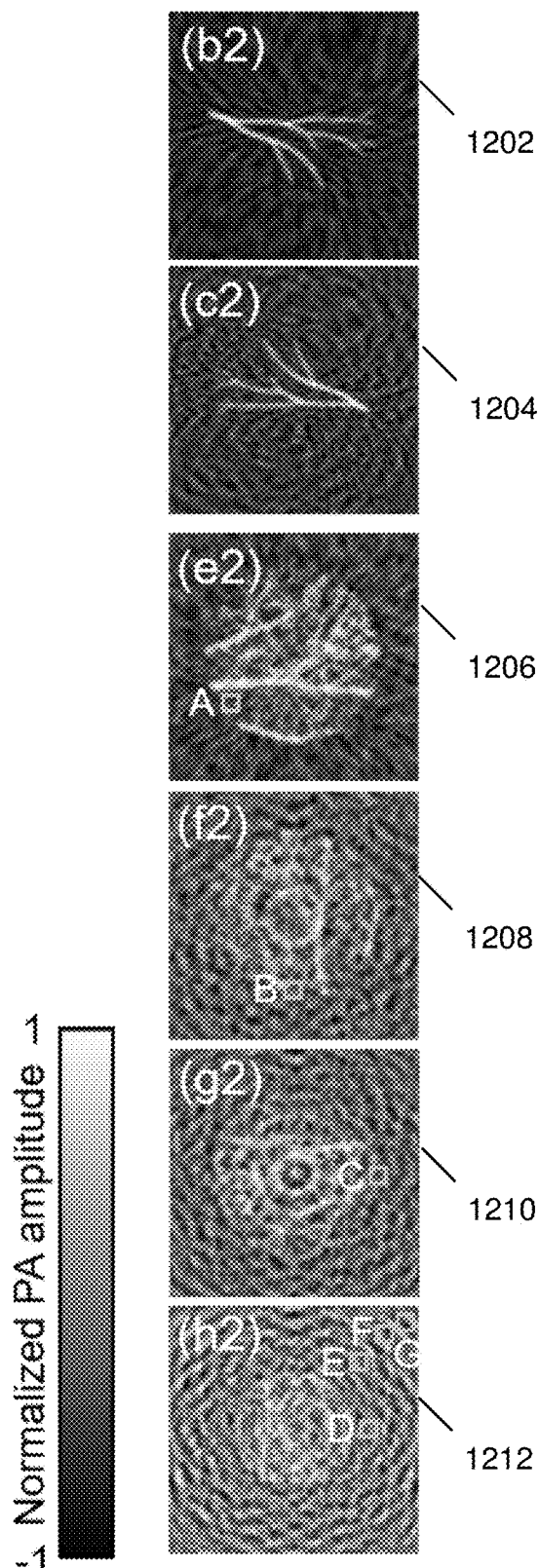
FIG. 12 depicts reconstructed images, according to an implementation.

FIG. 10A is an illustration of a numerical simulation of a transducer array with 651 detection elements evenly distributed on a hemisphere and a simple numerical phantom covered by the array, according to an implementation. FIG. 10B is an illustration of a numerical simulation of the transducer array in FIG. 10A with a complex numerical phantom, according to an implementation. FIG. 11 depicts ground truth slices 1102, 1104, 1106, 1108, 1110, and 1112, according to an implementation. FIG. 12 depicts reconstructed images 1202, 1204, 1206, 1208, 1210, and 1212, according to an implementation. Ground truth slice 1102 and reconstructed image 1202 are of a simple phantom at z=0. Ground truth slice 1104 and reconstructed image 1204 are of a simple phantom at z=6.8 mm. Ground truth slice 1106, 1108, 1110, and 1112 and reconstructed image 1206, 1208, 1210, and 1212 are of a complex phantom at z=0, 3.4, 6.8, and 10.2 mm respectively.

In FIG. 10A, the transducer elements are shown as a hemisphere of dots. A simple numerical phantom with nonzero initial pressure from two layers with distances of 0 and 6.8 mm from the xy plane was analyzed first. The phantom is shown as a line of dots in FIG. 10A. The ground-truth images of the two layers are 1102 and 1104, respectively, and the reconstructions are 1202 and 1204, respectively. As can be seen, artifacts appear in both layers and seem stronger in the layer further from the xy plane.

Using the same array, a complex phantom was simulated with nonzero initial pressure from four layers with distances of 0, 3.4, 6.8, and 10.2 mm from the xy plane, shown as a center portion of dots in FIG. 10B. The ground-truth images of the four layers are 1106, 1108, 1110, and 1112 in FIG. 11, respectively, and the reconstructions are 1206, 1208, 1210, and 1212 in FIG. 12 respectively. Strong aliasing artifacts appear in all reconstructed images, and the artifacts tend to be more visible in layers further from the origin. Regions of interest A-G (1.5×1.5 mm$^2$) with increasing distances from the origin were picked from the four layers at locations with zero initial pressure. The standard deviations of the pixel values inside these regions of interest were calculated to quantify the aliasing artifacts.

Figure 13:
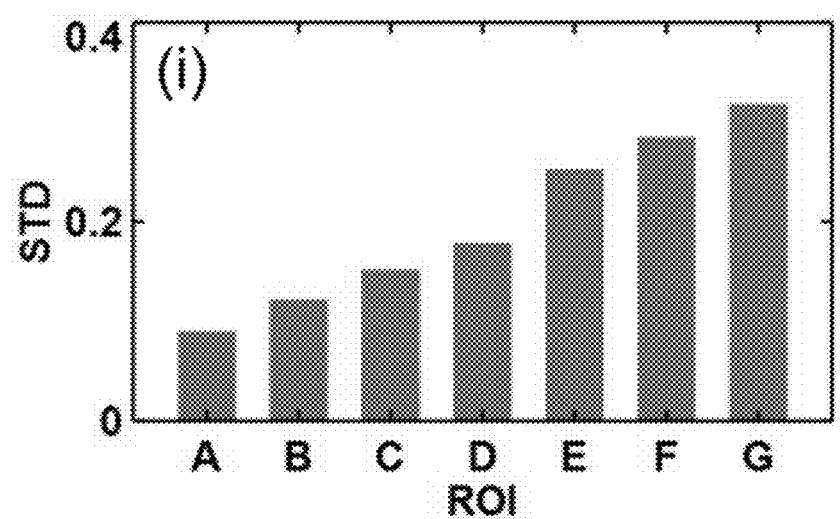
FIG. 13 is a graph of standard deviations of pixel values in regions of interest in reconstructed images in FIG. 11, according to an implementation.

FIG. 13 is a graph of standard deviations of pixel values in the regions of interest outlined in the boxes shown in reconstructed images 1206, 1208, 1210, and 1212 in FIG. 11, according to an implementation. As can be seen in FIG. 13, artifacts become stronger as the region of interest moves away from the origin.

The three-dimensional (3D) simulation provide a direct observation of spatial aliasing artifacts. In addition, the 3D simulation provides a simplified estimation of the one-way Nyquist zone of the hemisphere geometry. On each of the planes crossing the center of the hemisphere, the one-way Nyquist zone for the 2D case is calculated. All the detection elements for each plane lie on its intersection with the hemisphere, which is a semicircle with length πR (subset of a full circle with length 2πR). Based on the above analysis, one only need to estimate the number of detection elements for this plane. Given the area of the hemisphere 2πR$^2$ and the number of elements N, the distance between two neighboring elements is approximately $$\sqrt{\frac{2\pi R^2}{N}}.$$

Thus, the number of elements (in a full circle) for this plane is approximately:

$$N' = \frac{2\pi R}{\sqrt{\frac{2\pi R^2}{N}}} = \sqrt{2\pi N}. \quad \text{(Eqn 35)}$$

Using Eqn. 15, the one-way Nyquist zone on this plane is:

$$S'_1 = \left\{ r' \,\middle|\, \|r'\| \le \frac{N'\lambda_c}{4\pi} \right\} = \left\{ r' \,\middle|\, \|r'\| \le \frac{c}{4f_c}\sqrt{\frac{2N}{\pi}} \right\}. \quad \text{(Eqn. 36)}$$

For a 3D simulation, the plane's normal vector is varied: All the 2D regions $S_1'$ form a half ball with radius $$\frac{c}{4f_c}\sqrt{\frac{2N}{\pi}} \approx 1.70 \text{ mm},$$

which is much smaller than the radius R=30 mm. This large difference explains the prevalence of artifacts in the reconstructed 3D image.

B. Two-Dimensional Examples

In a two-dimensional example, a full-ring transducer array with a radius R=30 mm was used. The frequency range of the full-ring transducer array was from about 0.1 MHz to about 4.5 MHz. The number of detection elements was N=512 and the speed of sound is c=1.5 mm·µs$^{-1}$. The radius of the one-way Nyquist zone $S_1$ is thus $$r = \frac{Nc}{4\pi f_c} \approx 13.6 \text{ mm}.$$

In the numerical simulation, a 0.1×0.1 mm$^2$ grid size was used. A simple initial pressure distribution was simulated.

Simple Phantom Example

Figure 14:
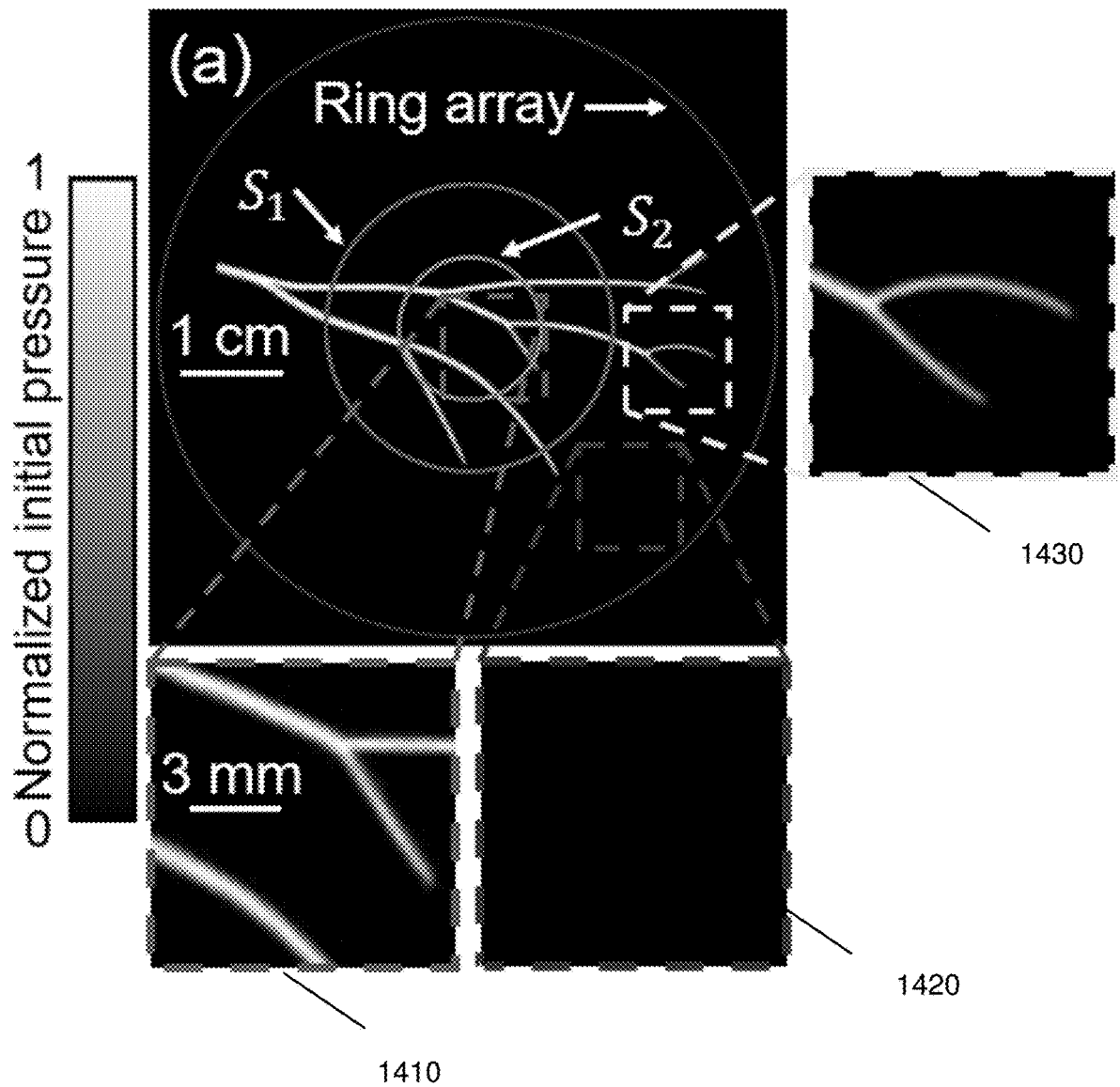
FIG. 14 is an illustration of ground truth of a simple initial pressure distribution for a simple phantom, according to an implementation.

FIG. 14 is an illustration of ground truth of a simple initial pressure $p_0$ distribution for a simple phantom, according to an implementation. A full-ring transducer array and the circular boundaries of $S_1$ and $S_2$ are depicted as circles, respectively. The illustration includes blown up illustrations of boxed regions 1410, 1420, and 1430 in the imaging domain of the full-ring transducer array. The boxed region 1410 lies mainly within zone $S_2$. The boxed region 1420 lies outside zone $S_1$ and does not include the simple phantom. The boxed region 1430 lies outside zone $S_1$ and includes a portion of the simple phantom.

Figure 15A:
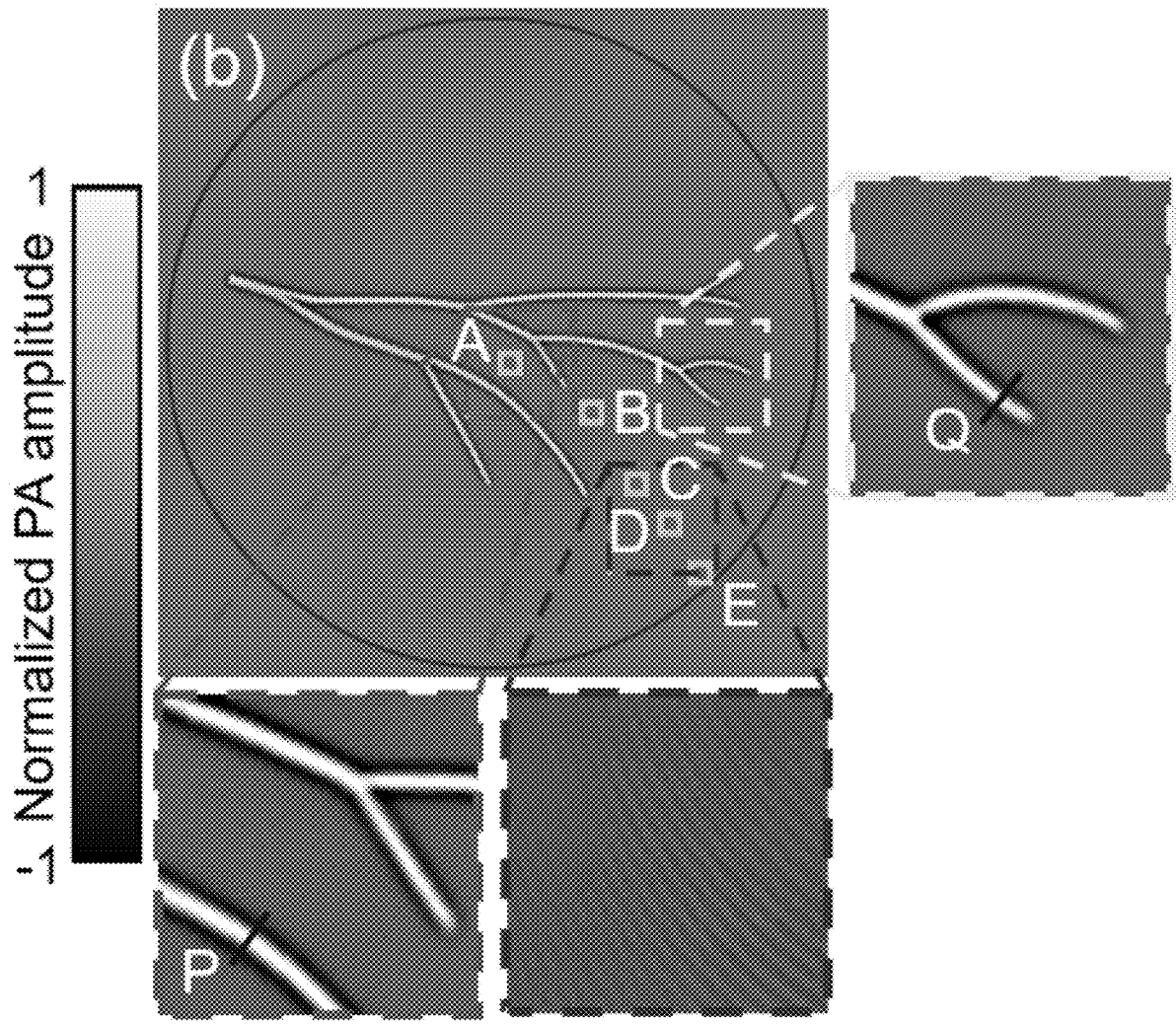
FIG. 15A is a reconstructed image of the simple phantom object in FIG. 14 using a first method including UBP reconstruction, according to an implementation.

The image of the simple phantom object was reconstructed using a universal back projection algorithm (sometimes referred to as "universal back projection reconstruction"). FIG. 15A is a reconstructed image of the simple phantom object shown in FIG. 14 using a first antialiasing method including universal back projection reconstruction, according to an implementation. Despite the clean ground-truth background in FIG. 14, spatial aliasing-induced artifacts appear in the reconstructed image outside zone $S_1$, but not inside the box 1410 mainly within zone $S_1$. The region 1430 is outside zone $S_1$, but does not show strong artifacts. Due to the specific distribution of the source, the artifacts turn out to be much stronger in the region 1420 than in region 1430.

Figure 15B:
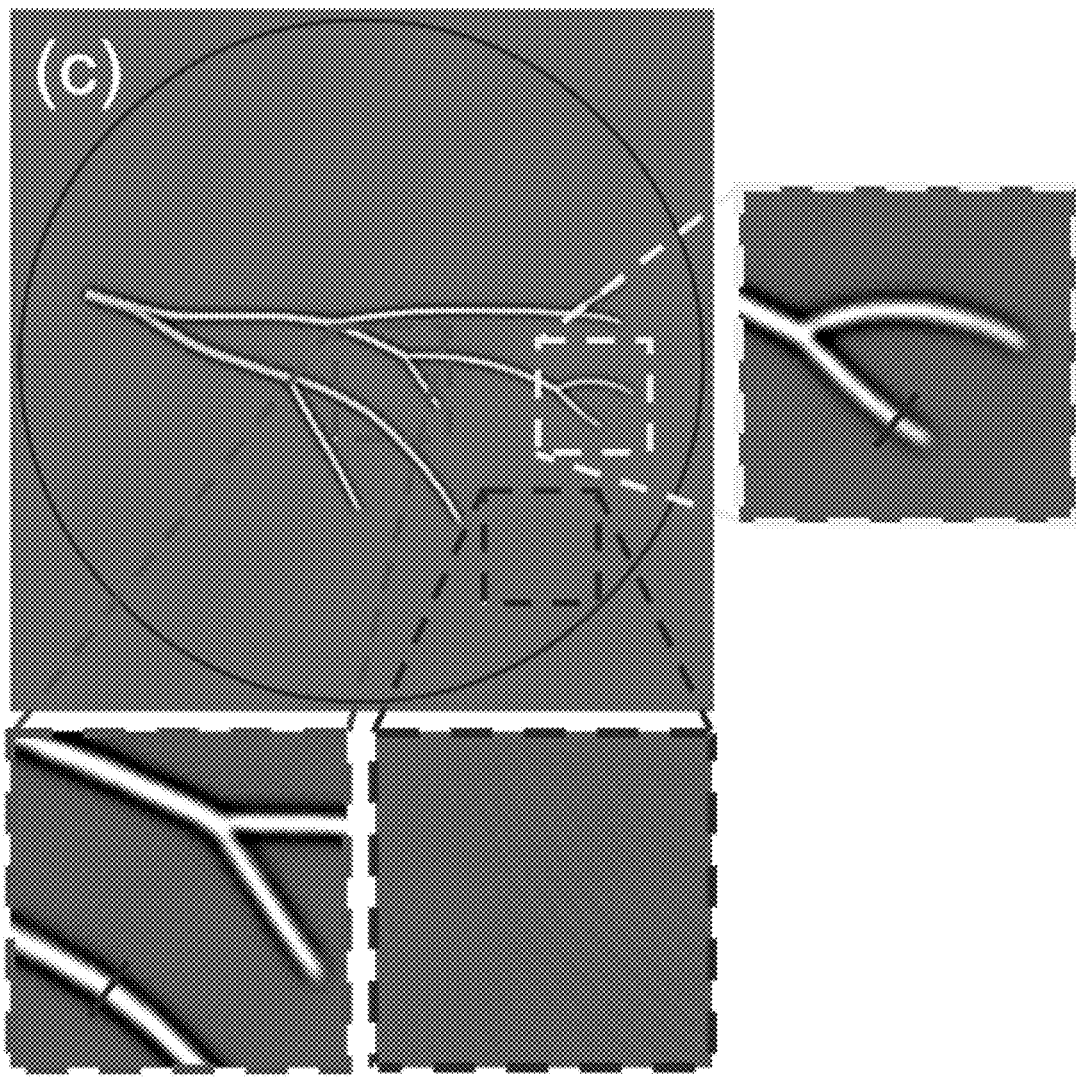
FIG. 15B is a reconstructed image of the simple phantom object in FIG. 14 using a second method including UBP reconstruction and spatial interpolation, according to an implementation.

In a second method, spatial interpolation is used to remove the aliasing in image reconstruction and the image is reconstructed using a universal back projection algorithm. Given a time t, signals from all the detection elements formed a vector with length N. The fast Fourier transformation (FFT) was then applied to the vector, and zeros were padded behind the highest frequency components to double the vector length to 2N. Finally, the inverse FFT was applied to the new vector to interpolate the data. This process is the frequency domain implementation of Whittaker-Shannon interpolation. Spatial interpolation numerically doubled the number of detection elements. FIG. 15B is a reconstructed image of the simple phantom object in FIG. 14 using the second method including UBP reconstruction and spatial interpolation, according to an implementation.

Figure 15C:
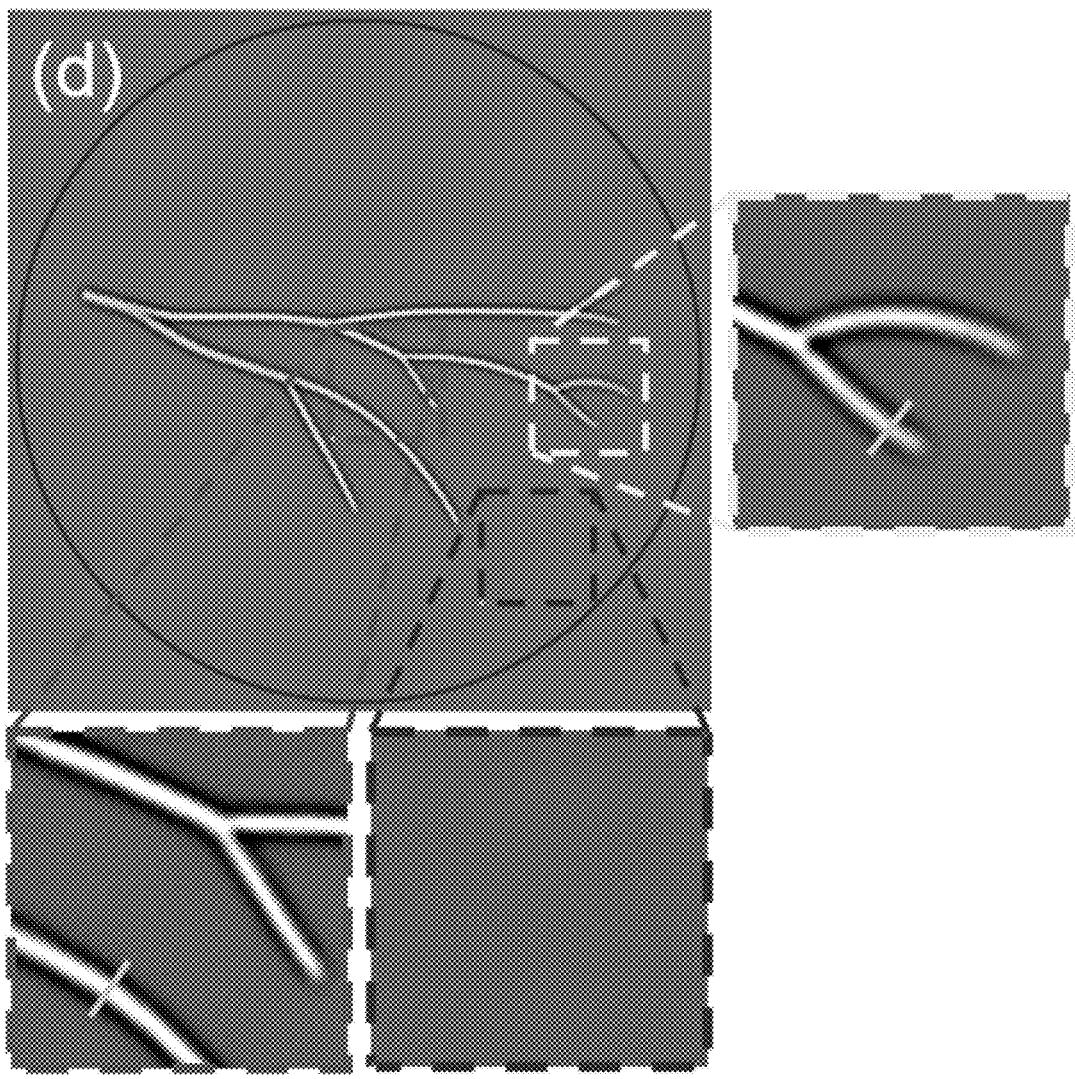
FIG. 15C is a reconstructed image of the simple phantom object in FIG. 14 using a third method including UBP reconstruction, spatial interpolation, and location-dependent temporal filtering, according to an implementation.

In a third method, to remove the spatial aliasing during spatial sampling, a location-dependent antialiasing filter with one or more lowpass filters was applied to the temporal signals before spatial interpolation. In the simulation, the antialiasing filter included a third-order lowpass Butterworth filter and a sinc filter (with the same cutoff frequency) was implemented for location-dependent temporal filtering. FIG. 15C is a reconstructed image of the simple phantom object in FIG. 14 using a third method including UBP reconstruction, spatial interpolation, and location-dependent temporal filtering, according to an implementation.

Figure 16:
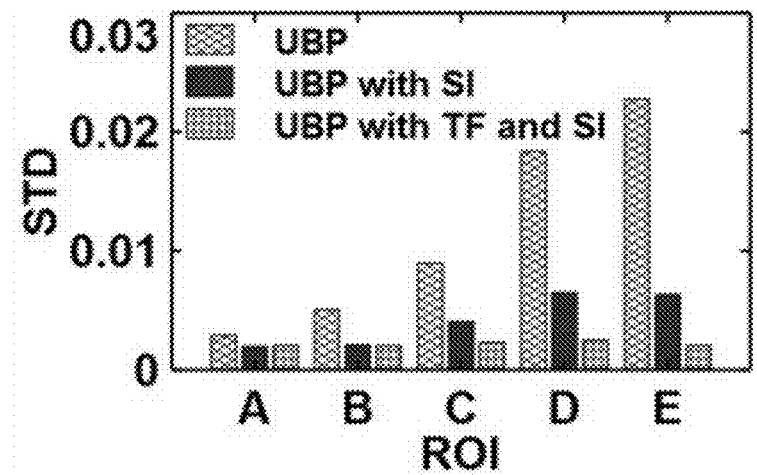
FIG. 16 is a graph with a plot of standard deviations of the regions of interest in FIG. 15A using (1) UBP reconstruction (2) UBP reconstruction and spatial interpolation, and (3) UBP reconstruction, spatial interpolation, and location-dependent temporal filtering (TF).

To quantify the amplitude of artifacts, regions of interest A-E marked with small boxes in FIG. 15, each region of interest having an area of 1.2×1.2 mm$^2$, were selected at locations with zero initial pressure. The standard deviations of the pixel values inside these regions was calculated. FIG. 16 is a graph with a plot of standard deviations of the regions of interest A-E using three methods: (1) a first method with UBP reconstruction alone, (2) a second method with UBP reconstruction and spatial interpolation, and (3) a third method with UBP reconstruction, spatial interpolation (SI), and location-dependent temporal filtering (TF). As shown in FIG. 16, spatial interpolation mitigates the aliasing artifacts significantly, while adding location-dependent temporal filtering before spatial interpolation further diminishes the artifacts. This agrees with the above discussion that both spatial interpolation and location-dependent temporal filtering extend the alias-free region.

Figure 17:
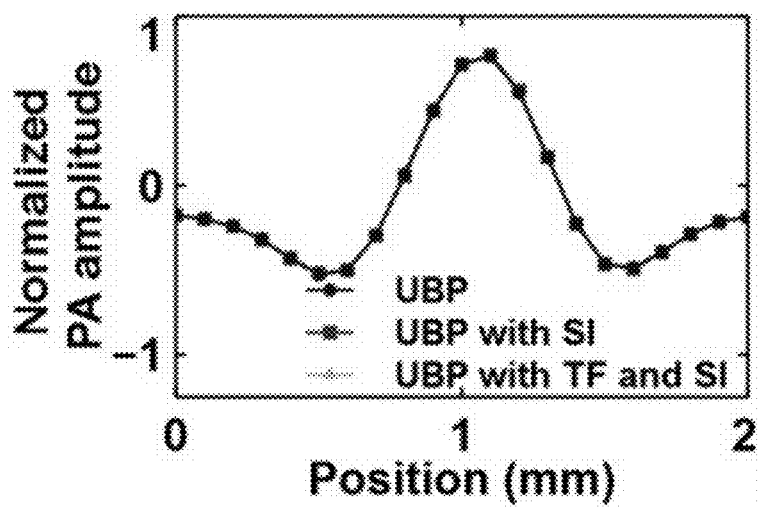
FIG. 17 is a graph with a plot of profiles of lines using the three methods: (1) UBP reconstruction (2) UBP reconstruction and spatial interpolation, and (3) UBP reconstruction, spatial interpolation (SI), and location-dependent temporal filtering (TF).
Figure 18:
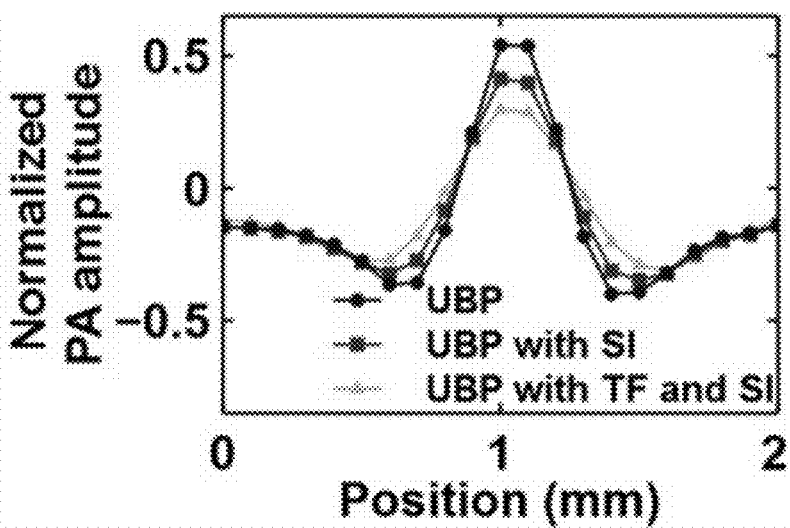
FIG. 18 is a graph with a plot of profiles of lines Q using image reconstruction (1) with UBP reconstruction (2) UBP reconstruction and spatial interpolation, and (3) UBP reconstruction, spatial interpolation, and location-dependent temporal filtering.

To quantify the impact of the antialiasing methods on image resolution, two lines at P and Q, respectively, were selected in each reconstructed image, and their profiles compared in FIGS. 17 and 18 respectively. FIG. 17 is a graph with a plot of profiles of line P using the three methods: (1) a first method with UBP reconstruction alone, (2) a second method with UBP reconstruction and spatial interpolation, and (3) a third method with UBP reconstruction, spatial interpolation (SI), and location-dependent temporal filtering (TF). FIG. 18 is a graph with a plot of profiles of line Q using the three methods. For signals from source points inside zone $S_1$, there is no spatial aliasing in spatial sampling, and spatial interpolation is accurate at the interpolation points. Moreover, location-dependent temporal filtering does not affect the signals when reconstructing inside zone $S_1$. Thus, the antialiasing techniques had little impact on the profile of line P (inside zone $S_1$) in this example, as shown in FIG. 17. For signals from source points outside zone S$_1$, the spatial interpolation is inaccurate due to spatial aliasing. Thus, directly applying spatial interpolation affects the profile of line Q (outside S$_1$). Location-dependent temporal filtering smooths the temporal signals before reconstructing outside zone S$_1$, thus it further smooths the profile of line Q, as shown in FIG. 18.

Complex Phantom Examples

Figure 19:
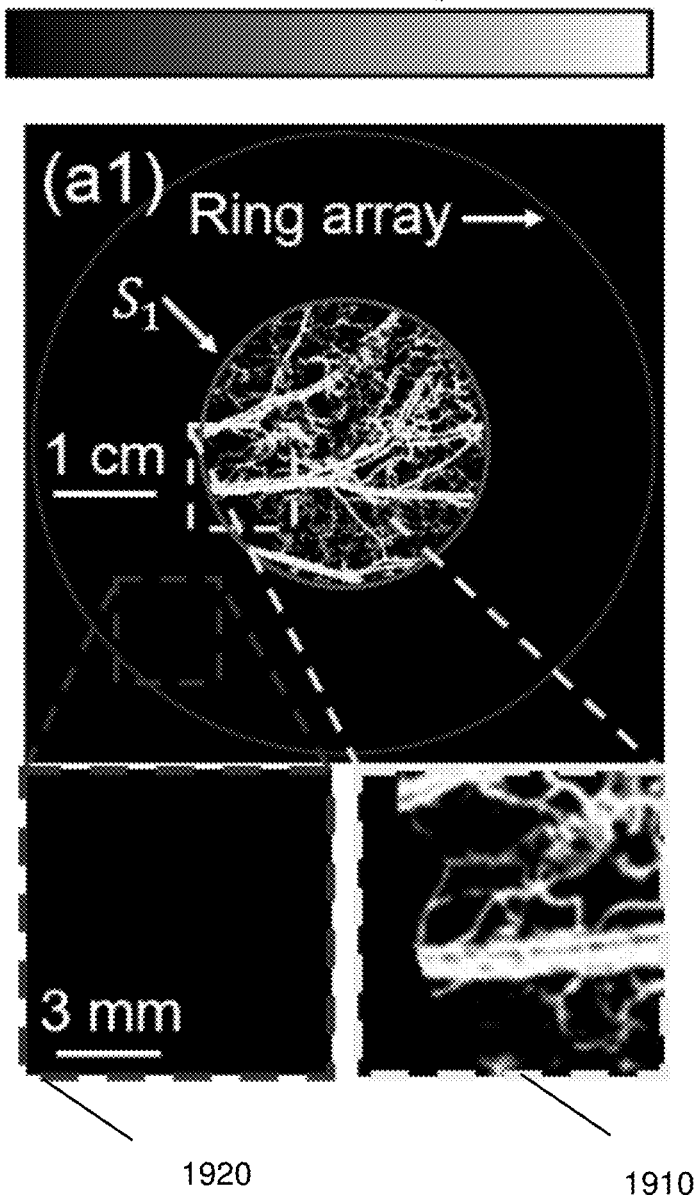
FIG. 19 is an illustration of ground truth of a simple initial pressure $p_0$ distribution for a first complex phantom, according to an implementation.
Figure 20A:
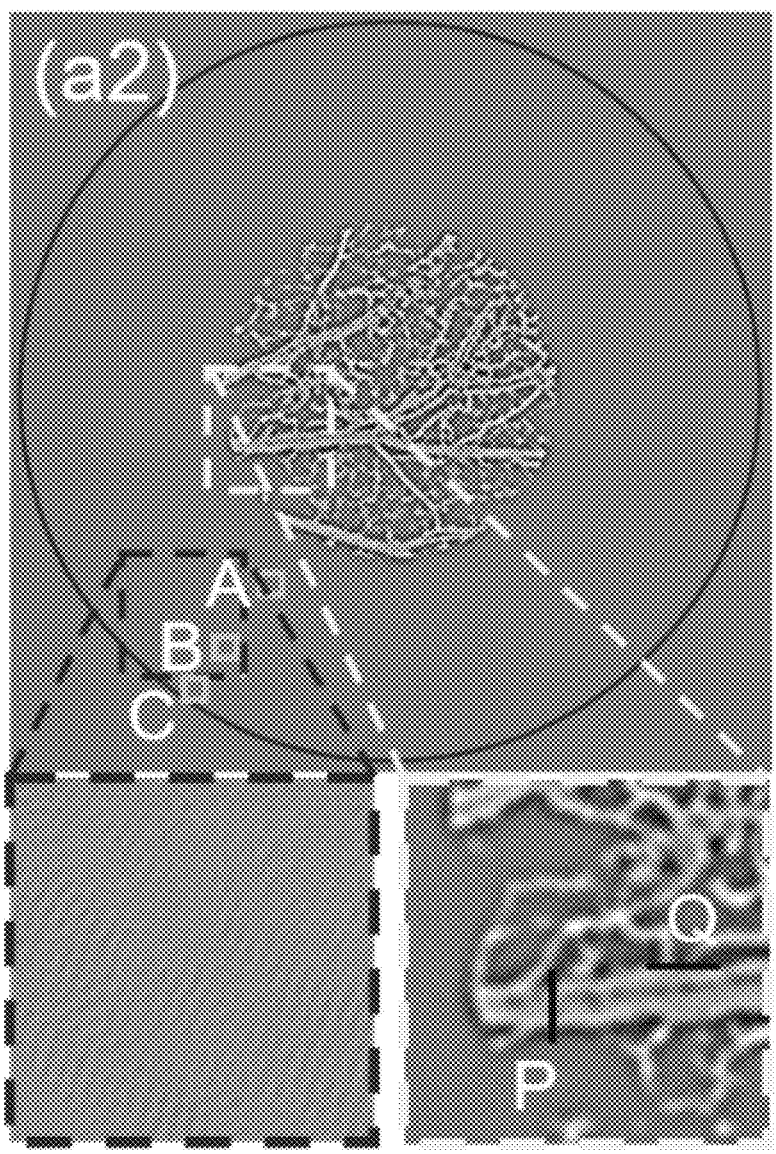
FIG. 20A is a reconstructed image of the first complex phantom object shown in FIG. 19 using a first antialiasing method including universal back projection reconstruction, according to an implementation.
Figure 20B:
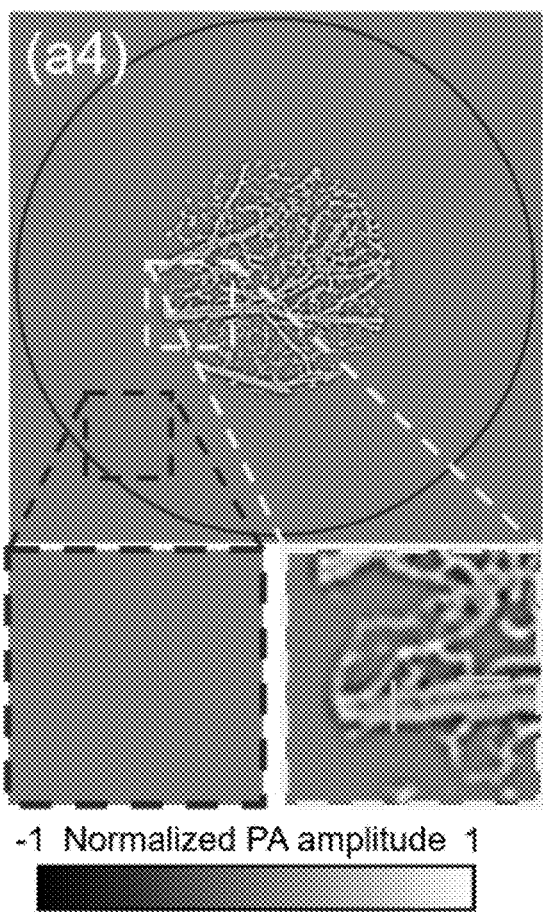
FIG. 20B is a reconstructed image of the first complex phantom object in FIG. 19 using the second method including UBP reconstruction and spatial interpolation, according to an implementation.
Figure 20C:
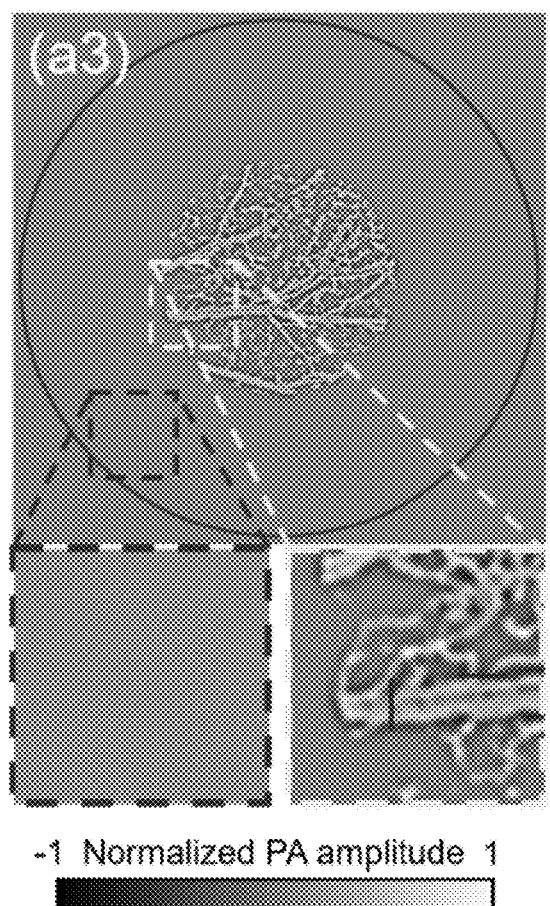
FIG. 20C is a reconstructed image of the first complex phantom object in FIG. 19 using a third method including UBP reconstruction, spatial interpolation, and location-dependent temporal filtering, according to an implementation.

FIG. 19 is an illustration of ground truth of a simple initial pressure p$_0$ distribution for a first complex phantom, according to an implementation. FIG. 20A is a reconstructed image of the first complex phantom object shown in FIG. 19 using a first antialiasing method including universal back projection reconstruction, according to an implementation. FIG. 20B is a reconstructed image of the first complex phantom object in FIG. 19 using the second method including UBP reconstruction and spatial interpolation, according to an implementation. FIG. 20C is a reconstructed image of the first complex phantom object in FIG. 19 using a third method including UBP reconstruction, spatial interpolation, and location-dependent temporal filtering, according to an implementation. The artifacts in red-boxed region are caused by spatial aliasing in IR, and they are mainly mitigated by SI.

Figure 21:
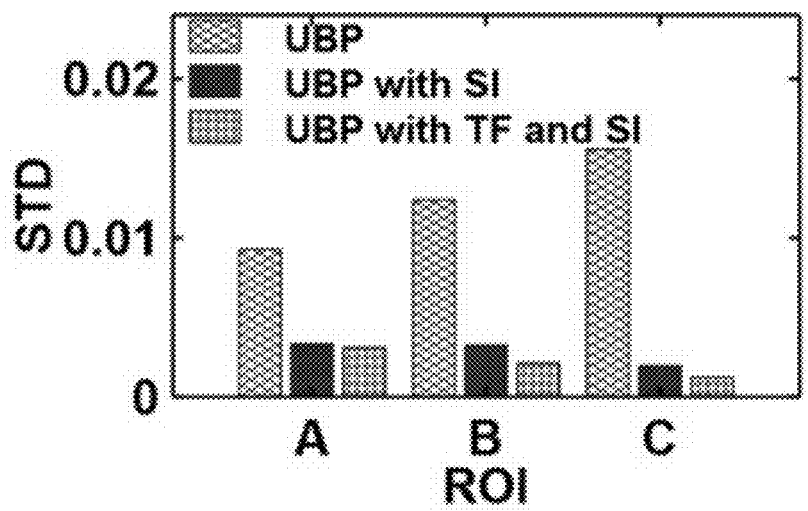
FIG. 21 is a graph with a plot of standard deviations of three regions of interest obtained using: (1) a first method with UBP reconstruction alone, (2) a second method with UBP reconstruction and spatial interpolation, and (3) a third method with UBP reconstruction, spatial interpolation, and location-dependent temporal filtering, according to implementations.
Figure 22:
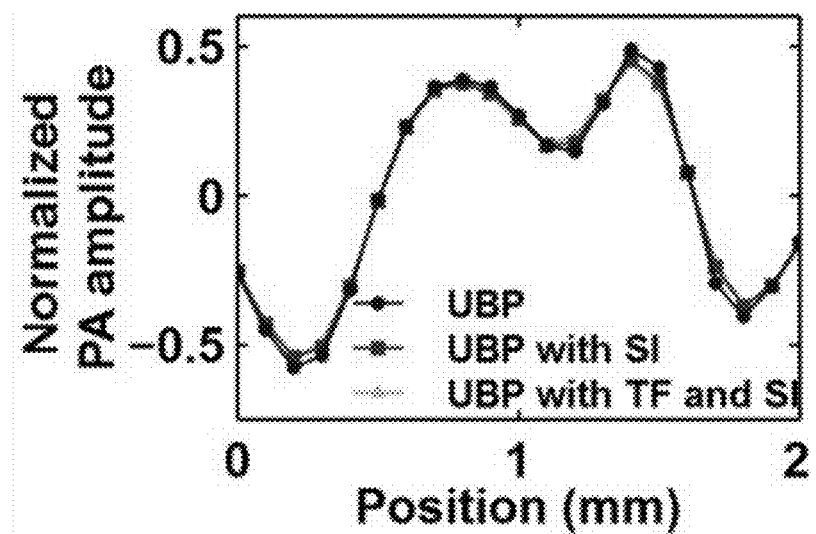
FIG. 22 is a graph with a plot of profiles of line P obtained using three methods, according to implementations.
Figure 23:
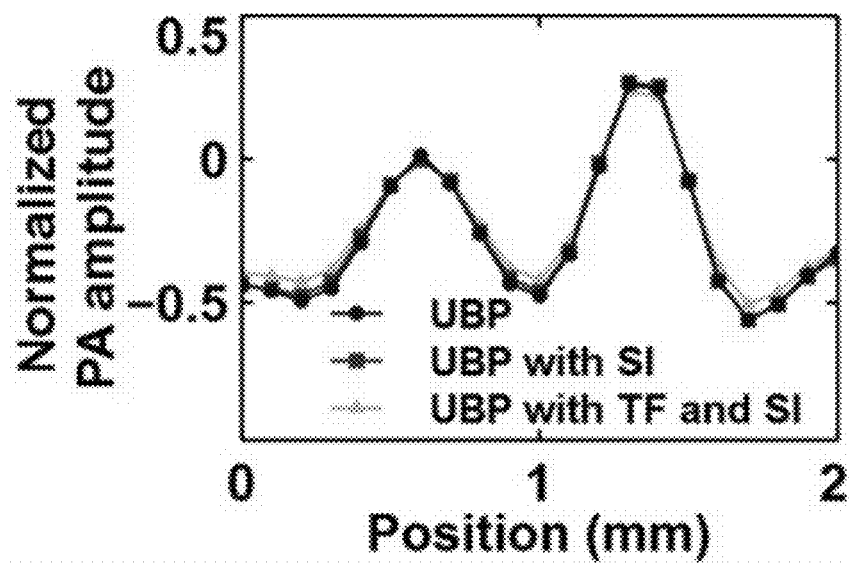
FIG. 23 is a graph with a plot of profiles of line Q obtained using three methods, according to implementations.

FIG. 21 is a graph with a plot of standard deviations of the regions of interest A-C using three methods: (1) a first method with UBP reconstruction alone, (2) a second method with UBP reconstruction and spatial interpolation, and (3) a third method with UBP reconstruction, spatial interpolation (SI), and location-dependent temporal filtering (TF). FIG. 22 is a graph with a plot of profiles of line P using the three methods. FIG. 23 is a graph with a plot of profiles of line Q using the three methods. The artifacts in the boxed region in are caused by spatial aliasing in SS and IR, and the artifacts are mitigated by TF and SI.

For the first complex phantom case, the object is completely within zone S$_1$, as shown in FIG. 19. The reconstructed images (reconstructions) of the object in FIG. 19 using the three methods: (1) a first method with UBP reconstruction alone, (2) a second method with UBP reconstruction and spatial interpolation, and (3) a third method with UBP reconstruction, spatial interpolation (SI), and location-dependent temporal filtering (TF) are shown in FIGS. 20A-20C respectively. Regions of interest A-C, each with an area of 1.2×1.2 mm$^2$, were chosen at locations with zero initial pressure. The standard deviations were calculated and compared, as shown in FIG. 21. Profiles of lines P and Q are shown in FIG. 22 and FIG. 23, respectively.

Figure 24:
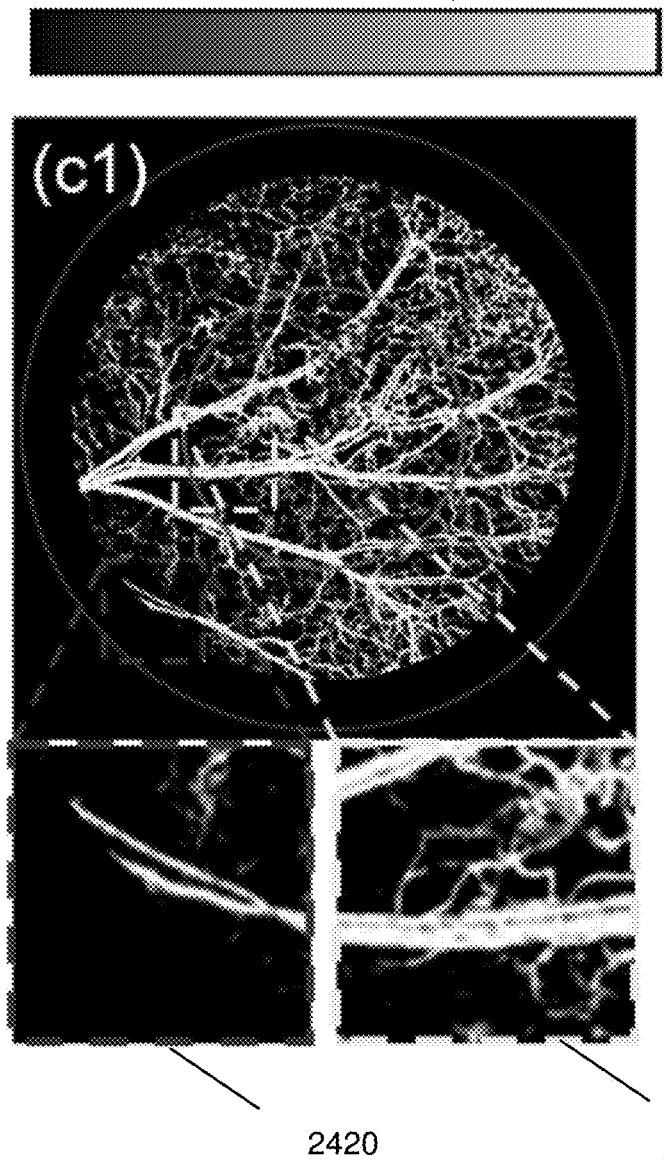
FIG. 24 is an illustration of ground truth of a simple initial pressure $p_0$ distribution for a second complex phantom, according to an implementation.
Figure 25A:
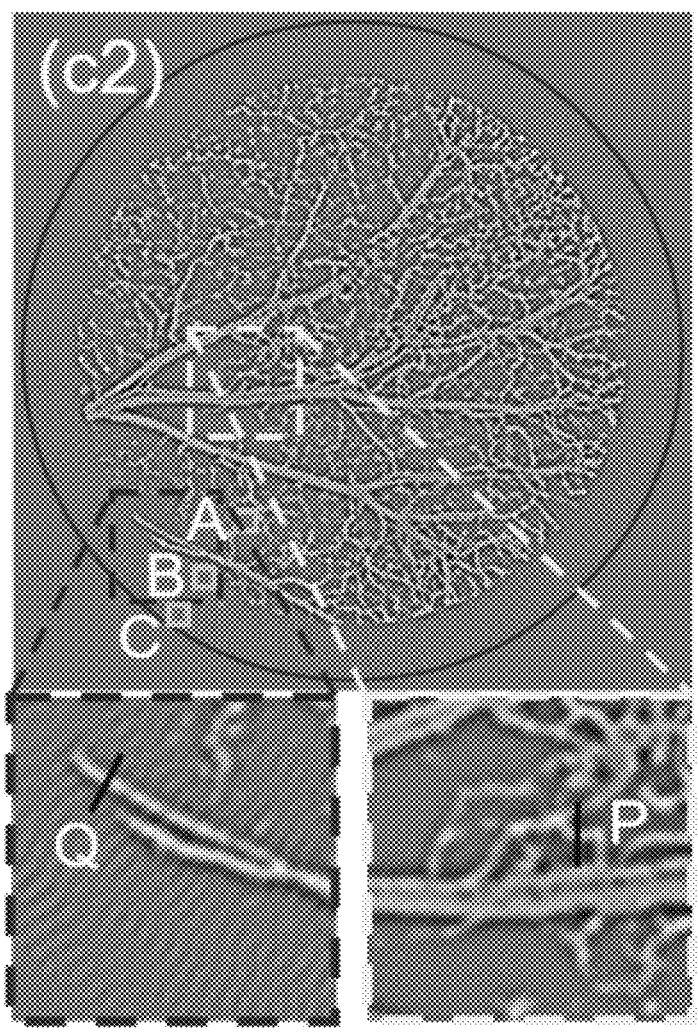
FIG. 25A is a reconstructed image of the second complex phantom object shown in FIG. 24 using a first antialiasing method including universal back projection reconstruction, according to an implementation.
Figure 25B:
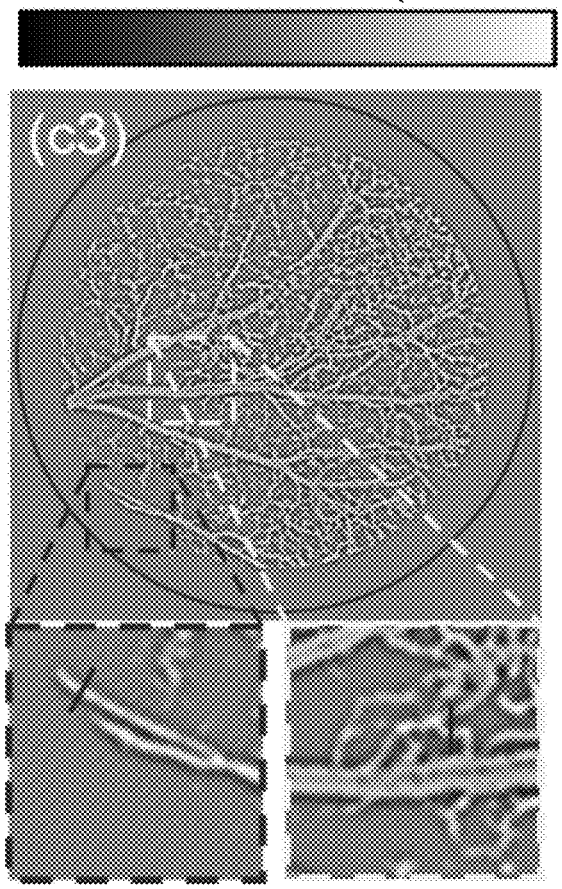
FIG. 25B is a reconstructed image of the second complex phantom object in FIG. 24 using the second method including UBP reconstruction and spatial interpolation, according to an implementation.
Figure 25C:
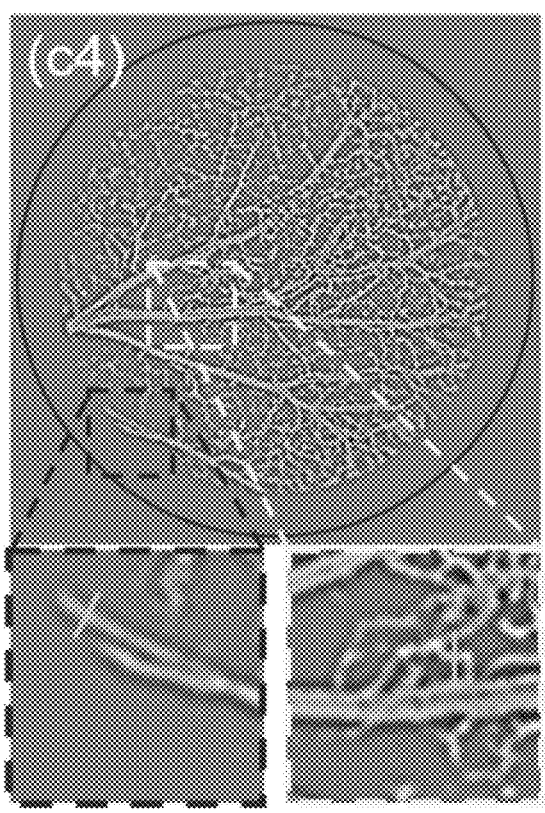
FIG. 25C is a reconstructed image of the second complex phantom object in FIG. 24 using a third method including UBP reconstruction, spatial interpolation, and location-dependent temporal filtering, according to an implementation.

FIG. 24 is an illustration of ground truth of a simple initial pressure p$_0$ distribution for a second complex phantom, according to an implementation. FIG. 25A is a reconstructed image of the second complex phantom object shown in FIG. 24 using a first antialiasing method including universal back projection reconstruction, according to an implementation. FIG. 25B is a reconstructed image of the second complex phantom object in FIG. 24 using the second method including UBP reconstruction and spatial interpolation, according to an implementation. FIG. 25C is a reconstructed image of the second complex phantom object in FIG. 24 using a third method including UBP reconstruction, spatial interpolation, and location-dependent temporal filtering, according to an implementation.

Figure 26:
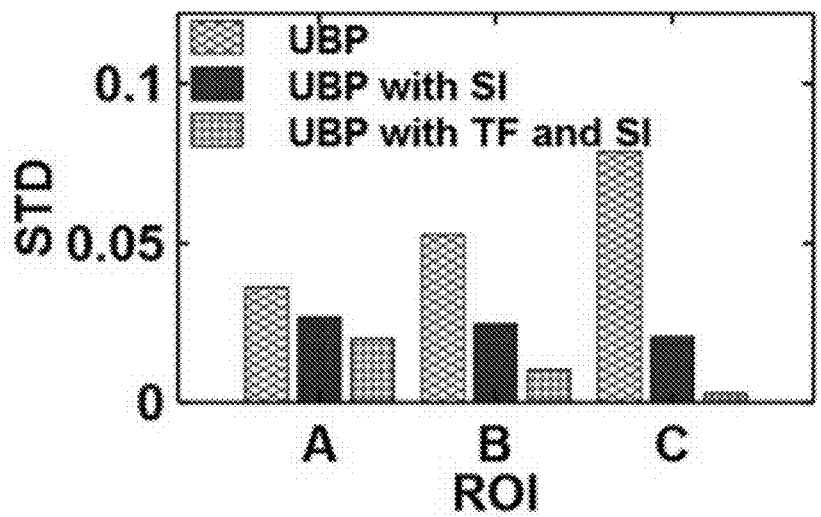
FIG. 26 is a graph with a plot of standard deviations of three regions of interest: (1) a first method with UBP reconstruction alone, (2) a second method with UBP reconstruction and spatial interpolation, and (3) a third method with UBP reconstruction, spatial interpolation (SI), and location-dependent temporal filtering (TF), according to implementations.
Figure 27:
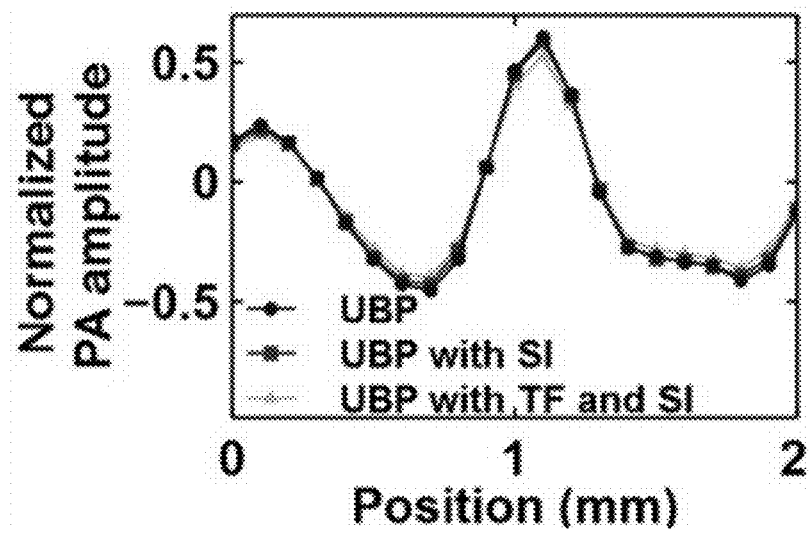
FIG. 27 is a graph with a plot of profiles of line P using the three methods, according to implementations.
Figure 28:
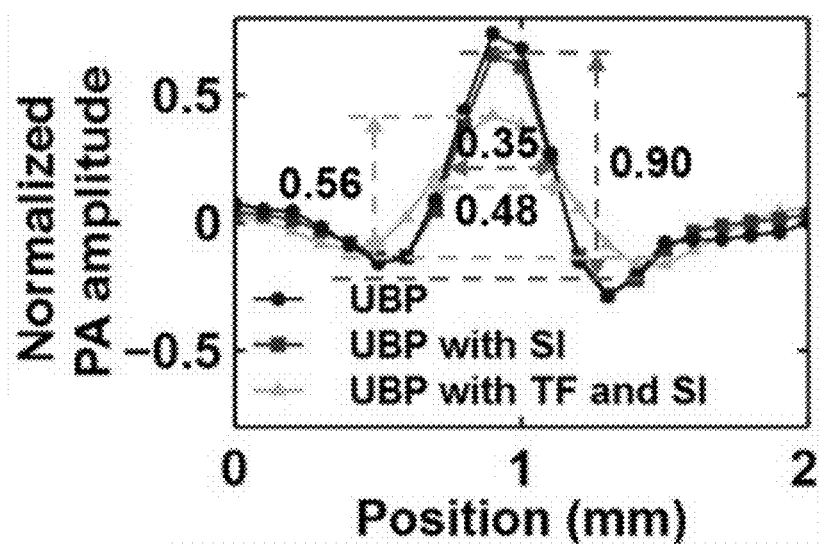
FIG. 28 is a graph with a plot of profiles of line Q using the three methods, according to implementations.

FIG. 26 is a graph with a plot of standard deviations of the regions of interest A-C using three methods: (1) a first method with UBP reconstruction alone, (2) a second method with UBP reconstruction and spatial interpolation, and (3) a third method with UBP reconstruction, spatial interpolation (SI), and location-dependent temporal filtering (TF). FIG. 27 is a graph with a plot of profiles of line P using the three methods. FIG. 28 is a graph with a plot of profiles of line Q using the three methods. The FWHM of the main lobe at was increased from 0.35 mm to 0.48 mm by temporal filtering, while the amplitude was changed from 0.90 to 0.56, respectively.

For the second complex phantom case, the object is outside of zone S$_1$, and covers most of the area inside the zone S$_0$, inside the full-ring transducer array, as shown in FIG. 24. The reconstructions of the object in FIG. 24 using the three methods are shown in FIGS. 25A-25C, respectively. The standard deviations of regions of interest A-C are compared in FIG. 26, while the profiles of lines P and Q are shown in FIG. 27 and FIG. 28, respectively. Although spatial interpolation mitigates the aliasing artifacts in both FIG. 20A and FIG. 25A, FIG. 20B and FIG. 25B, visible artifacts remain in the boxed region in FIG. 25C, but not in FIG. 20C.

It can also be seen in FIG. 21 and FIG. 26 that spatial interpolation shows more antialiasing effects on FIG. 20A than on FIG. 25A, while temporal filtering's antialiasing effect on FIG. 25A is more than on FIG. 20A. In fact, the aliasing artifacts in FIG. 20A are solely from the image reconstruction, while those in FIG. 25A are from both the spatial sampling and the image reconstruction. Thus, spatial interpolation works well in antialiasing for FIG. 20A, for which temporal filtering's smoothing effect slightly helps; but not as well for FIG. 25A due to the spatial aliasing in spatial sampling, for which temporal filtering may be necessary. In general, the aliasing artifacts are mitigated by spatial interpolation and further diminished by temporal filtering, as shown in both FIG. 21 and FIG. 26. The antialiasing methods maintain the image resolution well inside zone S$_1$, as shown in FIG. 22, FIG. 23, and FIG. 27. Due to spatial aliasing in spatial sampling for objects outside zone S$_1$, the profile of line Q is affected by spatial interpolation. Adding location-dependent temporal filtering further smooths the profile. The full width at half maximum (FWHM) of the main lobe in line Q's profile was increased by temporal filtering while the amplitude was reduced, as shown in FIG. 28. All these observations regarding the complex phantoms agree with the discussions about the simple phantom in FIG. 14.

V. In Vivo Experimental Results

Antialising techniques including spatial interpolation and location-dependent temporal filtering were applied to human breast imaging using a PACT system with spatiotermporal antialiasing. The PACT system employed a 512-element full-ring transducer array (e.g., the 512-element full-ring transducer array with a 110-mm radius, 2.25-MHz central frequency, 95% one-way bandwidth as sold by Imasonic, Inc.). Certain components of the PACT system were similar to those described in Lin, L. Hu, P., Shi, J., Appleton, C. M., Maslov, K., Li, L., Zhang, R., and Wang, L. V., "Single-breath-hold photoacoustic computed tomography of the breast," Nat. Commun., vol. 9, no. 1, p. 2352, 2018, which is hereby incorporated by reference in its entirety. Based on the point source measurements discussed in Section VII, the cutoff frequency, $f_c$, is estimated to be about 3.80 Mhz. The acquired signals were filtered by an antialiasing filter including a third-order lowpass Butterworth filter and a sinc filter, both with cutoff frequency 3.80 MHz. Thus, the one-way Nyquist zone S$_1$ had a radius $$r = \frac{Nc}{4\pi f_c} \approx 16.0 \text{ mm},$$

while the two-way Nyquist zone $S_2$ has a radius of 8.0 mm. A speed of sound of c=1.49 mm·μs$^{-1}$ was used in these determinations.

Figure 29A:
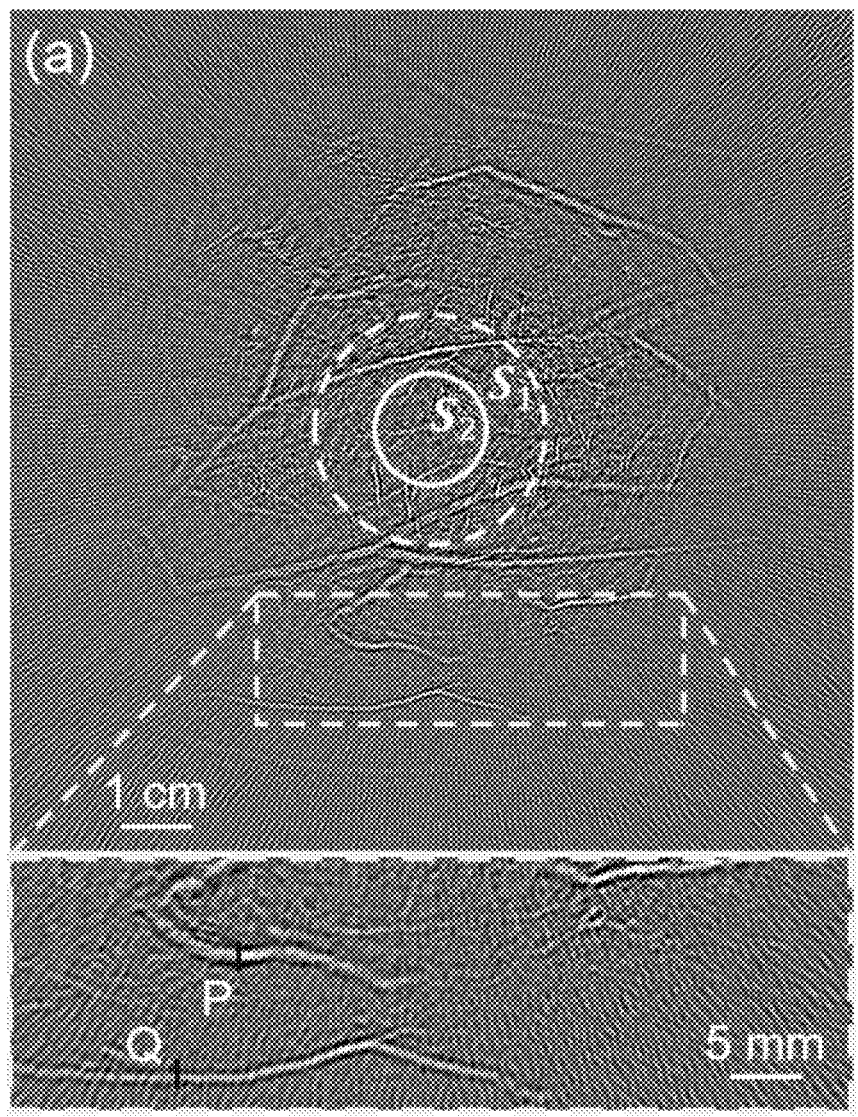
FIG. 29A is a reconstructed image using universal back propagation without either spatial interpolation or location-based temporal filtering, according to an implementation.
Figure 29B:
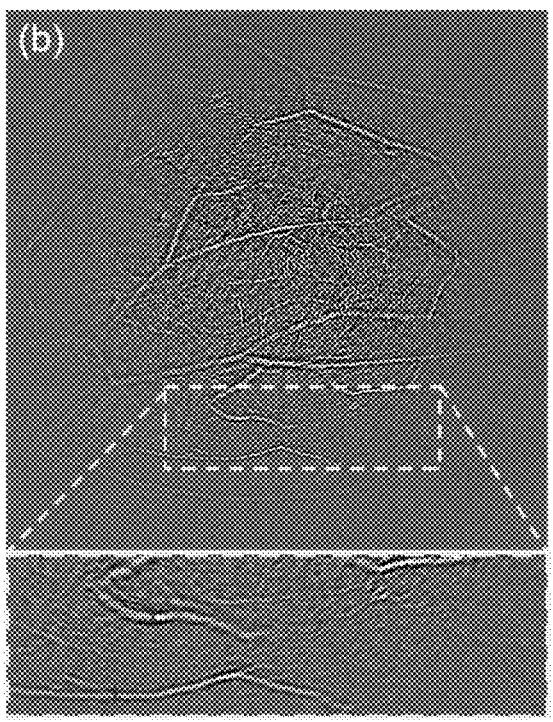
FIG. 29B is a reconstructed image of the same region in FIG. 29A using universal back propagation with spatial interpolation, according to an implementation.
Figure 29C:
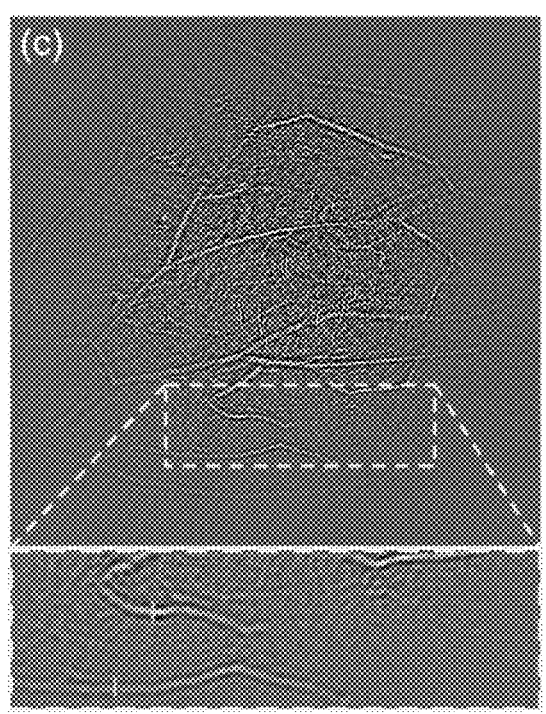
FIG. 29C is a reconstructed image of the same region in FIG. 29A using universal back propagation with spatial interpolation and location-based temporal filtering, according to an implementation.
Figure 30:
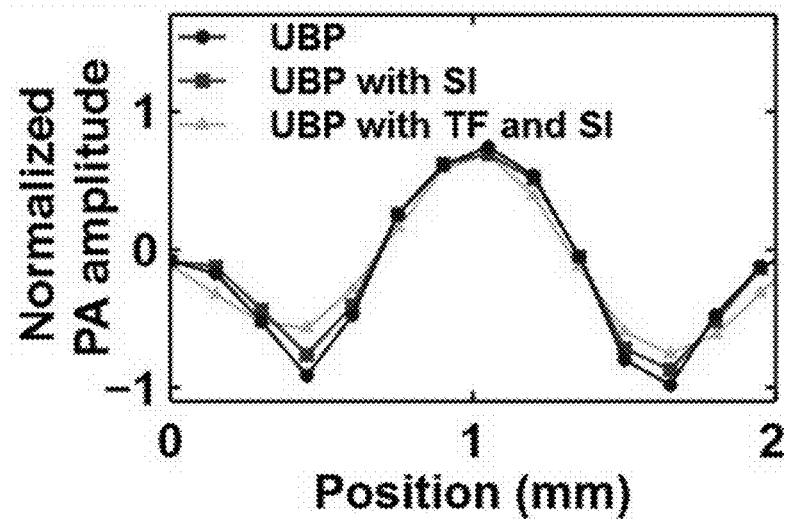
FIG. 30 is a graph with a plot of profiles of line P using the three methods, according to implementations.
Figure 31:
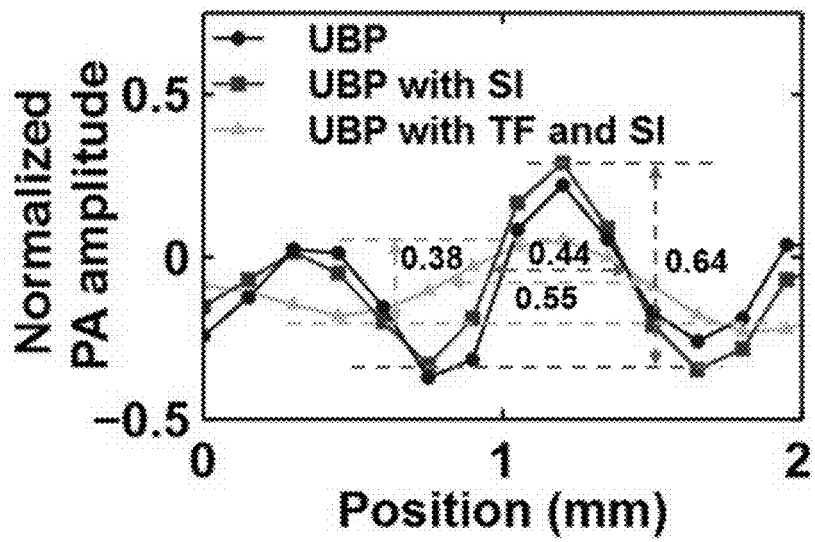
FIG. 31 is a graph with a plot of profiles of line Q using the three methods, according to implementations.

FIG. 29A is a reconstructed image using universal back propagation without either spatial interpolation or location-based temporal filtering. Boundaries of zones $S_1$ and $S_2$ are shown as dashed and solid circles, respectively. FIG. 29B is a reconstructed image of the same region in FIG. 29A using universal back propagation with spatial interpolation. FIG. 29C is a reconstructed image of the same region in FIG. 29A using universal back propagation with spatial interpolation and location-based temporal filtering. FIG. 30 is a graph with a plot of profiles of line P using the three methods. FIG. 31 is a graph with a plot of profiles of line Q using the three methods. The FWHM of the main lobe at as increased from 0.44 mm to 0.55 mm by temporal filtering, while the amplitude was changed from 0.64 to 0.38, respectively.

Using universal back propagation, a cross-sectional image of a breast was reconstructed as shown in FIG. 29A. The aliasing artifacts are shown in the peripheral regions in the closeup subset in a boxed region. After applying spatial interpolation of the raw data, the reconstructed image from using universal back propagation is shown in FIG. 29B. Applying location-based temporal filtering and spatial interpolation, the reconstructed image from using universal back propagation is shown in FIG. 29C. As can be seen from a comparison of closeup subsets, the image quality is improved by spatial interpolation, and the aliasing artifacts are further mitigated by location-based temporal filtering. For comparison, the profiles of lines P and Q for the three images are shown in FIGS. 30 and 31 respectively. As shown by the numerical simulation, image resolution outside zone $S_1$ is compromised by both spatial interpolation and temporal filtering. Temporal filtering smooths the profiles, as shown in FIG. 30 and FIG. 31. Quantitatively, as shown in FIG. 31, temporal filtering increases the FWHM of the main lobe of line Q's profile and reduces the amplitude.

In certain implementations, spatial interpolation maintains the resolution in the one-way Nyquist zone $S_1$ while mitigating the artifacts caused by aliasing in image reconstruction. Spatial interpolation extends the aliasing-free zone from $S_2$ to $S_1$. For objects outside $S_1$, spatial interpolation may not be useful due to spatial aliasing in spatial sampling. Adding location-dependent temporal filtering does not affect the resolution inside $S_1$. For objects outside $S_1$, temporal filtering suppresses high-frequency signals to satisfy the temporal Nyquist sampling requirement. Although reducing the spatial resolution in the affected regions, temporal filtering mitigates aliasing in spatial sampling and makes the spatial interpolation accurate, thus further extends the aliasing-free zone.

VI. Spectrum Analysis

In one aspect, a PACT method includes operations that perform a spectrum analysis of $$\frac{\|r''-r_n\|}{c} h_e''\left(\frac{\|r''-r_n\|}{c} - \frac{\|r'_m-r_n\|}{c}\right)$$

in Eqn. 17. To analyze spatial aliasing in image reconstruction, expression $$\frac{\|r''-r_n\|}{c} h_e''\left(\frac{\|r''-r_n\|}{c} - \frac{\|r'_m-r_n\|}{c}\right)$$

is analyzed, which is a multiplication of a fast-change variable $$h_e''\left(\frac{\|r''-r_n\|}{c} - \frac{\|r'_m-r_n\|}{c}\right)$$

and a slow-change variable $$\frac{\|r''-r_n\|}{c}.$$

Considering that the multiplication is equivalent to a convolution in the frequency domain, the multiplication of $$\frac{\|r''-r_n\|}{c}$$

causes spectrum change.

To simplify, only the case with $$r'_m = (r', 0) \text{ and}$$

$$r'' = \left(r'\cos\left(2\arccos\frac{r'}{R}\right), r'\sin\left(2\arccos\frac{r'}{R}\right)\right)$$

is considered. In this case, $$\frac{\|r''-r_n\|}{c} - \frac{\|r'_m-r_n\|}{c}$$

can achieve the maximum sampling step size $$\frac{4\pi r'}{N}$$

as n varies Eqn. 19, where spatial aliasing is the most severe. Given an element location r(θ)=R (cos θ, sin θ), one defines $$f_1(\theta) = \frac{\|r''-r(\theta)\|}{c} \text{ and}$$

$$f_2(\theta) = h_e''\left(\frac{\|r''-r(\theta)\|}{c} - \frac{\|r'_m-r(\theta)\|}{c}\right).$$

Then, the continuous form of $$\frac{\|r''-r_n\|}{c} h_e''\left(\frac{\|r''-r_n\|}{c} - \frac{\|r'_m-r_n\|}{c}\right)$$

can be expressed as $f_1(\theta) f_2(\theta)$. Applying the Fourier transformation to $f_1(f)f_2(\theta)$ and $f_2(\theta)$, $F(f_1 f_2)(f)$ and $F(f_2)$ $(f)$ are obtained, respectively. F denotes the Fourier transformation operator. The difference between the two normalized spectra is expressed as $$\max_{f} \left| \frac{|F(f_1 f_2)(f)|}{\max_{f}|F(f_1 f_2)(f)|} - \frac{|F(f_2)(f)|}{\max_{f}|F(f_2)(f)|} \right|,$$

which is a function of $r' \in [0, R)$. The difference is calculated between the two normalized spectra for a full-ring array geometry with a radius R=110 mm, and a point source response $h_e'$ measured through experiments where the speed of sound used was c=1.49 mm·µs$^{-1}$.

Figure 32:
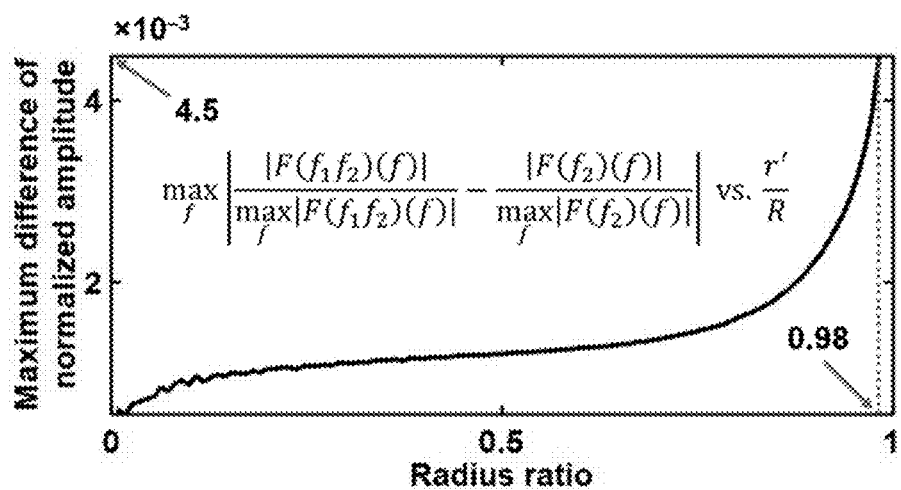
FIG. 32 is a graph with a plot of the difference between the normalized spectra $$\frac{|F(f_1,f_2)(f)|}{\max_f |F(f_1,f_2)(f)|} \text{ and } \frac{|F(f_2)(f)|}{\max_f |F(f_2)(f)|},$$

FIG. 32 is a graph with a plot of the difference between the normalized spectra $$\frac{|F(f_1 f_2)(f)|}{\max_{f}|F(f_1 f_2)(f)|} \text{ and } \frac{|F(f_2)(f)|}{\max_{f}|F(f_2)(f)|}$$

for $-r' \in [0, 0.98R]$, according to one implementation. As shown in FIG. 32, for $-r' \in [0, 0.98R]$, one finds a $$\max_{f} \left| \frac{|F(f_1 f_2)(f)|}{\max_{f}|F(f_1 f_2)(f)|} - \frac{|F(f_2)(f)|}{\max_{f}|F(f_2)(f)|} \right| < 4.5 \times 10^{-3}.$$

When r' approaches R, singularity occurs. For a system with a frequency-dependent SNR smaller than $$\frac{1}{4.5 \times 10^{-3}} \approx 222,$$

which may almost always true for experimental cases discussed herein, the difference between the two normalized spectra is negligible. Therefore, to simplify the problem, the spatial aliasing in $$h_e''\left(\frac{\|r'' - r_n\|}{c} - \frac{\|r_m' - r_n\|}{c}\right)$$

may represent the spatial aliasing in $$\frac{\|r'' - r_n\|}{c} h_e''\left(\frac{\|r'' - r_n\|}{c} - \frac{\|r_m' - r_n\|}{c}\right).$$

VII. Estimation of Upper Cutoff Frequency of an Ultrasonic Transducer Array.

In one aspect, a PACT method includes operations that use point source measurements to estimate the upper cutoff frequency $f_c$ of an ultrasonic transducer array. In one operation, an estimation of the point source response is obtained from the point source measurements. In another operation, the response's amplitude and noise level in the frequency domain is quantified and the frequency-dependent signal-to-noise ratio (SNR) is calculated.

The upper cutoff frequency $f_c$, higher than the central frequency, is selected where the frequency-dependent SNR decreases to one for the first time. The full-ring transducer array is used to acquire the photoacoustic signals generated by a point source located at the array center for J repetitions (e.g., J=100). From each acquisition, N measurements are obtained from N transducer elements (e.g., N=512). Based on Eqn. 5, by ignoring a constant factor, the point source response can be expressed as $h_e'(t)$. The measurement of $h_e'(t)$ by the n-th element in the j-th acquisition is denoted as $h_{e,j,n}'(t)$. In each acquisition, the mean response is denoted as:

$$h_{e,j}'(t) = \frac{1}{N}\sum_{n=1}^{N} h_{e,j,n}'(t), t > 0, j = 1, 2, ..., J. \quad \text{(Eqn. 37)}$$

The point source response $h_e'(t)$ can be further estimated using $$\overline{h_e'}(t) = \frac{1}{J}\sum_{j=1}^{J} h_{e,j}'(t), t > 0. \quad \text{(Eqn. 38)}$$

The normalized value of $\overline{h_e'}(t)$ is shown in FIG. 33A. By applying the Fourier transformation to $h_{e,j}'(t)$ and $\overline{h_e'}(t)$, $F(h_{e,j}')(f)$ and $F(\overline{h_e'})(f)$, can be respectively obtained. The normalized amplitude of $F(\overline{h_e'})(f)$ is shown in FIG. 33B.

FIGS. 33A-E are graphs showing the results of operations of a method of estimating an upper cutoff frequency, according to one implementation. FIG. 33A is a graph of a Normalized estimated point source response $$\left(\frac{\overline{h_e'}(t)}{\max \overline{h_e'}(t)}\right),$$

according to one implementation. FIG. 33B is a graph of a normalized frequency spectrum of the estimated point source response $$\left(\frac{|F(\overline{h_e'})(f)|}{\max_{f}|F(\overline{h_e'})(f)|}\right),$$

according to an implementation. FIG. 33C is a graph of the normalized frequency spectrum of the noise $$STD\left(\frac{\sigma_1(f)}{\max_{f}|F(\overline{h_e'})(f)|}\right),$$

according to an implementation. FIG. 33D is a graph of a frequency-dependent signal-to-noise ratio $$\left(SNR_1(f) = \frac{|F(\overline{h_e'})(f)|}{\sigma_1(f)}\right).$$

The upper cutoff frequency is estimated to be $f_c$=3.80 MHz in this example where the SNR equals to one. FIG. 33E is a graph of frequency-dependent SNR of the derivative of the point source response $$\left(SNR_2(f) = \frac{|F(\overline{h_e''})(f)|}{\sigma_2(f)}\right).$$

The upper cutoff frequency is also estimated to be $f_c$=3.80 MHz. FIG. 33F is a graph of Normalized frequency spectra of $h_e'$ (frequency components with frequencies higher than 3.80 MHz are removed) and $h_e''$ $$\left(\frac{|F(\overline{h_e'})(f)|}{\max_f|F(h_e')(f)|} \text{ and } \frac{|F(\overline{h_e''})(f)|}{\max_f|F(h_e'')(f)|}, \text{ respectively}\right).$$

Since each pixel value in a reconstructed image is obtained by a weighted summation of the signals from N elements, the noise in $h_{e,j}'(t)$ (rather than $h_{e,j,n}'(t)$) can be used to approximate the noise in the reconstructed image. At a frequency of $f$, the noise STD in $h_{e,j}'(t)$ can be estimated as:

$$\sigma_1(f) \approx \sqrt{\frac{1}{J-1}\sum_{j=1}^{J}|F(h_{e,j}')(f) - F(\overline{h_e'})(f)|^2}. \quad \text{(Eqn. 39)}$$

Thus, the frequency-dependent SNR can be defined as:

$$SNR_1(f) = \frac{|F(\overline{h_e'})(f)|}{\sigma_1(f)}. \quad \text{(Eqn. 40)}$$

The normalized value of $\sigma_1(f)$ and the value of $SNR_1(f)$ are shown in FIGS. 33C and 33D, respectively. The cutoff frequency $f_c$ to be 3.80 MHz (higher than the central frequency 2.25 MHz) was selected where SNR($f$) decreases to one for the first time.

To observe the temporal differentiation effect on the spectrum of $\overline{h_e'}$, $\overline{h_e'}$ in Eqns. 39 and 40 is replaced with $\overline{h_e''}$, and obtain $\sigma_2(f)$ and $SNR_2(f)$, respectively. As shown in FIG. 33E, the upper cutoff frequency obtained from $SNR_2(f)$ is the same as that from $SNR_1(f)$. In practice, before the UBP reconstruction, the acquired signals may be filtered with an antialiasing filter, e.g., a third-order lowpass Butterworth filter and a sinc filter (both with a cutoff frequency of $f_c$). Thus, the frequency components with frequencies higher than 3.80 MHz are removed from $h_e'$. The normalized frequency spectrum of $h_e'$ and $h_e''$ are shown in FIG. 33F. As can be seen, although the spectrum is positively shifted by the temporal differentiation for $f<3.80$ MHz, the cutoff frequency 3.80 MHz doesn't change.

VIII. Sampling Step Size Approximation

In one aspect, a PACT method includes one or more operations that approximate sampling step size. An approximation of the sampling step size is used in in Eqn. 9, particularly its maximum value $$\frac{2\pi r'}{N}.$$

The accuracy or this approximation is shown by expressing the sampling step size as a Taylor expansion with the Lagrange remainder. The first-order term is the approximation being used. By analyzing the higher-order terms, the differences are negligible.

FIG. 34 is a schematic diagram of a full-ring transducer array with a radius R, where two adjacent detection element locations $r_1$ and $r_2$, and a source point location r' are marked.

These and the following locations are also regarded as vectors from the origin O to them. Vectors $r_1$ and $r_2$ form an angle γ, whose bisector intersects with the ring $$r_{\frac{3}{2}}.$$

Vector $$r_{\frac{3}{2}} - r'$$

forms an angle α' with the tangential dotted line that is perpendicular to vector $$r_{\frac{3}{2}}.$$

Vectors $$r_{\frac{3}{2}}$$

and r' form an angle φ, while vectors $$r_{\frac{3}{2}} - r'$$

and −r' form an angle β. The angle formed by vectors $$-r_{\frac{3}{2}}$$

and $$r' - r_{\frac{3}{2}}$$

can be expressed as $$\alpha' - \frac{\pi}{2}.$$

This graph is used to estimate the sampling step size $\|r'-r_1\|-\|r'-r_2\|$.

FIG. 35 is a graph with a plot of examples of errors calculated using $$r'\gamma = \frac{2\pi r'}{N}$$

to approximate s(r', θ) for −r'=0.95$r_1$'≈15.2 mm, according to an implementation. FIG. 35 is a graph with a plot of errors calculated using $$r'\gamma = \frac{2\pi r'}{N}$$

to approximate s(r', θ) for −r'=6.75$r_1$'≈107.8 mm, according to an implementation.

For the full-ring transducer array with radius R and centered at the origin O, one considers a source point at r' and two adjacent detection element locations $r_1$ and $r_2$ as shown in FIG. 34. The bisector of the angle formed by vectors $r_1$ and $r_2$ intersects with the ring at $$r_{\frac{3}{2}}.$$

Vectors $r_1$ and $r_2$ form an angle γ; vectors $$r_{\frac{3}{2}}$$

and r' form an angle φ; while vectors $$r_{\frac{3}{2}} - r'$$

and −r' form an angle β. Vector $$r_{\frac{3}{2}} - r'$$

forms an angle α with the tangential clotted line crossing point $$-r_{\frac{3}{2}}$$

Thus, the angle formed by vectors $$r_{\frac{3}{2}}.$$

and $$r' - r_{\frac{3}{2}}$$

can be expressed as $$\alpha' - \frac{\pi}{2}.$$

Based on the Law of Cosines in triangles O$r_1$r' and O$r_2$r':

$$\|r' - r_1\| = \sqrt{R^2 + r'^2 - 2Rr'\cos\left(\varphi + \frac{\gamma}{2}\right)},$$ (Eqn. 41)

and $$\|r' - r_2\| = \sqrt{R^2 + r'^2 - 2Rr'\cos\left(\varphi - \frac{\gamma}{2}\right)},$$ (Eqn. 42)

respectively. To simplify the following expression, functions are defined as:

$$f_{k,\varphi}(\gamma) = \frac{\|r' - r_1\|}{2} = \sqrt{1 + k^2 - 2k\cos\left(\varphi + \frac{\gamma}{2}\right)},$$ (Eqn. 43)

and $$g(k, \varphi) = k(1 + k^2 - 2k\cos\varphi)^{-\frac{1}{2}}\sin\varphi,$$ (Eqn. 44)

$$q(k, \varphi) = \frac{1 - k^2}{1 + k^2 - 2k\cos\varphi} \in \left[\frac{1-k}{1+k}, \frac{1+k}{1-k}\right].$$ (Eqn. 45)

Here, letting $$k = \frac{r'}{R}.$$

using the Law or Sines in triangle O$r_{3/2}$r'

$$\frac{\sin\varphi}{R\sqrt{1 + k^2 - 2k\cos\varphi}} = \frac{\sin\beta}{R} = \frac{\sin\left(\alpha' - \frac{\pi}{2}\right)}{r'} = \frac{-\cos\alpha'}{r'},$$ (Eqn. 46)

One has $$g(k,\varphi) = -\cos\alpha',$$ (Eqn. 47)

and $$|g(k,\varphi)| = k\sin\beta \le k, k \in [0,1), \varphi \in [0,2\pi).$$ (Eqn. 48)

One can prove that $$f_{k,\varphi}(-\gamma) = \frac{\|r' - r_2\|}{R},$$ (Eqn. 49)

$$f'_{k,\varphi}(\gamma) = \frac{1}{2}g\left(k, \varphi + \frac{\gamma}{2}\right),$$ (Eqn. 50)

and $$f'''_{k,\varphi}(\gamma) = \frac{g\left(k, \varphi + \frac{\gamma}{2}\right)}{8}\left(\frac{1}{4} + \frac{1}{3}q^2\left(k, \varphi + \frac{\gamma}{2}\right)\right).$$ (Eqn. 51)

Then, based on the Taylor expansion of $f_{k,\varphi}(\gamma) - f_{k,\varphi}(-\gamma)$, sampling step size can be expressed as:

$$\left|\|r' - r_1\| - \|r' - r_2\|\right| = R|f_{k,\varphi}(\gamma) - f_{k,\varphi}(-\gamma)| =$$

$$R\left|2f'_{k,\varphi}(0)\gamma + \frac{f'''_{k,\varphi}(\gamma) + f'''_{k,\varphi}(-\gamma')}{6}\gamma^3\right| = \mathrm{sgn}(\sin\varphi)g(k,\varphi)R\gamma -$$

$$\frac{\mathrm{sgn}(\sin\varphi)g\left(k, \varphi + \frac{\gamma'}{2}\right)}{48}\left(\frac{1}{4} + \frac{3}{4}q^2\left(k, \varphi + \frac{\gamma'}{2}\right)\right)R\gamma^3 -$$ (Eqn. 52)

$$\frac{\text{sgn}(\sin\varphi)g\left(k, \varphi - \frac{\gamma'}{2}\right)}{48}\left(\frac{1}{4} + \frac{3}{4}q^2\left(k, \varphi - \frac{\gamma'}{2}\right)\right)R\gamma^3,$$

for some $\gamma' \in (0, \gamma)$.

The following sign function is used:

$$\text{sgn}(x) = \begin{cases} -1, & x < 0, \\ 0, & x = 0, \\ 1, & x > 0. \end{cases} \quad \text{(Eqn. 53)}$$

In practice, it is the maximum sampling step size that affects spatial aliasing. To have a finer estimation of the maximum sampling step size, first the upper bound of $\|r'-r_1\|-\|r'-r_2\|$ is estimated. For $$\varphi \in \left[\frac{\gamma}{2}, \pi - \frac{\gamma}{2}\right] \cup \left[\pi + \frac{\gamma}{2}, 2\pi - \frac{\gamma}{2}\right], \text{sgn}(\sin\varphi)g\left(k, \varphi \pm \frac{\gamma'}{2}\right) \geq 0.$$

Thus, the high order terms in Equation (44) are nonpositive, and one has:

$$\|r' - r_1\| - \|r' - r_2\| \leq |g(k, \varphi)| R\gamma = |\cos\alpha'| R\gamma, \quad \text{(Eqn. 54)}$$

$$k \in [0, 1), \varphi \in \left[\frac{\gamma}{2}, \pi - \frac{\gamma}{2}\right] \cup \left[\pi + \frac{\gamma}{2}, 2\pi - \frac{\gamma}{2}\right], \gamma = \frac{2\pi}{N} \leq \frac{\pi}{4}.$$

$N \geq 8$ is assumed. For $$\varphi \in \left[-\frac{\gamma}{2}, \frac{\gamma}{2}\right], \varphi + \frac{\gamma}{2} \in [0, \gamma] \text{ and } \varphi - \frac{\gamma}{2} \in [-\gamma, 0],$$

which means that both $f_{k,\varphi}(\gamma)$ and $f_{k,\varphi}(-\gamma)$ belong to $[\sqrt{1+k^2-2k}, \sqrt{1+k^2-2k\cos\gamma}]$. Thus:

$$\|r' - r_1\| - \quad \text{(Eqn. 55)}$$
$$\|r' - r_2\| \leq R\left|\sqrt{1+k^2-2k} - \sqrt{1+k^2-2k\cos\gamma}\right| =$$
$$R\left|f_{k,\frac{\gamma}{2}}(-\gamma) - f_{k,\frac{\gamma}{2}}(\gamma)\right| \leq \left|g\left(k, \frac{\gamma}{2}\right)\right| R\gamma \leq r'\gamma.$$

Here, using Inequality in Eqn. 54 with $$\varphi = \frac{\gamma}{2}.$$

Similarly, for $$\varphi \in \left[\pi - \frac{\gamma}{2}, \pi + \frac{\gamma}{2}\right],$$

gives us:

$$\|r' - r_1\| - \|r' - r_2\| \leq \left|g\left(k, \pi - \frac{\gamma}{2}\right)\right| R\gamma \leq r'\gamma. \quad \text{(Eqn. 56)}$$

Combining Inequalities in Eqns. 54-56, the upper bound of the sampling step size is:

$$\|r' - r_1\| - \|r' - r_2\| \leq r'\gamma = \frac{2\pi r'}{N}, \quad \text{(Eqn. 57)}$$
$$N \geq 2, r' \in [0, R), \varphi \in [0, 2\pi).$$

Next, the lower bound of $\|r'-r_1\|-\|r'r_2\|$ is estimated for $$\beta = \frac{\pi}{2}.$$

In fact, for each $r'>0$, there exist N locations of $r'$ evenly distributed on the circle $\|r'\|=r'$ such that $$\beta = \frac{\pi}{2}.$$

For each location, $\varphi=\arccos k$, $\text{sgn}(\sin \varphi)=1$, and $g(k, \arccos k)=k$. In general, there may be singularities in $$q\left(k, \varphi + \frac{\gamma'}{2}\right).$$

To avoid the singularities, it is assumed that $k \leq \cos\gamma$, which means that $\varphi=\arccos$ $$k \in \left[\gamma, \frac{\pi}{2}\right].$$

Thus, $$\cos\left(\varphi + \frac{\gamma'}{2}\right) < \cos\varphi \text{ and } \cos\left(\varphi - \frac{\gamma'}{2}\right) < \cos\left(\varphi - \frac{\gamma}{2}\right),$$

leading to:

$$q\left(k, \varphi + \frac{\gamma'}{2}\right) < q(k, \arccos k) = 1, \quad \text{(Eqn. 58)}$$

and $$q\left(k, \varphi - \frac{\gamma'}{2}\right) < q\left(k, \arccos k - \frac{\gamma}{2}\right) = \quad \text{(Eqn. 59)}$$

$$\frac{1-k^2}{1+k^2-2k^2\cos\frac{\gamma}{2}-2k\sqrt{1-k^2}\sin\frac{\gamma}{2}},$$

respectively. One can validate that $$\frac{\partial q(k, \arccos k - \frac{\gamma}{2})}{\partial k} \geq 0$$

is equivalent to $$k^2 \leq \frac{1 + \cos\frac{\gamma}{2}}{5 - 3\cos\frac{\gamma}{2}}.$$

Thus $$q(k, \arccos k - \frac{\gamma}{2}),$$

as a function of k, is monotonically increasing on $$\left[0, \sqrt{\frac{1 + \cos\frac{\gamma}{2}}{5 - 3\cos\frac{\gamma}{2}}}\right).$$

Note that $$\cos^2\frac{\gamma}{2} < \frac{1 + \cos\frac{\gamma}{2}}{5 - 3\cos\frac{\gamma}{2}}$$

is equivalent to $$\left(\cos\frac{\gamma}{2} - 1\right)^2 \left(3\cos\frac{\gamma}{2} + 1\right) \geq 1,$$

which is valid for any $$\gamma = \frac{2\pi}{N} \leq \frac{\pi}{4}.$$

Thus, for any $$k \leq \cos\gamma, k^2 \leq \cos^2\gamma < \cos^2\frac{\gamma}{2} \leq \frac{1 + \cos\frac{\gamma}{2}}{5 - 3\cos\frac{\gamma}{2}}.$$

Based on the monotonicity of $$q(k, \arccos k - \frac{\gamma}{2})$$

as a function or k:

$$q(k, \arccos k - \frac{\gamma}{2}) \leq q(\cos\gamma, \arccos(\cos\gamma) - \frac{\gamma}{2}) = \frac{1 - \cos^2\gamma}{1 + \cos^2\gamma - 2\cos\gamma\cos\frac{\gamma}{2}}. \quad \text{(Eqn. 60)}$$

Further, it can be proven that $$q(\cos\gamma, \frac{\gamma}{2}) < 4$$

is equivalent to $$\left(\cos\frac{\gamma}{2} - 1\right)^2 \left(5\cos^2\frac{\gamma}{2} + 6\cos\frac{\gamma}{2} + 2\right) > 0,$$

which is valid for any $$\gamma = \frac{2\pi}{N} \leq \frac{\pi}{4}.$$

In summary, for any $k \leq \cos\gamma$: and $$0 < q(k, \arccos k + \frac{\gamma'}{2}) < 1, \quad \text{(Eqn. 61)}$$

and $$0 < q(k, \arccos k - \frac{\gamma'}{2}) < 4. \quad \text{(Eqn. 62)}$$

Combining Inequalities in Eqn. 61 and Eqn. 62 with Eqn. 52, the following it obtained:

$$\|r' - r_1\| - \|r' - r_2\| \geq r'\gamma - \frac{53r'}{192}\gamma^3 = \frac{2\pi r'}{N} \frac{53r'}{192}\left(\frac{2\pi}{N}\right)^3, \quad \text{(Eqn. 63)}$$

$$N \geq 8, r' \leq R\cos\gamma, \varphi = \arccos\frac{r'}{R}.$$

For any source point=(r' cos θ, r' sin θ), the ma sampling step size can be expressed as:

$$s(r', \theta) = \max_{\varphi} \|\|r' - r_1\| - \|r' - r_2\|\|. \quad \text{(Eqn. 64)}$$

From Inequality in Eqn. 57:

$$s(r', \theta) \leq \frac{2\pi r'}{N}, N \geq 8, r' \in [0, R). \quad \text{(Eqn. 65)}$$

According to Inequality in Eqn. 63, there exist at least N values of θ evenly distributed in [0,2π) such that:

$$s(r', \theta) \geq \frac{2\pi r'}{N} - \frac{53\, r'}{192}\left(\frac{2\pi}{N}\right)^3, N \geq 8, r' \leq R\cos\gamma. \quad \text{(Eqn. 66)}$$

As can be seen in Eqn. 65, using $$r'\gamma = \frac{2\pi r'}{N}$$

to approximate s(r', θ) is sufficient for the antialiasing analysis; while $$\frac{53\, r'}{192}\left(\frac{2\pi}{N}\right)^3\left(\frac{\lambda_c}{2}\right)^{-1}$$

in Eqn. 66 can be used to estimate the necessity to further reduce the upper bound of s(r', θ) for the N specific values of θ. For general values of θ, numerical simulation can be used to estimate.

Next, these estimations are evaluated in numerical simulations and in vivo experiments. In both cases, N=512. The radius constraint, from inequality (58), $$\frac{r'}{R} \leq \cos\gamma = \cos\frac{2\pi}{N} \approx 1 - 7.5 \times 10^{-5}$$

is substantially close to the intrinsic constraint $$\left(\frac{r'}{R} < 1\right).$$

For the numerical simulations, c=1.5 mm·μs⁻¹, R=30 mm, and $f_c$=4.5 MHz, thus $$\frac{53\, r'}{192}\left(\frac{2\pi}{N}\right)^3\left(\frac{\lambda_c}{2}\right)^{-1} < \frac{53\, R}{192}\left(\frac{2\pi}{N}\right)^3\left(\frac{2f_c}{c}\right) < 9.2 \times 10^{-5}.$$

For in vivo experiments, c=1.49 mm·μs⁻¹, R=110 mm, and $f_c$=3.80 MHz, then $$\frac{53\, r'}{192}\left(\frac{2\pi}{N}\right)^3\left(\frac{\lambda_c}{2}\right)^{-1} < 2.9 \times 10^{-4}.$$

In both cases, for the N specific values of θ, using $$\frac{2\pi r'}{N}$$

to approximate s(r', θ) is substantially accurate. For general values of θ, numerical simulation are used to observe the approximation error for source locations on two circles (in vivo experiment cases): one with a radius of $$0.95\, r'_1 = 0.95\frac{N\lambda_c}{4\pi} \approx 15.2 \text{ mm}$$

($r_1'$ is the radius of $S_1$), the other with a radius of 6.75$r_1'$≈107.8 mm (98% of R).

FIG. 35 is a graph with plot of $$e(r', \theta) = (r'\gamma - s(r', \theta))\left(\frac{\lambda_c}{2}\right)^{-1}$$

against $$\theta \in \left[0, \frac{\pi}{60}\right]$$

for r'=0.95$r_1'$, according to an implementation. FIG. 36 is a graph with plot of e(r', θ)=

$$(r'\gamma) - s(r', \theta))\left(\frac{\lambda_c}{2}\right)^{-1}$$

against $$\theta \in \left[0, \frac{\pi}{60}\right] \text{ for } r' = 6.75\, r'_1,$$

according to an implementation.

Each bar marks a choice of θ assumed in inequality in Eqn. 66. One can see from FIGS. 35 and 36 that, for general values of θ, to further reduce the upper bound of s(r', θ) is unnecessary.

Modifications, additions, or omissions may be made to any of the above-described embodiments without departing from the scope of the disclosure. Any of the embodiments described above may include more, fewer, or other features without departing from the scope of the disclosure. Additionally, the steps of described features may be performed in any suitable order without departing from the scope of the disclosure. Also, one or more features from any embodiment may be combined with one or more features of any other embodiment without departing from the scope of the disclosure. The components of any embodiment may be integrated or separated according to particular needs without departing from the scope of the disclosure.

It should be understood that certain aspects described above can be implemented in the form of logic using computer software in a modular or integrated manner. Based on the disclosure and teachings provided herein, a person of ordinary skill in the art will know and appreciate other ways and/or methods to implement the present invention using hardware and a combination of hardware and software.

Any of the software components or functions described in this application, may be implemented as software code using any suitable computer language and/or computational software such as, for example, Java, C, C#, C++ or Python, LabVIEW, Mathematica, or other suitable language/computational software, including low level code, including code written for field programmable gate arrays, for example in VHDL. The code may include software libraries for functions like data acquisition and control, motion control, image acquisition and display, etc. Some or all of the code may also run on a personal computer, single board computer, embedded controller, microcontroller, digital signal processor, field programmable gate array and/or any combination thereof or any similar computation device and/or logic device(s). The software code may be stored as a series of instructions, or commands on a CRM such as a random access memory (RAM), a read only memory (ROM), a magnetic media such as a hard-drive or a floppy disk, or an optical media such as a CD-ROM, or solid stage storage such as a solid state hard drive or removable flash memory device or any suitable storage device. Any such CRM may reside on or within a single computational apparatus, and may be present on or within different computational apparatuses within a system or network. Although the foregoing disclosed embodiments have been described in some detail to facilitate understanding, the described embodiments are to be considered illustrative and not limiting. It will be apparent to one of ordinary skill in the art that certain changes and modifications can be practiced within the scope of the appended claims.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

What is claimed is:

1. A photoacoustic computed tomography method, comprising:
   acquiring photoacoustic data recorded by one or more data acquisition devices of a photoacoustic computed tomography system;
   applying location-based temporal filtering to the photoacoustic data acquired, wherein applying the location-based temporal filtering comprises
   determining an upper cutoff frequency based at least in part on geometry of an ultrasonic transducer array of the photoacoustic computed tomography system and applying one or more lowpass filters with the upper cutoff frequency; and
   reconstructing one or more photoacoustic images from the filtered photoacoustic data.

2. The photoacoustic computed tomography method of claim 1, wherein the upper cutoff frequency is determined based on a distance from a reconstruction location to a center of the ultrasonic transducer array.

3. The photoacoustic computed tomography method of claim 1, further comprising applying spatial interpolation after the application of the location-based temporal filtering.

4. The photoacoustic computed tomography method of claim 3, wherein universal back projection is used to reconstruct the one or more photoacoustic images.

5. A photoacoustic computed tomography method, comprising:
   acquiring photoacoustic data;
   determining whether a reconstruction location is (a) at or inside, or (b) outside an alias-free region; and
   if it is determined that the reconstruction location is outside the alias-free region,
   (i) applying location-based temporal filtering to the photoacoustic data acquired, wherein the application of the location-based temporal filtering comprises applying one or more lowpass filters with an upper cutoff frequency based at least in part on geometry of an ultrasonic transducer array; and
   (ii) reconstructing one or more photoacoustic images from the filtered photoacoustic data.

6. The photoacoustic computed tomography method of claim 5, wherein the determination of whether the reconstruction location is (a) at or inside, or (b) outside the alias-free region is based on Nyquist sampling criterion.

7. The photoacoustic computed tomography method of claim 5, wherein the method further comprises applying spatial interpolation after the application of the location-based temporal filtering if it is determined that the reconstruction location is outside the alias-free region.

8. The photoacoustic computed tomography method of claim 5, wherein the one or more photoacoustic images are reconstructed from the filtered photoacoustic data using universal back propagation.

9. A non-transitory computer readable media for generating one or more photoacoustic images of a specimen being imaged, the non-transitory computer readable media, when read by one or more processors, is configured to perform operations comprising:
   acquiring photoacoustic data recorded by one or more data acquisition devices of a photoacoustic computed tomography system;
   applying location-based temporal filtering to the photoacoustic data acquired, wherein applying the location-based temporal filtering comprises
   determining an upper cutoff frequency based at least in part on geometry of an ultrasonic transducer array of the photoacoustic computed tomography system and applying one or more lowpass filters with the upper cutoff frequency; and
   reconstructing one or more photoacoustic images from the filtered photoacoustic data.

10. The non-transitory computer readable media of claim 9, wherein the upper cutoff frequency is determined based on a distance from a reconstruction location to a center of the ultrasonic transducer array.

11. The non-transitory computer readable media of claim 9, wherein the operations further comprise applying spatial interpolation after the application of the location-based temporal filtering.

12. The non-transitory computer readable media of claim 9, wherein universal back propagation is used to reconstruct the one or more photoacoustic images.

13. A non-transitory computer readable media for generating one or more photoacoustic images of a specimen being imaged, the non-transitory computer readable media, when read by one or more processors, is configured to perform operations comprising:
    acquiring photoacoustic data;
    determining whether a reconstruction location is (a) at or inside, or (b) outside an alias-free region; and
    if it is determined that the reconstruction location is outside the alias-free region,
    (i) applying location-based temporal filtering to the photoacoustic data acquired, wherein the application of the location-based temporal filtering comprises applying one or more lowpass filters with an upper cutoff frequency based at least in part on geometry of an ultrasonic transducer array; and
    (ii) reconstructing one or more photoacoustic images from the filtered photoacoustic data.

14. The non-transitory computer readable media of claim 13, wherein the determination of whether the reconstruction location is (a) at or inside, or (b) outside the alias-free region is based on Nyquist sampling criterion.

15. The non-transitory computer readable media of claim 13, wherein the operations further comprise applying spatial interpolation after the application of the location-based temporal filtering if it is determined that the reconstruction location is outside the alias-free region.

16. The non-transitory computer readable media of claim 13, wherein the one or more photoacoustic images are reconstructed using universal back propagation.

* * * * *